United States Patent
Gohil et al.

(10) Patent No.: US 11,926,822 B1
(45) Date of Patent: Mar. 12, 2024

(54) THREE-DIMENSIONAL SPATIAL ANALYSIS

(71) Applicant: 10x Genomics, Inc., Pleasanton, CA (US)

(72) Inventors: Shalini Gohil, Pleasanton, CA (US); Eswar Prasad Ramachandran Iyer, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 12 days.

(21) Appl. No.: 17/481,810

(22) Filed: Sep. 22, 2021

Related U.S. Application Data

(60) Provisional application No. 63/082,150, filed on Sep. 23, 2020.

(51) Int. Cl.
C12N 15/10 (2006.01)
(52) U.S. Cl.
CPC .............................. *C12N 15/1065* (2013.01)
(58) Field of Classification Search
None
See application file for complete search history.

(56) References Cited

U.S. PATENT DOCUMENTS

| | | | |
|---|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Tang et al., Chemical Society Reviews, "Click" reactions to construct bioactive peptide conjugates, pp. 1-27 (2014) (Year: 2014).*
U.S. Appl. No. 16/353,937, filed Mar. 14, 2019, Frisen et al.
U.S. Appl. No. 17/707,189, filed Mar. 29, 2022, Chell et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.

(Continued)

*Primary Examiner* — Nancy J Leith
*Assistant Examiner* — Jessica D Parisi
(74) *Attorney, Agent, or Firm* — Fish & Richardson P.C.

(57) ABSTRACT

This disclosure relates to compositions and methods for three-dimensional spatial profiling of analytes in a biological sample. The methods include use of a hydrogel comprising one or more polymers that include a phenol moiety, an azide moiety, or an alkyne moiety.

20 Claims, 21 Drawing Sheets

Specification includes a Sequence Listing.

(56) References Cited

U.S. PATENT DOCUMENTS

| | | |
|---|---|---|
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |

(56) References Cited

U.S. PATENT DOCUMENTS

| | | |
|---|---|---|
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,208,982 B2 | 2/2019 | Bannish et al. |
| 10,227,639 B2 | 3/2019 | Levner et al. |
| 10,266,888 B2 | 4/2019 | Daugharthy et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 2001/0055764 A1 | 12/2001 | Empendocles et al. |
| 2002/0040275 A1 | 4/2002 | Cravatt |
| 2002/0048766 A1 | 4/2002 | Doyle et al. |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |

(56) References Cited

U.S. PATENT DOCUMENTS

| | | |
|---|---|---|
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024555 A1 | 1/2016 | Church et al. |
| 2016/0024576 A1 | 1/2016 | Chee |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |

(56) References Cited

U.S. PATENT DOCUMENTS

| | | |
|---|---|---|
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251833 A1 | 9/2018 | Daugharthy et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0354774 A1 | 11/2020 | Church et al. |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |

(56) References Cited

U.S. PATENT DOCUMENTS

| | | |
|---|---|---|
| 2022/0017951 A1* | 1/2022 | Ramachandran Iyer .................... C12Q 1/6841 |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |

(56) References Cited

FOREIGN PATENT DOCUMENTS

| | | |
|---|---|---|
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210353 | 12/2014 |
| WO | WO-2015031691 A1 * | 3/2015 .......... B01L 3/50857 |
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |

(56) References Cited

FOREIGN PATENT DOCUMENTS

| WO | WO 2021/207610 | 10/2021 |
|---|---|---|
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |

OTHER PUBLICATIONS

[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdI9It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdI9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Bechara et al., "Cell-penetrating peptides: 20 years later, where do we stand?," FEBS Lett., Jun. 2013, 587(12):1693-702.

(56) References Cited

OTHER PUBLICATIONS

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolognesi et al., "Multiplex Staining by Sequential Immunostaining and Antibody Removal on Routine Tissue Sections," J. Histochem. Cytochem., Aug. 2017, 65(8):431-444.
Bolotin et al., "MiXCR: software for comprehensive adaptive immunity profiling, " Nat Methods., May 2015, 12(5):380-1.
Boulé et al., "Terminal deoxynucleotidyl transferase indiscriminately incorporates ribonucleotides and deoxyribonucleotides," J Biol Chem., Aug. 2001, 276(33):31388-93.
Boulgakov et al., "From Space to Sequence and Back Again: Iterative DNA Proximity Ligation and its Applications to DNA-Based Imaging, " bioRxiv, 2018, 24 pages.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Davis et al., "Coatings on mammalian cells: interfacing cells with their environment," Journal of Biological Engineering, 2019, 13(5):1-28.
Deamer et al., "Characterization of nucleic acids by nanopore analysis," Acc Chem Res., Oct. 2002, 35(10):817-25.

(56) References Cited

OTHER PUBLICATIONS

Dean et al., "Comprehensive human genome amplification using multiple displacement amplification," Proc Natl. Acad. Sci. USA, 2002, 99(8):5261-66.

Deng et al., "Spatial Epigenome Sequencing at Tissue Scale and Cellular Level," BioRxiv, Mar. 2021, 40 pages.

Dressman et al., "Transforming single DNA molecules into fluorescent magnetic particles for detection and enumeration of genetic variations," Proc. Natl. Acad. Sci. USA, 2003, 100(15):8817-8822.

Drmanac et al., "CoolMPS™: Advanced massively parallel sequencing using antibodies specific to each natural nucleobase," BioRxiv, 2020, 19 pages.

Druley et al., "Quantification of rare allelic variants from pooled genomic DNA," Nat. Methods, 2009, 6(4):263-65.

Duncan et al., "Affinity chromatography of a sequence-specific DNA binding protein using Teflon-linked oligonucleotides," Anal. Biochem., 1988, 169(1):104-108.

Eagen, "Principles of Chromosome Architecture Revealed by Hi-C," Trends in Biochemical Sciences, Jun. 2018, 43(6):469-478.

Eberwine, "Amplification of mRNA populations using aRNA generated from immobilized oligo(dT)-T7 primed cDNA," BioTechniques, 1996, 20(4):584-91.

Eguiluz et al., "Multitissue array review: a chronological description of tissue array techniques, applications and procedures," Pathology Research and Practice, 2006, 202(8):561-568.

Eldridge et al., "An in vitro selection strategy for conferring protease resistance to ligand binding peptides," Protein Eng Des Sel., 2009, 22(11):691-698.

Ellington et al., "Antibody-based protein multiplex platforms: technical and operational challenges," Clin Chem, 2010, 56(2):186-193.

Eng et al., "Profiling the transcriptome with RNA SPOTs," Nat Methods., 2017, 14(12):1153-1155.

Evers et al., "The effect of formaldehyde fixation on RNA: optimization of formaldehyde adduct removal," J Mol Diagn., May 2011, 13(3):282-8.

Fire et al., "Rolling replication of short DNA circles," Proc. Natl. Acad. Sci., 1995, 92(10):4641-4645.

Flanigon et al., "Multiplex protein detection with DNA readout via mass spectrometry," N. Biotechnol., 2013, 30(2):153-158.

Fluidigm, "Equivalence of Imaging Mass Cytometry and Immunofluorescence on FFPE Tissue Sections," White Paper, 2017, 12 pages.

Fodor et al., "Light-directed, spatially addressable parallel chemical synthesis," Science, 1995, 251(4995):767-773.

Forster et al., "A human gut bacterial genome and culture collection for improved metagenomic analyses," Nature Biotechnology, 2019, 37(2):186-192.

Frese et al., "Formylglycine aldehyde Tag—protein engineering through a novel post-translational modification," ChemBioChem., 2009, 10(3):425-27.

Fu et al., "Continuous Polony Gels for Tissue Mapping with High Resolution and RNA Capture Efficiency," bioRxiv, 2021, 20 pages.

Fu et al., "Counting individual DNA molecules by the stochastic attachment of diverse labels," PNAS, 2011, 108(22):9026-9031.

Fu et al., "Repeat subtraction-mediated sequence capture from a complex genome," Plant J., Jun. 2010, 62(5):898-909.

Fullwood et al., "Next-generation DNA sequencing of paired-end tags (PET) for transcriptome and genome analyses," Genome Res., 2009, 19(4):521-532.

Ganguli et al., "Pixelated spatial gene expression analysis from tissue," Nat Commun., Jan. 2018, 9(1):202, 9 pages.

Gansauge et al., "Single-stranded DNA library preparation from highly degraded DNA using T4 DNA ligase," Nucleic Acids Res., Jun. 2017, 45(10):e79, 10 pages.

Gao et al., "A highly homogeneous expansion microscopy polymer composed of tetrahedron-like monomers," bioRxiv, Oct. 22, 2019, 23 pages (Preprint).

Gao et al., "Q&A: Expansion microscopy," BMC Biology, 15:50, 9 pages, 2017.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.

Gerard et al., "Excess dNTPs minimize RNA hydrolysis during reverse transcription," Biotechniques, Nov. 2002, 33(5):984, 986, 988, 990.

Gill et al., "Nucleic acid isothermal amplification technologies: a review," Nucleosides Nucleotides Nucleic Acids, Mar. 2008, 27(3):224-43.

Glass et al., "SIMPLE: a sequential immunoperoxidase labeling and erasing method," J. Histochem. Cytochem., Oct. 2009, 57(10):899-905.

Gloor, "Gene targeting in *Drosophila*," Methods Mol Biol., 2004, 260:97-114.

Gnanapragasam, "Unlocking the molecular archive: the emerging use of formalin-fixed paraffin-embedded tissue for biomarker research in urological cancer," BJU International, 2009, 105(2):274-278.

Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.

Goryshin et al., "Tn5 in vitro transposition," J Biol Chem., Mar. 1998, 273(13):7367-74.

Gracia Villacampa et al., "Genome-wide Spatial Expression Profiling in FFPE Tissues," bioRxiv, 2020, pp. 38 pages.

Grokhovsky, "Specificity of DNA cleavage by ultrasound," Molecular Biology, 2006, 40(2):276-283.

Gu et al., "Protein tag-mediated conjugation of oligonucleotides to recombinant affinity binders for proximity ligation," N Biotechnol., 2013, 30(2):144-152.

Gunderson et al., "Decoding randomly ordered DNA arrays," Genome Research, 2004, 14(5):870-877.

Guo et al., "Direct fluorescence analysis of genetic polymorphisms by hybridization with oligonucleotide arrays on glass supports," Nucleic Acids Res., Dec. 1994, 22(24):5456-65.

Gupta et al., "Single-cell isoform RNA sequencing characterizes isoforms in thousands of cerebellar cells," Nature Biotechnol., Oct. 2018, 36:1197-1202.

Hafner et al., "Identification of microRNAs and other small regulatory RNAs using cDNA library sequencing," Methods, Jan. 2008, 44(1):3-12.

Hahnke et al., "Striptease on glass: validation of an improved stripping procedure for in situ microarrays," J Biotechnol., Jan. 2007, 128(1):1-13.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Han et al., "3C and 3C-based techniques: the powerful tools for spatial genome organization deciphering", Molecular Cytogenetics (2018) 11: 21, 10 pages, 2018.

Hanauer et al., "Separation of nanoparticles by gel electrophoresis according to size and shape," Nano Lett., Sep. 2007, 7(9):2881-5.

Hardenbol et al., "Highly multiplexed molecular inversion probe genotyping: over 10,000 targeted SNPs genotyped in a single tube assay," Genome Res., Feb. 2005, 15(2):269-75.

Hardenbol et al., "Multiplexed genotyping with sequence-tagged molecular inversion probes," Nature Biotechnol., Jun. 2003, 21(6):673-678.

Hayes et al., "Electrophoresis of proteins and nucleic acids: I-Theory," BMJ, Sep. 1989, 299(6703):843-6.

He et al., "In situ synthesis of protein arrays," Current Opinion in Biotechnology, 2008, 19(1):4-9.

He et al., "Printing protein arrays from DNA arrays," Nature Methods, 2008, 5(2):175-77.

He, "Cell-free protein synthesis: applications in proteomics and biotechnology," New Biotechnology, 2008, 25(2-3):126-132.

Healy, "Nanopore-based single-molecule DNA analysis," Nanomedicine (Lond), Aug. 2007, 2(4):459-81.

Heinova et al., "Lactate Dehydrogenase Isoenzyme Electrophoretic Pattern in Serum and Tissues of Mammalian and Bird Origin," Electrophoresis: Life Sciences Practical Applications, 2018, p. 81.

(56) References Cited

OTHER PUBLICATIONS

Hejatko et al., "In situ hybridization technique for mRNA detection in whole mount *Arabidopsis* samples," Nature Protocols, 2006, 1(4):1939-1946.

Hessner et al., "Genotyping of factor V G1691A (Leiden) without the use of PCR by invasive cleavage of oligonucleotide probes," Clin Chem., Aug. 2000, 46(8 Pt 1):1051-6.

Hiatt et al., "Parallel, tag-directed assembly of locally derived short sequence reads," Nature Methods, 2010, 7(2):119-25.

Ho et al., "Bacteriophage T4 RNA ligase 2 (gp24.1) exemplifies a family of RNA ligases found in all phylogenetic domains," PNAS, Oct. 2002, 99(20):12709-14.

Ho et al., "Characterization of an ATP-Dependent DNA Ligase Encoded by Chlorella Virus PBCV-1," Journal of Virology, Mar. 1997, 71(3):1931-1937.

Hoffman et al., "Formaldehyde crosslinking: a tool for the study of chromatin complexes," J Biol Chem., Oct. 2015, 290(44):26404-11.

Hsuih et al., "Novel, Ligation-Dependent PCR Assay for Detection of Hepatitis C Virus in Serum," Journal of Clinical Microbiology, Mar. 1996, 34(3):501-507.

Hu et al., "High reproducibility using sodium hydroxide-stripped long oligonucleotide DNA microarrays," Biotechniques, Jan. 2005, 38(1):121-4.

Hughes et al., "Microfluidic Western blotting," PNAS, Dec. 2012, 109(52):21450-21455.

Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.

Ichikawa et al., "In vitro transposition of transposon Tn3," J Biol. Chem., Nov. 1990, 265(31):18829-32, Abstract.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Kap et al., "Histological assessment of PAXgene tissue fixation and stabilization reagents," PLoS One, 2011, 6:e27704, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells," Apr. 2019, 10(1):1930, 10 pages.

Ke et al., "In situ sequencing for RNA analysis in preserved tissue and cells," Nat Methods., Sep. 2013, Supplementary Materials, 29 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of Mycobacterium avium: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Kolovos et al., "Investigation of the spatial structure and interactions of the genome at sub-kilobasepair resolution using T2C," Nat. Protoc., 2018, 13:459-477.

Korbel et al., "Paired-end mapping reveals extensive structural variation in the human genome," Science, 2007, 318(5849):420-426.

Kozlov et al., "A highly scalable peptide-based assay system for proteomics," PLoS ONE, 2012, 7(6):e37441, 10 pages.

Kozlov et al., "A method for rapid protease substrate evaluation and optimization," Comb Chem High Throughput Screen, 2006, 9(6):481-87.

Kristensen et al., "High-Throughput Methods for Detection of Genetic Variation," BioTechniques, Feb. 2001, 30(2):318-332.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.

Kumar et al., "Template-directed oligonucleotide strand ligation, covalent intramolecular DNA circularization and catenation using click chemistry," J Am Chem Soc., May 2007, 129(21):6859-64.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmcogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lahiani et al., "Enabling Histopathological Annotations on Immunofluorescent Images through Virtualization of Hematoxylin and Eosin," J Pathol Inform., Feb. 2018, 9:1, 8 pages.

Lampe et al., "A purified mariner transposase is sufficient to mediate transposition in vitro," EMBO J., Oct. 1996, 15(19):5470-9.

Landegren et al., "Reading bits of genetic information: methods for single-nucleotide polymorphism analysis," Genome Res., Aug. 1998, 8(8):769-76.

Langdale et al., "A rapid method of gene detection using DNA bound to Sephacryl," Gene, 1985, 36(3):201-210.

Larman et al., "Sensitive, multiplex and direct quantification of RNA sequences using a modified RASL assay," Nucleic Acids Research, 2014, 42(14):9146-9157.

Lee et al., "Fluorescent in situ sequencing (FISSEQ) of RNA for gene expression profiling in intact cells and tissues," Nature Protocols, 2015, 10(3):442-458.

Lee et al., "Improving the efficiency of genomic loci capture using oligonucleotide arrays for high throughput resequencing," BMC Genomics, Dec. 2009, 10:646, 12 pages.

Leriche et al., "Cleavable linkers in chemical biology," Bioorganic & Medicinal Chemistry, 2012, 20:571-582.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lienemann et al., "Single cell-laden protease-sensitive microniches for long-term culture in 3D," Lab Chip, 2017, 17(4):727-737.

(56) References Cited

OTHER PUBLICATIONS

Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Martinez-Rivas et al., "Methods of Micropatterning and Manipulation of Cells for Biomedical Applications," Micromachines (Basel), Nov. 2017, 8(12):347, 20 pages.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.

Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.

(56) References Cited

OTHER PUBLICATIONS

PCT International Preliminary Report on Patentability in International Appln. No. PCT/EP2016/057355, dated Oct. 10, 2017, 7 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Preliminary Report on Patentability in International Appln. No. PCT/US2021/018795, dated Sep. 1, 2022, 10 pages.
PCT International Preliminary Report on Patentability in International Appln. No. PCT/US2021/018816, dated Sep. 1, 2022, 9 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
PCT International Search Report and Written Opinion in International Appln. No. PCT/US2022/028071, dated Aug. 25, 2022, 13 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.

Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Romero et al., "Protective Polymer Coatings for High-Throughput, High-Purity Cellular Isolation," ACS Applied materials and Interfaces, 2015, 17598-17602.
Romero et al., Supporting Information for "Protective Polymer Coatings for High-Throughput, High-Purity Cellular Isolation," 2015, S1-S14.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Sakai et al., "On-Cell Surface Cross-Linking of Polymer Molecules by Horseradish Peroxidase Anchored to Cell Membrane for Individual Cell Encapsulation in Hydrogel Sheath," ACS Macro Letters, 2014, 3:972-975.
Salmén et al., "Barcoded solid-phase RNA capture for Spatial Transcriptomics profiling in mammalian tissue sections," Nature Protocols, Oct. 2018, 13(11):2501-2534.
Salmen et al., "Multidimensional transcriptomics provides detailed information about immune cell distribution and identity in HER2+ breast tumors," bioRxiv, 2018, 41 pages.
Saxonov et al., "10x Genomics, Mastering Biology to Advance Human Health," PowerPoint, 10x, 2020, 41 pages.
Schaus et al., "A DNA nanoscope via auto-cycling proximity recording," Nat. Commun., 2017, 8:696, 10 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.

(56) References Cited

OTHER PUBLICATIONS

Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Söderberg et al., "Characterizing proteins and their interactions in cells and tissues using the in situ proximity ligation assay," Methods, Jul. 2008, 45(3):227-32.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spille et al., "Labelling and imaging of single endogenous messenger RNA particles in vivo," Journal of Cell Science, Oct. 2015, 128(20):3695-3706.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Taylor et al., "Mitochondrial DNA mutations in human disease," Nature Reviews Genetics, May 2005, 6(5):389-402.
Tegtmeyer et al., "Alternative Interactions of the SV40 A Protein with DNA," Virology, 1981, 115:75-87.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.

Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Van Vught et al., "Site-specific functionalization of proteins and their applications to therapeutic antibodies," Comput Struct Biotechnol J., Feb. 2014, 9:e201402001, 13 pages.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Veneziano et al., "Designer nanoscale DNA assemblies programmed from the top down," Science, Jun. 2016, 352(6293):1534, 10 pages.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Paramagnetic microspheres with core-shell-ed structures," Journal of Materials Science, Apr. 2012, 47(16):5946-54.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states," Science, Jul. 2018, 361(6400):eaat5691, 22 pages.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Weinstein et al., "DNA microscopy: Optics-free spatio-genetic imaging by a stand-alone chemical reaction", bioRxiv, 41 pages, 2018.

(56) References Cited

OTHER PUBLICATIONS

Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling, " PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
U.S. Appl. No. 63/033,348, filed Jun. 2, 2020, Bent.
Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.
Baner et al., "Signal amplification of padlock probes by rolling circle replication," Nucleic Acids Res., 1998, 26(22):5073-5078.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Codeluppi et al., "Spatial organization of the somatosensory cortex revealed by osmFISH," Nature Methods, Nov. 2018, 15:932-935.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Eng et al., "Transcriptome-scale super-resolved imaging in tissues by RNA seqFISH+," Nature, Apr. 2019, 568(7751):235-239, 37 pages.
Faruqi et al., "High-throughput genotyping of single nucleotide polymorphisms with rolling circle amplification," BMC Genomics, Aug. 2001, 2:4, 10 pages.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Goh et al., "Highly Specific Multiplexed RNA Imaging in Tissues With Split-FISH," Nat Methods, Jun. 15, 2020, 17(7):689-693, 21 pages.
Goransson et al., "A single molecule array for digital targeted molecular analyses," Nucleic Acids Res., Nov. 25, 2009, 37(1):e7, 9 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Mignardi et al., "Oligonucleotide gap-fill ligation for mutation detection and sequencing in situ," Nucleic Acids Research, Aug. 3, 2015, 43(22):e151, 12 pages.
Mohsen et al., "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Takei et al., "Integrated Spatial Genomics Reveals Global Architecture of Single Nuclei," Nature, Jan. 27, 2021, 590(7845):344-350, 53 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Ergin et al., "Proteomic Analysis of PAXgene-Fixed Tissues," J Proteome Res., 2010, 9(10):5188-96.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Xia et al., "Spatial transcriptome profiling by MERFISH reveals subcellular RNA compartmentalization and cell cycle-dependent

(56) References Cited

OTHER PUBLICATIONS gene expression", Proceedings of the National Academy of Sciences, Sep. 2019, 116(39):19490-19499.
Hobro et al, "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Schmidl et al., "ChIPmentation: fast, robust, low-input ChIP-seq for histones and transcription factors," Nature Methods, Oct. 2015, 12:963-965.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Chen et al. "Arrayed profiling of multiple glycans on whole living cell surfaces." Analytical chemistry, Oct. 15, 2013, 85(22):11153-11158.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): Jun. 24, 2013, 11 pages.
Su et al., "Restriction enzyme selection dictates detection range sensitivity in chromatin conformation capture-based variant-to-gene mapping approaches," bioRxiv, Dec. 15, 2020, 22 pages.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Marx, "Method of the Year: spatially resolved transcriptomics," Nature Methods, 2021, 18(1):9-14.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

\* cited by examiner

1. Prepare aqueous monomer solution acrylamide 3-aminopropyl methacrylamide sodium formate 5'-acrydite oligo 2. Generate linear polymers
VA-044 thermal initiated polymerization 3. Phenol-functionalize linear polymers
Couple phenol to aminopropyl side chains

THREE-DIMENSIONAL SPATIAL ANALYSIS

CROSS-REFERENCE TO RELATED APPLICATION

This application claims priority under 35 U.S.C. § 119(e) to U.S. Patent Application No. 63/082,150, filed on Sep. 23, 2020. The entire contents of this application are hereby incorporated by reference.

SEQUENCE LISTING

This application contains a Sequence Listing that has been submitted electronically as an ASCII text file named 47706-0243001_ST25.txt. The ASCII text file, created on Sep. 21, 2021, is 1006 bytes in size. The material in the ASCII text file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the contact of an intact tissue or a portion of a tissue, or provide a lot of analyte data for single cells, but fail to provide information regarding the position of the single cell in a parent biological sample (e.g., tissue sample).

The spatial organization of gene expression can be observed within a single cell, tissue, and organism. Genetic material and related gene and protein expression influences cellular fate and behavior. The spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, currently rely on a small set of pre-defined markers, therefore introducing selection bias that limits discovery and making it costly and laborious to localize RNA transcriptome-wide. Further, spatial organization often is performed on a two-dimensional sample. There remains a need to develop techniques that enhance three-dimensional detection of gene expression within a single cell, tissue, and organism.

SUMMARY

Three-dimensional detection of gene expression within a single cell, or tissue provides an additional dimension of spatial information of the specific position of a cell or expressed gene within a tissue. Spatially-programmed capture probes include a programmable migration domain that facilitates predetermined migration through a polymer matrix with high specificity. Contacting target analytes within a sample with the spatially-programmed capture probes and migrating the capture probes through the polymer matrix spatially differentiates the target analytes within a three-dimensional volume.

Spatially isolating the target analytes within the volume allows for increased detection and quantitation of the target analytes present in a sample. This facilitates higher overall accuracy of the genetic expression profile of a tissue sample.

Provided herein is a method for determining a location and abundance of an analyte in three-dimensional space in a biological sample, the method comprising: (a) immobilizing a biological sample on an array in a hydrogel matrix, wherein the hydrogel matrix includes a polymer; (b) providing a plurality of spatially-programmed capture probes, wherein a spatially-programmed capture probe in the plurality of spatially-programmed capture probes includes: (i) a programmable migration domain; (ii) a detectable moiety; and (iii) a capture domain that binds specifically to the analyte; (c) migrating the spatially-programmed capture probe into the hydrogel matrix from a point distal to a surface of the hydrogel matrix contacting the array; (d) hybridizing the spatially-programmed capture probe to the analyte, generating a hybridized spatially-programmed capture probe; (e) detecting the location of the detectable moiety in the hydrogel matrix, thereby determining a location of the spatially-programmed capture probe and/or analyte in the hydrogel matrix; (f) migrating the hybridized spatially-programmed capture probe to the array, wherein the array includes a plurality of capture probes, wherein a capture probe of the plurality of capture probes includes a spatial barcode and a capture domain that binds specifically to the hybridized spatially-programmed capture probe; and (g) determining (i) all or a part of a sequence in the hybridized spatially-programmed capture probe, or a complement thereof, (ii) all or a part of the sequence of the spatial barcode, or a complement thereof, and (iii) all or part of the sequence of the analyte, or a complement thereof, and using the determined sequences of (i), (ii), and (iii), and the determined location in (e), to identify the location and abundance of the analyte in the three-dimensional space in the biological sample.

In some embodiments, the polymer can include a moiety selected from the group consisting of a phenol moiety, an azide moiety, and an alkyne moiety. The polymer can include four monomers of polyethylene glycol and a plurality of phenol moieties, wherein a phenol moiety of the plurality of phenol moieties is affixed to each of the four monomers of polyethylene glycol. The polymer further can include a plurality of azide moieties, wherein an azide moiety of the plurality of azide moieties is affixed to each of the four monomers of polyethylene glycol. The polymer further can include a plurality of alkene moieties, wherein an alkene moiety of the plurality of alkene moieties is affixed to each of the four monomers of polyethylene glycol.

The method can further comprise extending a 3' end of the spatially-programmed capture probe prior to step (f). The spatially-programmed capture probe further can include a cleavage domain comprising a recognition sequence for a restriction endonuclease, wherein upon cleavage of the cleavage domain, the programmable migration domain is released from the spatially-programmed capture probe. The migrating the spatially-programmed capture probe is performed using active migration, wherein the active migration uses an electric field, a magnetic field, a charged gradient, or any combination thereof. Step (g) can include sequencing (i) all or a part of the sequence in the hybridized spatially-programmed capture probe that is not present in the spatially-programmed capture probe, or a complement thereof, (ii) all or a part of the sequence of the spatial barcode, or a complement thereof, and (iii) all or part of the sequence of the analyte, or a complement thereof.

In a second aspect, provided herein is a method for determining a location and abundance of a nucleic acid in a biological sample in a three dimensional space, the method comprising: (a) immobilizing a biological sample disposed on an array in a hydrogel matrix, wherein the hydrogel matrix comprises a polymer; (b) providing a plurality of pairs of spatially-programmed capture probes, wherein a pair of spatially-programmed capture probes in the plurality of pairs of spatially-programmed capture probes comprises a first spatially-programmed capture probe and a second spatially-programmed capture probe, wherein: at least one of the first and the second spatially-programmed capture probe comprises a detectable moiety; the first spatially-programmed capture probe and the second spatially-programmed capture probe, when hybridized to the nucleic acid, are capable of being ligated together; and each of the first spatially-programmed capture probe and the second spatially-programmed capture probe comprise a programmable migration domain, (c) migrating the pair of spatially-programmed capture probes into the hydrogel matrix from a surface of the hydrogel matrix that is distal to the surface of the hydrogel matrix contacting the array; (d) hybridizing the first spatially-programmed capture probe and the second spatially-programmed capture probe to the nucleic acid; (e) ligating the first spatially-programmed capture probe and the second spatially-programmed capture probes to generate a ligation product; (f) detecting a location of detectable moiety in the hydrogel matrix, thereby determining a location of the ligation product in the hydrogel matrix; (g) migrating the ligation product to the array, wherein the array comprises a plurality of capture probes, wherein a capture probe of the plurality of capture probes comprises a spatial barcode and a capture domain that binds specifically to a sequence in the ligation product; and (h) determining (i) all or a part of the sequence of the ligation product, or a complement thereof, and (ii) all or a part of the sequence of the spatial barcode, or a complement thereof, and using the determined sequences of (i) and (ii), and the determined location in (f), to identify a three-dimensional location of the nucleic acid in the biological sample.

In some embodiments, the polymer can include a moiety from the group consisting of a phenol moiety, an azide moiety, and an alkyne moiety. The polymer can include four monomers of polyethylene glycol, and a plurality of phenol moieties, wherein a phenol moiety of the plurality is affixed to each of the four monomers of polyethylene glycol. The polymer further can include a plurality of azide moieties, wherein an azide moiety of the plurality is affixed to each of the four monomers of polyethylene glycol. The polymer further can include a plurality of alkene moieties, wherein an alkene moiety of the plurality is affixed to each of the four monomers of polyethylene glycol. The first spatially-programmed capture probe further can include a cleavage domain, wherein upon cleavage of the cleavage domain, the programmable migration domain is released from the first spatially-programmed capture probe; and/or the second spatially-programmed capture probe further can include a cleavage domain, wherein upon cleavage of the cleavage domain, the programmable migration domain is released from the second spatially-programmed capture probe.

The migrating of the pair of spatially-programmed capture probes is performed using active migration, wherein the active migration uses an electric field, a magnetic field, a charged gradient, or any combination thereof. Step (h) can include sequencing (i) all or a part of the sequence in the single-stranded ligation product, or a complement thereof, and (ii) all or a part of the sequence of the spatial barcode, or a complement thereof. The detecting of the detectable moiety in step (f) can include imaging the biological sample using confocal microscopy, and wherein the imaging identifies a region of interest in the biological sample. The programmable migration domain can include a polyethylene glycol, a folded three-dimensional oligonucleotide domain, a charged domain, a protein domain, a size-specific domain, an electromagnetic domain, or any combination thereof. The detectable moiety can include one or more fluorescent labels, or one or more heavy metals.

Provided herein are methods for determining a location of an analyte in three-dimensional space in a biological sample, including: (a) immobilizing a biological sample disposed on the array in a hydrogel matrix, wherein the hydrogel matrix includes a polymer; (b) providing a plurality of spatially-programmed capture probes, wherein a spatially-programmed capture probe in the plurality of spatially-programmed capture probes includes: (i) a programmable migration domain; (ii) a detectable moiety; and (iii) a capture domain that binds specifically to the analyte; (c) migrating the spatially-programmed capture probe into the hydrogel matrix from a point distal to the hydrogel matrix contacting the array; (d) hybridizing the spatially-programmed capture probe to the analyte, generating a hybridized spatially-programmed capture probe; (e) detecting the location of detectable moiety in the hydrogel matrix, thereby determining a location of the spatially-programmed capture probe and/or analyte in the hydrogel matrix; (f) migrating the hybridized spatially-programmed capture probe to the array, wherein the array includes a plurality of capture probes, wherein a capture probe of the plurality of capture probes includes a spatial barcode and a capture domain that binds specifically to a sequence in the hybridized spatially-programmed capture probe that is not present in the spatially-programmed capture probe; and (g) determining (i) all or a part of the sequence in the hybridized spatially-programmed capture probe, or a complement thereof, and (ii) all or a part of the sequence of the spatial barcode, or a complement thereof, and using the determined sequences of (i) and (ii), and the determined location in (e), to identify the analyte in the three-dimensional space in the biological sample.

In some embodiments, the polymer includes a moiety from the group consisting of a phenol moiety, an azide moiety or an alkyne moiety. In some embodiments, the polymer includes polyethylene glycol. In some embodiments, the polymer includes monomers of polyethylene glycol. In some embodiments, the polymer includes four monomers of polyethylene glycol. In some embodiments, the polymer further including a plurality of phenol moieties, wherein a phenol moiety of the plurality is affixed to each of the four monomers of polyethylene glycol. In some embodiments, the polymer further including a plurality of azide moieties, wherein an azide moiety of the plurality is affixed to each of the four monomers of polyethylene glycol. In some embodiments, the polymer further including a plurality of alkene moieties, wherein an alkene moiety of the plurality is affixed to each of the four monomers of polyethylene glycol.

In some embodiments, the method further includes a step of permeabilizing the biological sample.

In some embodiments, step (f) includes extending a 3' end of the spatially-programmed capture probe. In some embodiments, the spatially-programmed capture probe further includes a cleavage domain, wherein upon cleavage of the cleavage domain, the programmable migration domain is released from the spatially-programmed capture probe.

In some embodiments, the method further includes, between steps (f) and (g), cleaving the cleavage domain to release the programmable migration domain from the spatially-programmed capture probe. In some embodiments, the cleavage domain includes a recognition sequence for a restriction endonuclease.

In some embodiments of any of the methods described herein, the spatially-programmed capture probe is an oligonucleotide probe. In some embodiments of any of the methods described herein, the capture domain in the spatially-programmed capture probe includes an oligo(dT) sequence. In some embodiments of any of the methods described herein, the migrating of the spatially-programmed capture probe is performed using passive migration. In some embodiments of any of the methods described herein, wherein the migrating of the spatially-programmed capture probe is performed using active migration. In some embodiments, the active migration uses an electric field, a magnetic field, a charged gradient, or any combination thereof. In some embodiments of any of the methods described herein, the migrating of the spatially-programmed capture probe is performed in a linear direction. In some embodiments of any of the methods described herein, the migrating of the spatially-programmed capture probe is performed in a non-linear direction.

In some embodiments of any of the methods described herein step (g) includes sequencing (i) all or a part of the sequence in the hybridized spatially-programmed capture probe that is not present in the spatially-programmed capture probe, or a complement thereof, and (ii) all or a part of the sequence of the spatial barcode, or a complement thereof. In some embodiments, the sequencing is performed using sequencing-by-synthesis, sequential fluorescence hybridization, sequencing by ligation, sequencing by hybridization, or high-throughput digital sequencing techniques. In some embodiments, the sequencing is performed using sequencing by synthesis.

In some embodiments of any of the methods described herein, the detecting of the detectable moiety in step (e) includes imaging the permeabilized biological sample. In some embodiments, the imaging is performed using confocal microscopy. In some embodiments, the imaging is further used to identify a region of interest in the permeabilized biological sample. In some embodiments, the imaging includes using fiducial markers.

Also provided herein are methods for determining the location of a nucleic acid in a biological sample in a three dimensional space, including: (a) immobilizing a biological sample disposed on the array in a hydrogel matrix, wherein the hydrogel matrix includes a polymer including a moiety selected from the group consisting of a phenol moiety, an azide moiety, and an alkyne moiety; (b) providing a plurality of pairs of spatially-programmed capture probes, wherein a pair of spatially-programmed capture probes in the plurality of pairs of spatially-programmed capture probes includes a first and a second spatially-programmed capture probe, wherein: at least one of the first and the second spatially-programmed capture probe includes a detectable moiety; the first and the second spatially-programmed capture probe, when hybridized to the nucleic acid, are capable of being ligated together; and each of the first and the second spatially-programmed capture probes include a programmable migration domain, (c) migrating the pair of spatially-programmed capture probes into the hydrogel matrix from a surface of the hydrogel matrix that is distal to the surface of the hydrogel matrix contacting the array; (d) ligating the first and the second spatially-programmed capture probes, when hybridized to the nucleic acid, to generate a ligation product; (e) detecting the location of detectable moiety in the hydrogel matrix, thereby determining a location of the ligation product in the hydrogel matrix; (f) migrating the ligation product to the array, wherein the array includes a plurality of capture probes, wherein a capture probe of the plurality of capture probes includes a spatial barcode and a capture domain that binds specifically to a sequence in the ligation product; and (g) determining (i) all or a part of the sequence in the ligation product, or a complement thereof, and (ii) all or a part of the sequence of the spatial barcode, or a complement thereof, and using the determined sequences of (i) and (ii), and the determined distance in (e), to identify the three-dimensional location of the nucleic acid in the biological sample.

In some embodiments, the polymer includes a moiety from the group consisting of a phenol moiety, an azide moiety or an alkyne moiety. In some embodiments, the polymer includes polyethylene glycol. In some embodiments, the polymer includes monomers of polyethylene glycol. In some embodiments, the polymer includes four monomers of polyethylene glycol. In some embodiments, the polymer further including a plurality of phenol moieties, wherein a phenol moiety of the plurality is affixed to each of the four monomers of polyethylene glycol. In some embodiments, the polymer further including a plurality of azide moieties, wherein an azide moiety of the plurality is affixed to each of the four monomers of polyethylene glycol. In some embodiments, the polymer further including a plurality of alkene moieties, wherein an alkene moiety of the plurality is affixed to each of the four monomers of polyethylene glycol.

In some embodiments, the method further including a step of permeabilizing the biological sample.

In some embodiments of any of the methods described herein the capture domain binds specifically to a sequence in the ligation product including at least one nucleotide 5' and at least one nucleotide 3' to a site of ligation in the single-stranded ligation product.

In some embodiments of any of the methods described herein, wherein the first spatially-programmed capture probe further includes a cleavage domain, wherein upon cleavage of the cleavage domain, the programmable migration domain is released from the first spatially-programmed capture probe. In some embodiments, the method further includes, between steps (d) and (e), cleaving the cleavage domain to release the programmable migration domain from the first spatially-programmed capture probe. In some embodiments, the second spatially-programmed capture probe further includes a cleavage domain, wherein upon cleavage of the cleavage domain, the programmable migration domain is released from the second spatially-programmed capture probe. In some embodiments, the method further includes, between steps (d) and (e), cleaving the cleavage domain to release the programmable migration domain from the second spatially-programmed capture probe.

In some embodiments of any of the methods described herein wherein: the first spatially-programmed capture probe further includes a cleavage domain, wherein upon cleavage of the cleavage domain, the programmable migration domain is released from the first spatially-programmed capture probe; and the second spatially-programmed capture probe further includes a cleavage domain, wherein upon cleavage of the cleavage domain, the programmable migration domain is released from the second spatially-programmed capture probe.

In some embodiments of any of the methods described herein the method further includes, between steps (d) and (e)

cleaving the cleavage domain to release the programmable migration domain from the first and second spatially-programmed capture probes. In some embodiments, the cleavage domain includes a recognition sequence for a restriction endonuclease. In some embodiments, the first and second spatially-programmed capture probes are oligonucleotide probes.

In some embodiments, the migrating of the pair of spatially-programmed capture probes is performed using passive migration. In some embodiments, the migrating of the pair of spatially-programmed capture probes is performed using active migration. In some embodiments, the active migration uses an electric field, a magnetic field, a charged gradient, or any combination thereof. In some embodiments, the migrating of the pair of spatially-programmed capture probes is performed in a linear direction. In some embodiments, the migrating of the spatially-programmed capture probe is performed in a non-linear direction.

In some embodiments of any of the methods described herein, step (g) further includes sequencing (i) all or a part of the sequence in the single-stranded ligation product, or a complement thereof, and (ii) all or a part of the sequence of the spatial barcode, or a complement thereof. In some embodiments, the sequencing is performed using sequencing-by-synthesis, sequential fluorescence hybridization, sequencing by ligation, nucleic acid hybridization, or high-throughput digital sequencing techniques. In some embodiments, the sequencing is performed using sequencing by synthesis.

In some embodiments of any of the methods described herein, the detecting of the detectable moiety in step (e) includes imaging the permeabilized biological sample. In some embodiments, the imaging is performed using confocal microscopy. In some embodiments, the imaging is further used to identify a region of interest in the permeabilized biological sample. In some embodiments, the imaging includes using fiducial markers.

In some embodiments of any of the methods described herein, the permeabilized biological sample is a tissue sample. In some embodiments, the tissue sample is a tissue section. In some embodiments, the tissue sample is a fresh-frozen tissue sample. In some embodiments, the tissue sample includes a tumor cell.

In some embodiments of any of the methods described herein, the nucleic acid is RNA. In some embodiments, the RNA is mRNA. In some embodiments, the nucleic acid is DNA. In some embodiments of any of the methods described herein, the nucleic acid is immobilized in the hydrogel matrix. In some embodiments, the nucleic acid is immobilized in the hydrogel matrix by cross-linking.

In some embodiments of any of the methods described herein, the programmable migration domain includes a charged domain, a size-specific domain, an electromagnetic domain, or any combination thereof. In some embodiments of any of the methods described herein, the programmable migration domain includes a folded oligonucleotide domain. In some embodiments, the folded oligonucleotide domain is a folded three-dimensional oligonucleotide domain. In some embodiments of any of the methods described herein, the programmable migration domain includes a protein domain. In some embodiments, the protein domain includes multiple subunits. In some embodiments, the protein domain includes biotin, avidin, or streptavidin. In some embodiments of any of the methods described herein, the programmable migration domain includes a polyethylene glycol. In some embodiments, the detectable moiety includes one or more fluorescent labels. In some embodiments of any of the methods described herein, the detectable moiety includes one or more heavy metals.

In some embodiments of any of the methods described herein, the method further including performing a proximity capture reaction of one or more nucleic acid in the permeabilized biological sample, wherein the one or more nucleic acid are proximal or adjacent to one another in the permeabilized biological sample, and wherein the proximity capture reaction generates a plurality of proximally-associated nucleic acid pairs. In some embodiments, the method further including determining the identities of the proximal-associated nucleic acid pairs.

In some embodiments, the proximity capture reaction is performed before migrating the spatially-programmed capture probe(s) into the hydrogel matrix. In some embodiments, the proximity capture reaction includes proximity ligation. In some embodiments, the proximity capture reaction is irreversible. In some embodiments, the proximity capture reaction is reversible. In some embodiments, the proximity capture reaction is performed on nucleic acid within about 250 nm of each other. In some embodiments, the proximity capture reaction is performed on nucleic acid within about 100 nm of each other. In some embodiments, the proximity capture reaction is performed on nucleic acid within about 40 nm of each other.

Also provided herein is a method for delivering a spatially-programmed capture probe to a permeabilized biological sample including: (a) immobilizing the permeabilized biological sample disposed on an array in a hydrogel matrix; (b) providing a plurality of spatially-programmed capture probes, wherein a spatially-programmed capture probe in the plurality of spatially-programmed capture probes includes: (i) a programmable migration domain; (ii) a detectable moiety; and (iii) a capture domain that binds specifically to a sequence within a nucleic acid in the permeabilized biological sample; and (c) migrating the spatially-programmed capture probe into the hydrogel matrix from a surface of the hydrogel matrix that is distal to a surface of the hydrogel matrix contacting the array.

Also provided herein is a method for delivering a pair of spatially-programmed capture probes to a permeabilized biological sample including: (a) immobilizing the permeabilized biological sample disposed on an array in a hydrogel matrix; (b) providing a plurality of pairs of spatially-programmed capture probes, wherein a pair of spatially-programmed capture probes in the plurality of pairs of spatially-programmed capture probes includes a first and a second spatially-programmed capture probe, wherein: at least one of the first and the second spatially-programmed capture probe includes a detectable moiety; the first and the second spatially-programmed capture probe, when hybridized to a nucleic acid analyte in the biological sample, are capable of being ligated together; and each of the first and the second spatially-programmed capture probes include a programmable migration domain, and (c) migrating the pair of spatially-programmed capture probes into the hydrogel matrix from a surface of the hydrogel matrix that is distal to a surface of the hydrogel matrix contacting the array.

Also provided herein is a spatially-programmed capture probe including: (i) a programmable migration domain; (ii) a detectable moiety; and (iii) a capture domain that binds specifically to a sequence within a nucleic acid.

Also provided herein is a pair of spatially-programmed capture probes including a first and a second spatially-programmed capture probe, wherein: at least one of the first and the second spatially-programmed capture probe includes a detectable moiety; the first and the second spatially-programmed capture probe, when hybridized to a nucleic acid, are capable of being ligated together; and each of the first and the second spatially-programmed capture probes include a programmable migration domain.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
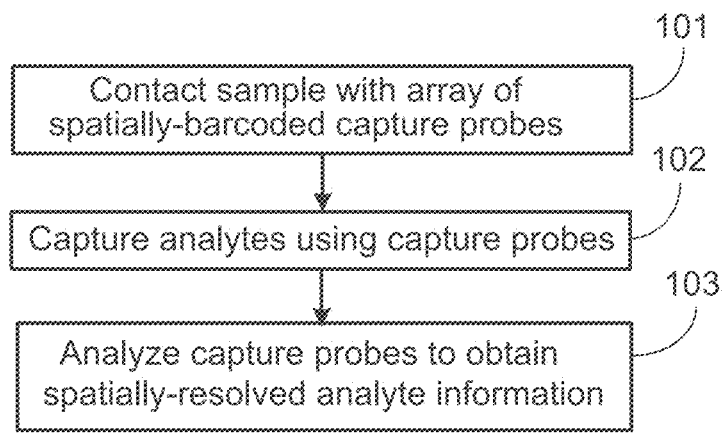
FIG. 1 shows an exemplary spatial analysis workflow.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774, 374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe.

In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication No. 2021/0140982A1, U.S. Patent Application No. 2021/0198741A1, and/or U.S. Patent Application No. 2021/0199660.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections *Control Slide for Imaging, Methods of Using Control Slides and Substrates for, Systems of Using Control Slides and Substrates for Imaging, and/or Sample and Array Alignment Devices and Methods, Informational labels* of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in WO 2021/102003 and/or U.S. patent application Ser. No. 16/951,854, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2021/102039 and/or U.S. patent application Ser. No. 16/951,864, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, *Control Slide for Imaging* Section of WO 2020/123320, WO 2021/102005, and/or U.S. patent application Ser. No. 16/951,843, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to promote analytes out of a cell and towards the spatially-barcoded array. FIG. 1 depicts an exemplary embodiment of this general method. In FIG. 1, the spatially-barcoded array populated with capture probes (as described further herein) is contacted with a biological sample 101, and biological sample is permeabilized, allowing the analyte to migrate away from the sample and toward the array. The analyte interacts with a capture probe on the spatially-barcoded array 102. Once the analyte hybridizes/is bound to the capture probe, the sample is optionally removed from the array and the capture probes are analyzed in order to obtain spatially-resolved analyte information 103.

Figure 2:
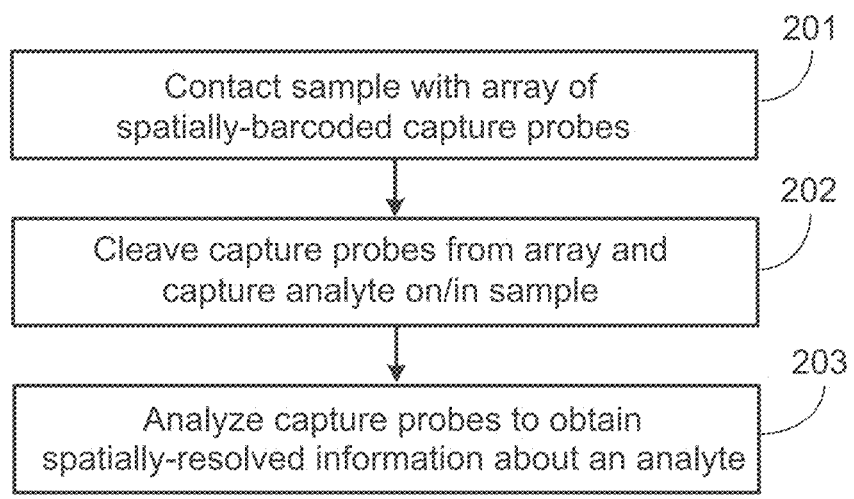
FIG. 2 shows an exemplary spatial analysis workflow.

Another general method is to cleave the spatially-barcoded capture probes from an array, and promote the spatially-barcoded capture probes towards and/or into or onto the biological sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided biological sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 3:
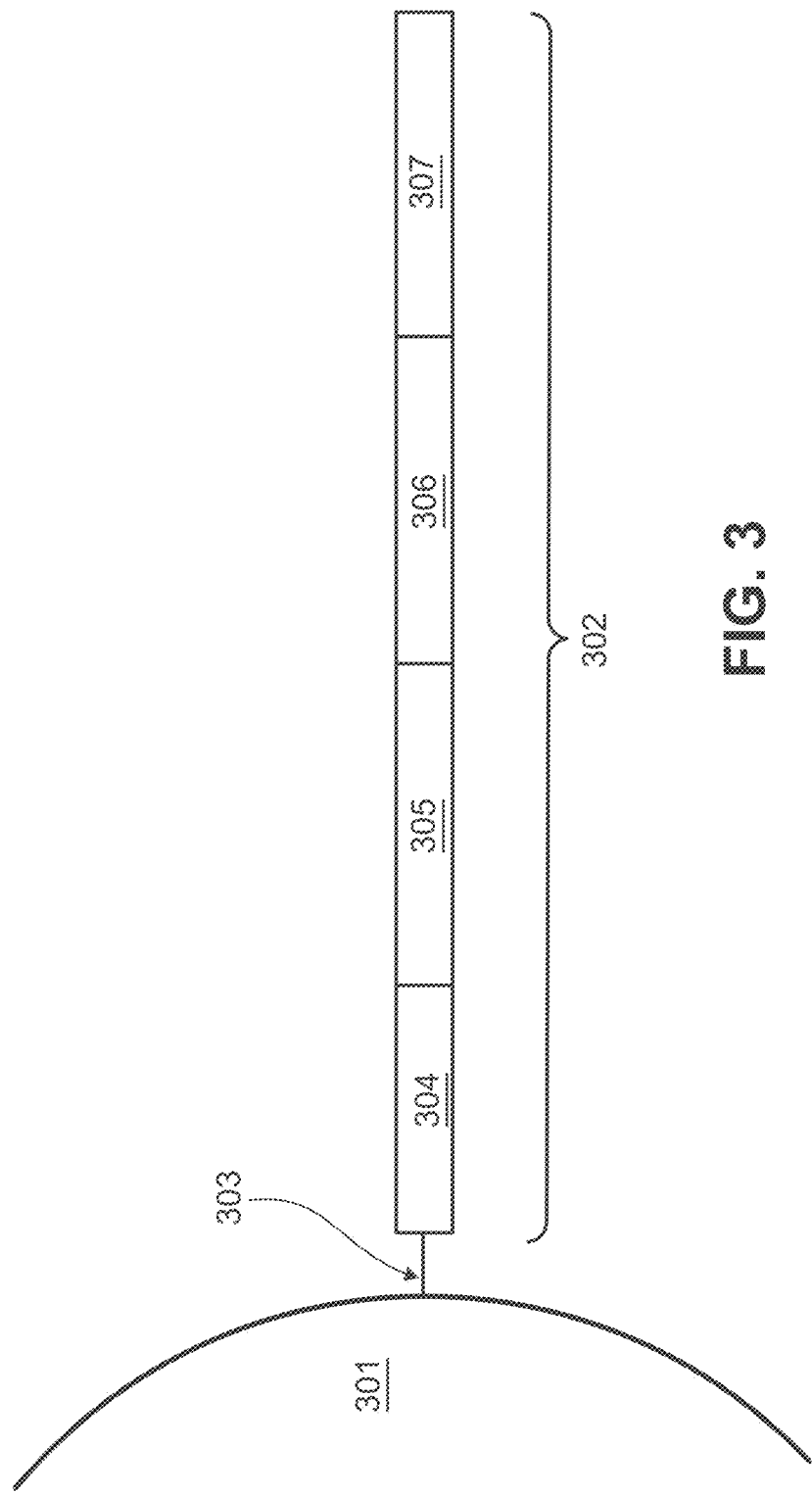
FIG. 3 is a schematic diagram showing an example of a barcoded capture probe, as described herein.

FIG. 3 is a schematic diagram showing an example of a capture probe, as described herein. As shown, the capture probe 302 is optionally coupled to a feature 301 by a cleavage domain 303, such as a disulfide linker. The capture probe can include functional sequences that are useful for subsequent processing, such as functional sequence 304, which can include a sequencer specific flow cell attachment sequence, e.g., a P5 or P7 sequence, as well as functional sequence 306, which can include sequencing primer sequences, e.g., a R1 primer binding site, a R2 primer binding site. In some embodiments, sequence 304 is a P7 sequence and sequence 306 is a R2 primer binding site. A spatial barcode 305 can be included within the capture probe for use in barcoding the target analyte. The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 305, functional sequences 304 (e.g., flow cell attachment sequence) and 306 (e.g., sequencing primer sequences) can be common to all of the probes attached to a given feature. The spatial barcode can also include a capture domain 307 to facilitate capture of a target analyte.

Each capture probe can optionally include at least one cleavage domain. The cleavage domain represents the portion of the probe that is used to reversibly attach the probe to an array feature, as will be described further herein. Further, one or more segments or regions of the capture probe can optionally be released from the array feature by cleavage of the cleavage domain. As an example, spatial barcodes and/or universal molecular identifiers (UMIs) can be released by cleavage of the cleavage domain.

Figure 4:
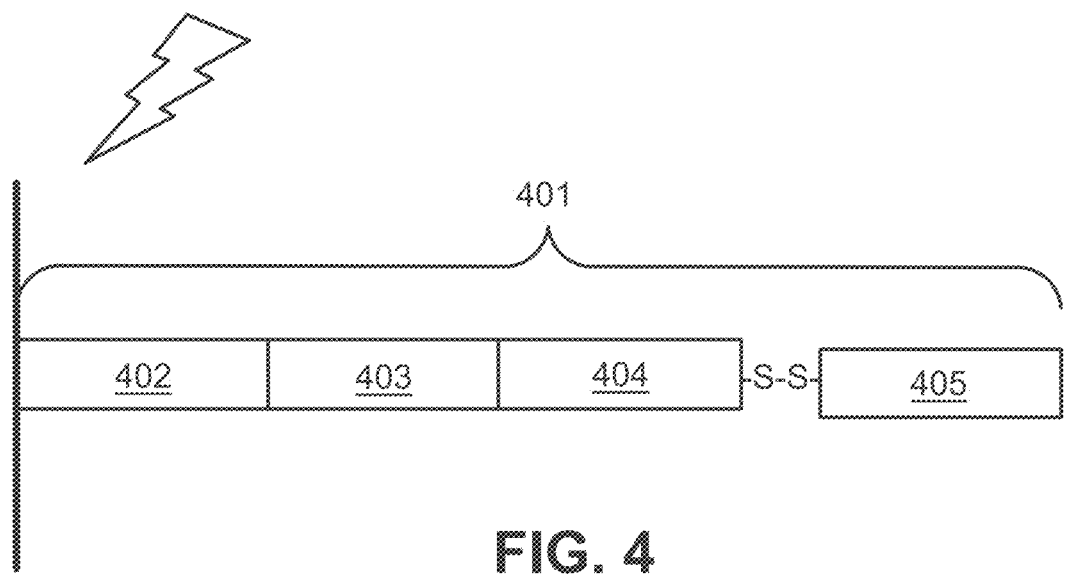
FIG. 4 is a schematic illustrating a cleavable capture probe, wherein the cleaved capture probe can enter into a non-permeabilized cell and bind to target analytes within the sample.

FIG. 4 is a schematic illustrating a cleavable capture probe, wherein the cleaved capture probe can enter into a non-permeabilized cell and bind to analytes within the sample. The capture probe 401 contains a cleavage domain 402, a cell penetrating peptide 403, a reporter molecule 404, and a disulfide bond (—S—S—). 405 represents all other parts of a capture probe, for example a spatial barcode and a capture domain.

Figures 5A, 5B, 5C, 5D, 5E, 5F, 5G:
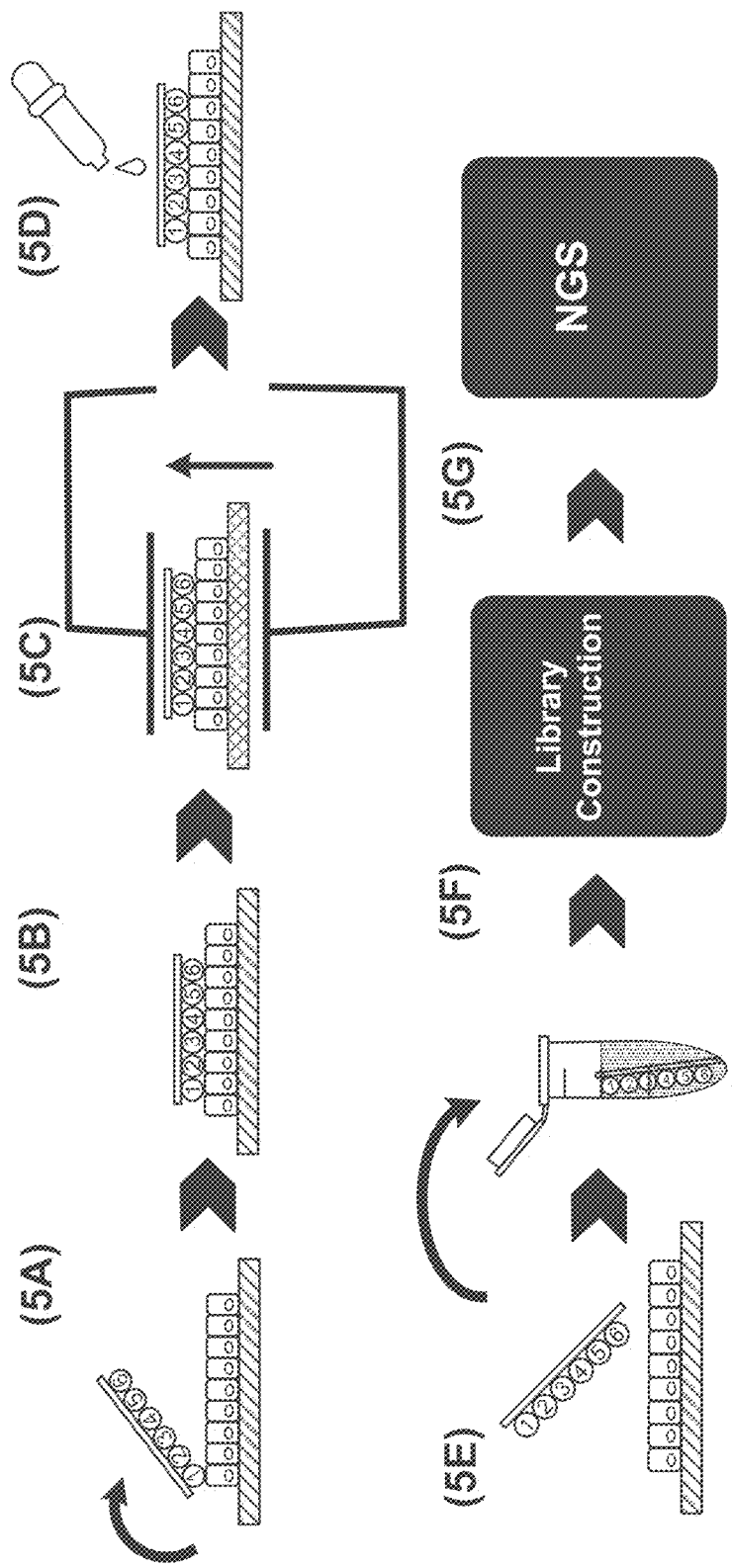
FIGS. 5A-5G show a schematic illustrating an exemplary workflow utilizing an electrophoretic transfer system.

FIGS. 5A-5G is an illustration showing an exemplary workflow protocol utilizing an electrophoretic transfer system. In the example, FIG. 5A depicts a flexible spatially-barcoded feature array being contacted with a sample. The sample can be a flexible array, wherein the array is immobilized on a hydrogel, membrane, or other flexible substrate. FIG. 5B depicts contact of the array with the sample and imaging of the array-sample assembly. The image of the sample/array assembly can be used to verify sample placement, choose a region of interest, or any other reason for imaging a sample on an array as described herein. FIG. 5C depicts application of an electric field using an electrophoretic transfer system to aid in efficient capture of a target analyte. Here, negatively charged mRNA target analytes migrate toward the positively charged anode. FIG. 5D depicts application of reverse transcription reagents and first strand cDNA synthesis of the captured target analytes. FIG. 5E depicts array removal and preparation for library construction (FIG. 5F) and next-generation sequencing (FIG. 5G).

A "proximity capture reaction" as used herein refers to a reaction that detects two analytes that are spatially close to each other and/or interacting with each other. For example, a proximity capture reaction can be used to detect sequences of DNA that are close in space to each other, e.g., the DNA sequences may be within the same chromosome, but separated by about 700 bp or less. As another example, a proximity capture reaction can be used to detect protein associations, e.g., two proteins that interact with each other. A proximity capture reaction can be performed in situ to detect two analytes (e.g., DNA and a protein, or RNA and a protein) that are spatially close to each other and/or interacting with each other inside a cell. For example, a proximity capture reaction can be used to detect nucleic acid-protein associations, e.g., where one analyte is a DNA or RNA molecule and one analyte is a protein.

Figure 11:
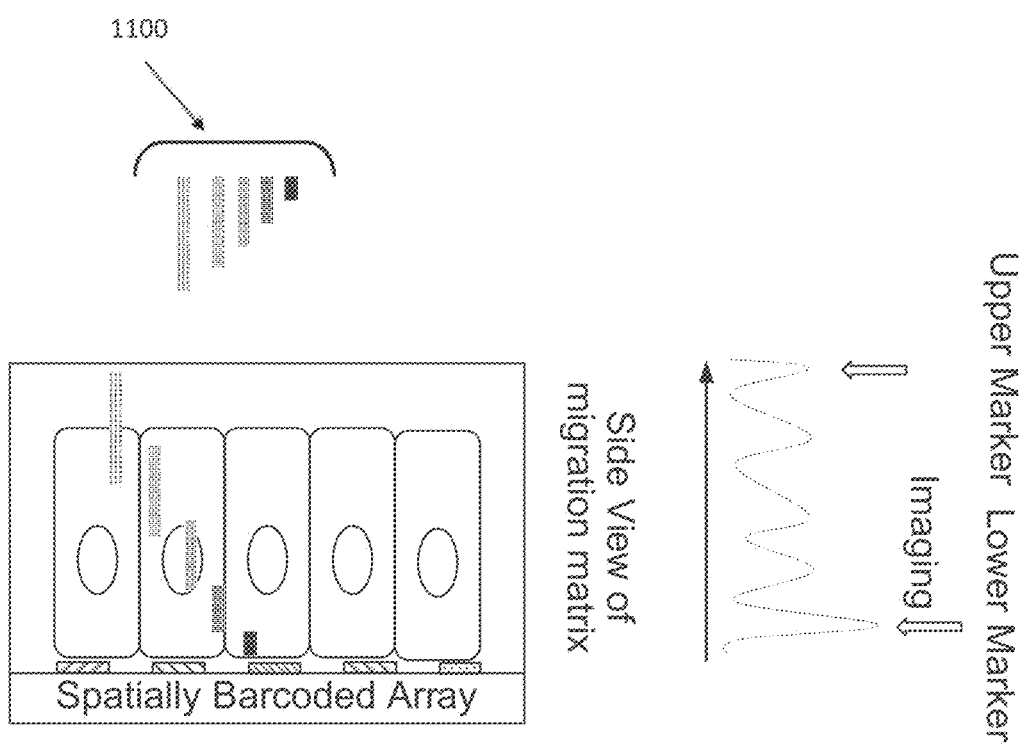
FIG. 11 shows an exemplary process of determining the migration position of the z-dimensional spatially programmed capture probes through imaging and thereby associating the capture probe barcode with the migration position. Upper and lower markers can be used to determine the migration limit of the z-dimensional capture probes.
Figure 12:
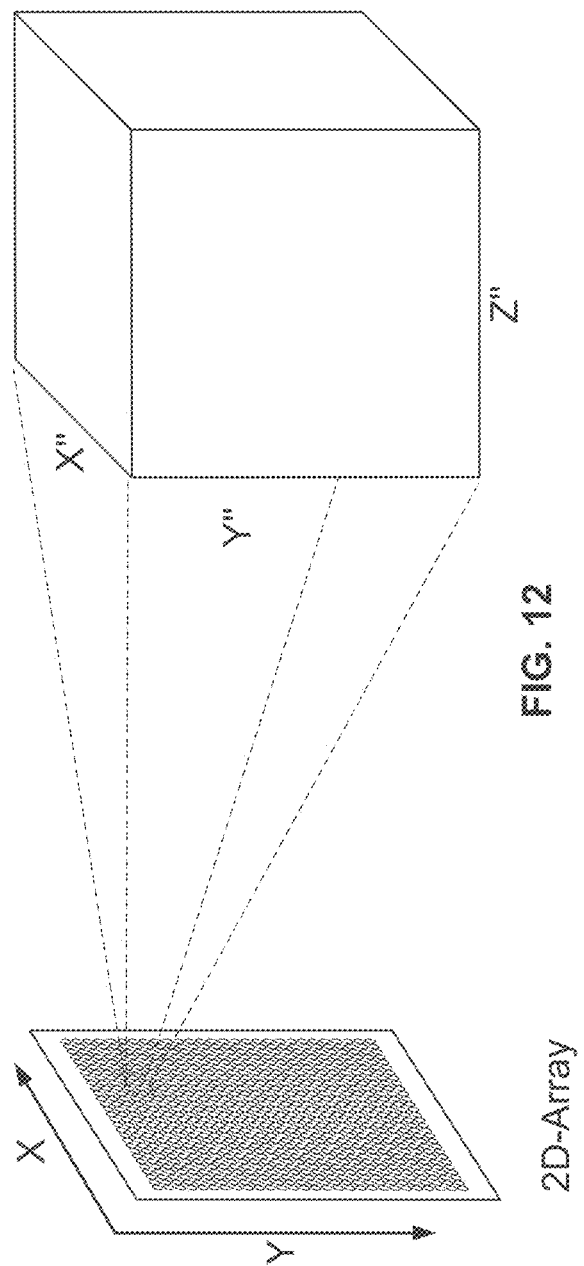
FIG. 12 is a schematic showing how a 2D array can be used to generate a 3D reconstruction of subcellular geometries at each voxel. The scales of x and y are in millimeters (mm), and the scales of X", Y", and Z" are in nanometers (nm).

In some embodiments, a proximity capture reaction(s) as disclosed herein is used to increase effective resolution of three-dimensional analyte detection. FIG. 12 is a schematic showing how a 2D array can be used in 3D reconstruction of subcellular geometries at each voxel. The scales of x and y are in mm, and the scales of X", Y", and Z" are in nm. As shown in exemplary FIGS. 10-12, use of proximity capture reaction(s) in combination with a 2-dimensional spatial array can be used to increase the resolution of three-dimensional analyte detection. A proximity capture reaction (s) can be used bind or otherwise associate analytes that are proximal to each other in a biological sample to generate proximally-associated biological analyte pairs prior to capture of the proximally-associated biological analyte pairs on a 2-dimensional spatial array. In some embodiments, by analyzing the various proximally-associated biological analyte pairs, a 3-dimensional map of the analytes can be reconstructed, and the effective resolution of the three-dimensional analyte reconstruction is increased beyond the resolution of the 2-dimensional array used in the analysis.

Figure 15A:
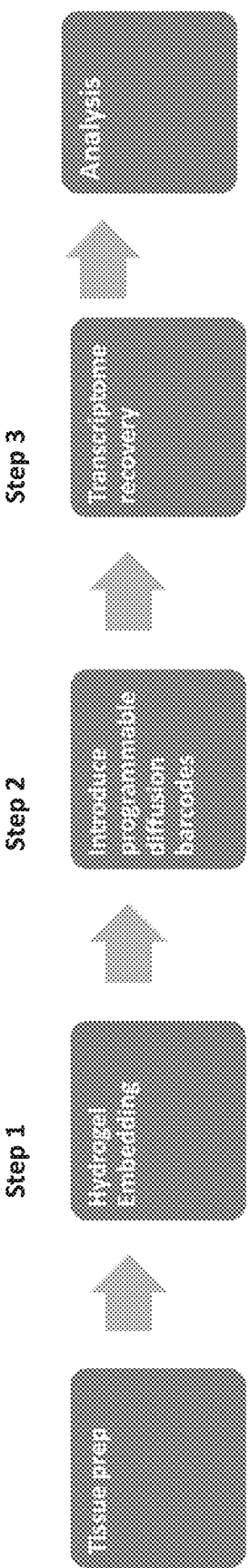
FIG. 15A is a schematic overview of the methods disclosed herein.

I. Three-Dimensional Spatial Analysis Using Hydrogels (a) Introduction: Methods for Spatial Profiling using Spatially-Programmed Capture Probes and Hydrogels The present application discloses compositions and methods relating to three-dimensional analysis of analytes in a biological sample. The technique disclosed herein relies on three general steps, as shown in FIG. 15A. First, a biological sample of interest (e.g., a tissue) is embedded into a hydrogel matrix (or hydrogel), locking one or more analytes in three-dimensional space. Spatially-programmed capture probes are introduced to the sample. The spatially-programmed capture probes migrate along a first dimension (e.g., a z-dimension) of the biological sample and molecularly "tag" distinct layers in the tissue along the first dimension. After migration, the spatially-programmed capture probes detect one or more analytes of interest by hybridizing (e.g., specifically binding) to the analyte at the specific layer (e.g., location in the z-dimension) in the tissue. The location of the spatially-programmed capture probes is determined. Finally, the spatially-programmed capture probes hybridized to the analyte of interest migrate through the sample and are captured on a two-dimensional (e.g., x-y dimensions) array that comprises capture probes with capture domains that specifically bind to the spatially-programmed capture probes.

Figure 6:
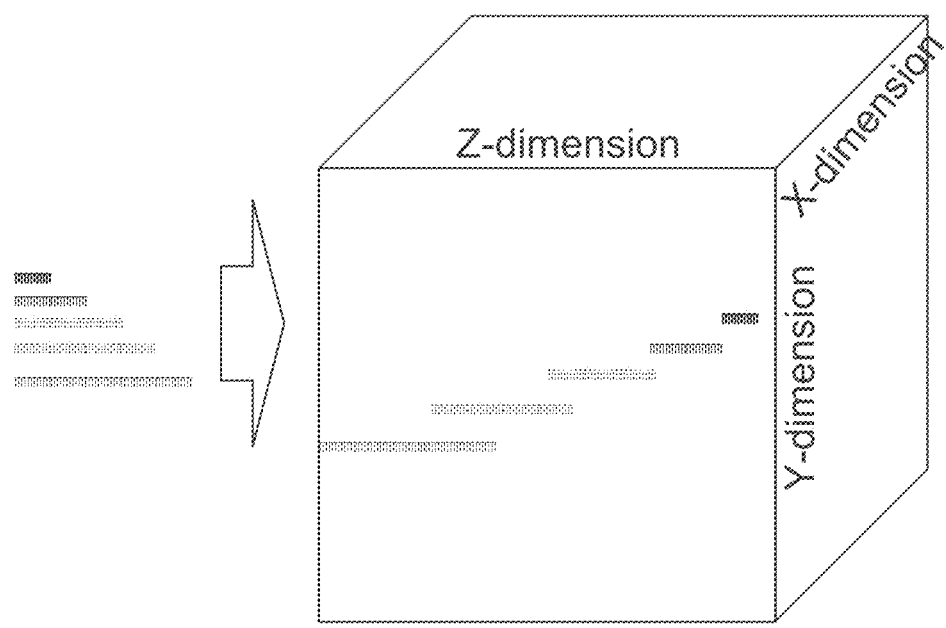
FIG. 6 is a schematic showing the different migration of different lengths of spatially-programmed capture probes in a three-dimensional matrix.
Figure 7:
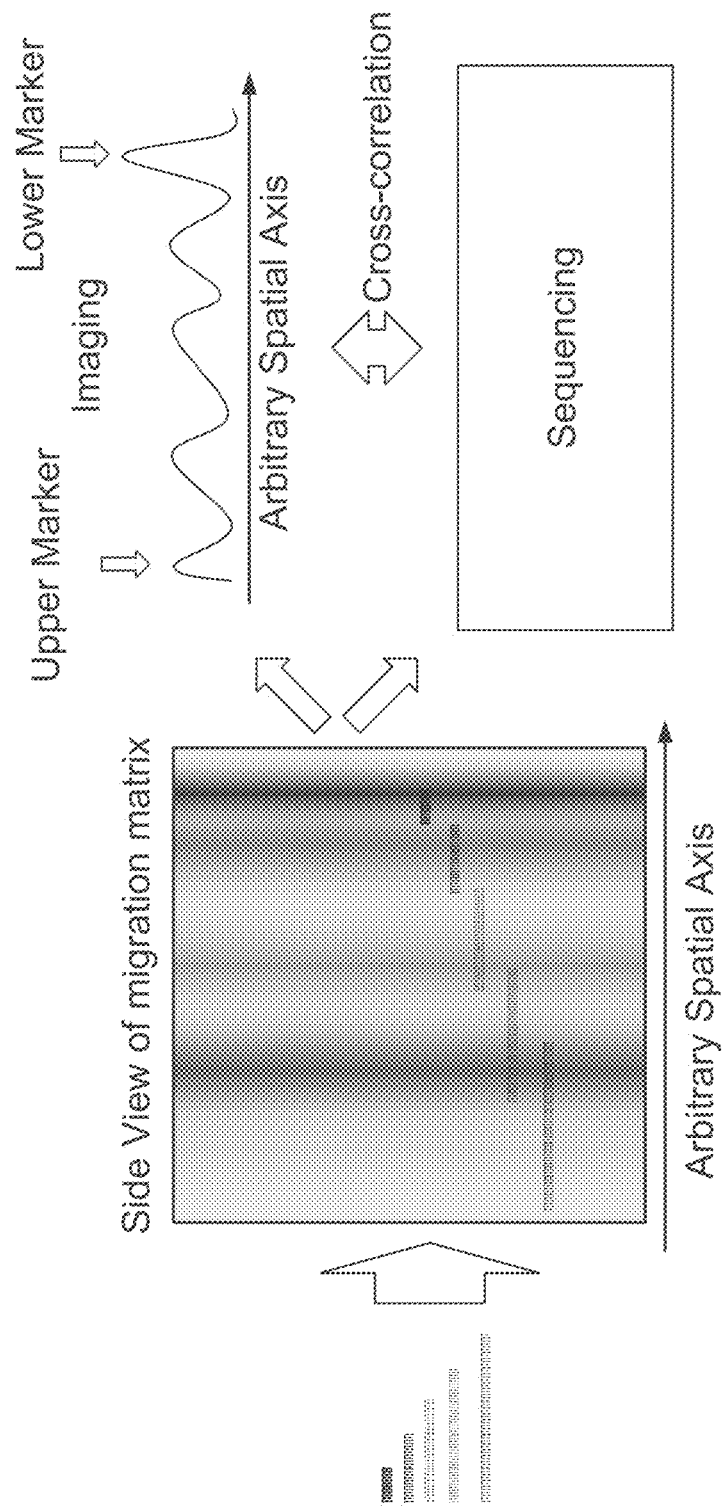
FIG. 7 is a schematic showing an exemplary method of deconvolving spatial positions based on migration of spatially programmed capture probes. As an example, spatially-programmed capture probes of different lengths, where each length comprises a marker different from the markers of other lengths, are allowed to migrate through a matrix. The spatially-programmed capture probes migrate different distances depending on their length. The spatially-programmed capture probes can be imaged and the different markers identified, thus allowing the spatial location of the spatially-programmed capture probes to be determined. After a plurality of spatially-programmed capture probes are contacted with a plurality of biological analytes, sequencing can be used in combination with the imaging data to associate a biological analyte of interest from the plurality of biological analytes to a spatially-programmed capture probe and a spatial location.

It is appreciated that the spatially-programmed capture probes allow for the analysis of the spatial location of an analyte in a third dimension (e.g., in addition to x-y dimensions). In particular, the spatially-programmed capture probes migrate along one dimension (e.g., the z-dimension) of a biological sample. Referring to FIG. 6, in some instances, the spatially-programmed capture probes initially migrate in the z-dimension, but in different x-y locations. Using imaging techniques, the location of the spatially-programmed capture probes along the Z-dimension can be determined. See e.g., FIG. 7. Further, because the array is a two-dimensional (e.g., x- and y-dimensions) plane, the two-dimensional array includes capture probes having spatial barcodes that provides the location of the x- and y-dimensions. See FIG. 12, which shows that the x- and y-dimensions can be determined using the 2D array, while the third dimension (i.e., the z-dimension) is determined by the migration pattern of the spatially-programmed capture probe(s). Thus, when the spatially-programmed capture probes bind (e.g., hybridize) to capture probes on the array, the combination of the captured probes and the spatially-programmed capture probes provide information to decipher the three-dimensional location of the detected analyte.

Thus, featured herein are methods of spatially profiling an analyte in a biological sample (e.g., any of the exemplary biological samples described herein). Also provided herein are methods for determining a three-dimensional location of an analyte in a biological sample (e.g., any of the exemplary biological samples described herein). The methods of spatially profiling an analyte in a biological sample provided herein include use of a composition (e.g., a hydrogel) to facilitate migration of one or more capture probes through a biological sample. In some instances, the methods include: (a) applying the biological sample to a slide comprising an array comprising capture probes (e.g., capture probes for detection of an x-y location of an analyte); (b) immobilizing or embedding the biological sample disposed on the array using a hydrogel matrix; (c) providing a plurality of spatially-programmed capture probes; (d) migrating a spatially-programmed capture probe from the plurality of spatially-programmed capture probes through the biological sample along a first dimension (e.g., z-dimension; e.g., along an dimension perpendicular to the planar surface of the array) and determining the location of the spatially-programmed capture probe; (e) capturing an analyte by specifically binding the spatially-programmed capture probe to the analyte; (f) migrating the analyte/spatially-programmed capture probe product along the first dimension (e.g., z-dimension) to the two-dimensional array, where it is captured by a capture probe on the array; and (g) determining (i) all or a part of a sequence in the hybridized spatially-programmed capture probe, or a complement thereof, (ii) all or a part of the sequence of the spatial barcode, or a complement thereof, and (iii) all or part of the sequence of the analyte, or a complement thereof, and using the determined sequences of (i), (ii), and (iii), and the determined location in (e), to identify the location and abundance of the analyte in the three-dimensional space in the biological sample.

In some instances, the methods include permeabilizing the biological sample before adding a hydrogel to the biological sample. In some instances, the methods include permeabilizing the biological sample after adding a hydrogel to the biological sample. In some instances, the methods include permeabilizing the biological sample before adding the spatially-programmed capture probes. In some instances, the methods include permeabilizing the biological sample after adding the spatially-programmed capture probes. In some instances, permeabilization occurs after the sample is placed on the slide. As described herein, permeabilization can be performed using any method disclosed herein or known in the art, including using lysis reagents or proteases. In some embodiments, the permeabilized biological sample is immobilized to prevent lateral diffusion of the cells.

In some instances, the biological sample is permeabilized to allow access to the biological analyte and to allow spatially-programmed capture probes to enter into cell(s) within the biological sample. In some instances, the biological sample is permeabilized using an organic solvent (e.g., methanol or acetone). In some instances, a detergent (e.g., saponin, Triton X-100™ or Tween-20™) is used to permeabilize cells of a biological sample. In some instances, an enzyme (e.g., trypsin) may be used to permeabilize cells of a biological sample. Methods for cellular permeabilization are known in the art (see, e.g., Jamur and Oliver, Method Mol. Biol., 2010, 588:63-66). Any variety of suitable methods of cell permeabilization may be used to practice the methods disclosed herein.

In some instances, the biological sample can be permeabilized before the biological sample is immobilized using a hydrogel. In some instances, the biological sample can be permeabilized after the biological sample is immobilized using a hydrogel. Some embodiments of any of the methods described herein can further include permeabilizing the biological sample (e.g., using any of the methods for permeabilizing a biological sample described herein).

In some instances, disclosed herein are methods of controlling migration of the spatially-programmed capture probe in the hydrogel matrix. In some instances, the methods include ceasing migration of the spatially-programmed capture probe in the hydrogel matrix. In some instances, after ceasing migration, the methods include determining a location of the spatially-programmed capture probe in the hydrogel matrix in relation to one or both of (i) the array or (ii) the surface of the hydrogel matrix that is distal to the hydrogel matrix contacting the array, by detecting the detectable moiety.

Ceasing migration can be performed using any method known in the art. For example, in some instances, ceasing migration occurs due to the size (e.g., diameter, hydrodynamic radius) of the spatially-programmed capture probe (e.g., larger/longer probes migrate a shorter distance through a hydrogel-treated sample). In some instances, electrical or chemical means can be used to control the rate of migration through a sample. In some examples, the spatially-programmed capture probe can be actively directed to a biological sample using a variety of methods, e.g., electrophoresis, chemical gradient, pressure gradient, fluid flow, or magnetic field. Further, as described below, the programmable migration domain can be used to control migration of the spatially-programmed capture probe through the biological sample.

In some examples, the detecting step in the methods provided herein can include imaging the biological sample. The imaging can be performed using any of the imaging methods described herein. For example, the imaging can be performed using confocal microscopy. In some examples, the imaging can further be used to identify a region of interest in the permeabilized biological sample. In some examples, the imaging can include detection of detectable markers. In some examples, the imaging can include the use of fiducial markers. In some embodiments, the methods described herein can further include, between steps (d) and (e), contacting the hydrogel matrix with a polymerase (e.g., a reverse transcriptase) capable of extending the 3' end of the spatially-programmed capture probe using the nucleic acid analyte sequence as a template. In some embodiments, the method described herein can further include, between steps (d) and (e), adding one or more additional reagents to aid and/or increase the activity of the polymerase. In some embodiments, the methods further include, between steps (d) and (e), a step of inhibiting, inactivating, or decreasing the activity of the polymerase.

Also provided herein are methods for determining a three-dimensional location of a nucleic acid analyte in a permeabilized biological sample using multiple spatially-programmed capture probes. In some instances, the methods include (a) immobilizing the permeabilized biological sample disposed on an array (e.g., any of the exemplary arrays described herein) in a hydrogel matrix (e.g., any of the exemplary hydrogels described herein); (b) providing a plurality of pairs of spatially-programmed capture probes, where a pair of spatially-programmed capture probes in the plurality of pairs of spatially-programmed capture probes includes a first and a second spatially-programmed capture probe, where: at least one of the first and the second spatially-programmed capture probe includes a detectable moiety (e.g., any of the detectable moieties described herein); the first and the second spatially-programmed capture probe, when hybridized to the nucleic acid analyte, are capable of being ligated together; and each of the first and the second spatially-programmed capture probes comprise a programmable migration domain (e.g., any of the exemplary programmable migration domains described herein); (c) migrating the pair of spatially-programmed capture probes into the hydrogel matrix from a surface of the hydrogel matrix that is opposite to a surface of the hydrogel matrix contacting the array; (d) ceasing migration of the pair of spatially-programmed capture probes in the hydrogel matrix and determining a distance of the pair of the spatially-programmed capture probes in the hydrogel matrix from one or both of (i) the array or (ii) the surface of the hydrogel matrix that is opposite to the surface of the hydrogel matrix contacting the array, by detecting the detectable moiety; (e) ligating the first and the second spatially-programmed capture probes, when hybridized to the nucleic acid analyte, to generate a single-stranded ligation product; (f) migrating the single-stranded ligation product to the array, wherein the array comprises a plurality of capture probes, where a capture probe of the plurality of capture probes comprises a spatial barcode and a capture domain that binds specifically to a sequence in the single-stranded ligation product comprising at least one nucleotide 5' and at least one nucleotide 3' to a site of ligation in the single-stranded ligation product; and (g) determining (i) all or a part of the sequence in the single-stranded ligation product, or a complement thereof, and (ii) all or a part of the sequence of the spatial barcode, or a complement thereof, and using the determined sequences of (i) and (ii), and the determined distance in (d), to identify the three-dimensional location of the nucleic acid analyte in the biological sample.

In some embodiments, the methods described herein can further include contacting the hydrogel matrix with a ligase (e.g., any of the exemplary ligases described herein). In some embodiments, the method described herein can further include, between steps (d) and (e), adding one or more additional reagents to aid and/or increase the activity of the ligase. In some embodiments, the methods further include, between steps (d) and (e), a step of inhibiting, inactivating, or decreasing the activity of the ligase.

In some examples, the first spatially-programmed capture probe further includes a cleavage domain (e.g., any of the exemplary cleavage domains described herein), where upon cleavage of the cleavage domain, the programmable migration domain is released from the first spatially-programmed capture probe. In some examples, the method includes, between steps (e) and (f), cleaving the cleavage domain to release the programmable migration domain from the first spatially-programmed capture probe.

In some examples, the second spatially-programmed capture probe further includes a cleavage domain (e.g., any of the exemplary cleavage domains described herein), where upon cleavage of the cleavage domain, the programmable migration domain is released from the second spatially-programmed capture probe. In some examples, the method further includes, between steps (e) and (f), cleaving the cleavage domain to release the programmable migration domain from the second spatially-programmed capture probe.

In some examples, the first spatially-programmed capture probe further includes a cleavage domain (e.g., any of the exemplary cleavage domains described herein), where upon cleavage of the cleavage domain, the programmable migration domain is released from the first spatially-programmed capture probe; and the second spatially-programmed capture probe further includes a cleavage domain (e.g., any of the exemplary cleavage domains described herein), where upon cleavage of the cleavage domain, the programmable migration domain is released from the second spatially-programmed capture probe. In some examples, the method further includes, between steps (e) and (f) cleaving the cleavage domain to release the programmable migration domain from the first and second spatially-programmed capture probes.

In some embodiments, the cleavage domain comprises a recognition sequence for a restriction endonuclease. In some embodiments, the first and second spatially-programmed capture probes are oligonucleotide probes. In some embodiments, the migrating of the pair of spatially-programmed capture probes is performed using passive migration or active migration (e.g., any of the exemplary means for performing active migration described herein). In some embodiments, the active migration can be performed using an electric field, a magnetic field, a charged gradient, or any combination thereof. In some examples, active migration can be performed using pulsed-field electrophoresis and/or rotating field electrophoresis. Additional methods for performing active migration are described herein, and are known in the art. In some examples, the migrating of the pair of spatially-programmed capture probes can be performed in a linear or a non-linear direction.

In some examples, the determining step (e.g., determining the spatial location and abundance of an analyte) can include sequencing (i) all or a part of the sequence in the single-stranded ligation product, or a complement thereof, and (ii) all or a part of the sequence of the spatial barcode, or a complement thereof. Any of the non-limiting methods for sequencing a nucleic acid sequence described herein or known in the art can be used in step (g). For example, the sequencing can be performed using sequencing-by-synthesis (SBS), sequential fluorescence hybridization, sequencing by ligation, nucleic acid hybridization, or high-throughput digital sequencing techniques.

(b) Hydrogels (i) Hydrogel Polymers and Moieties

Figure 9:
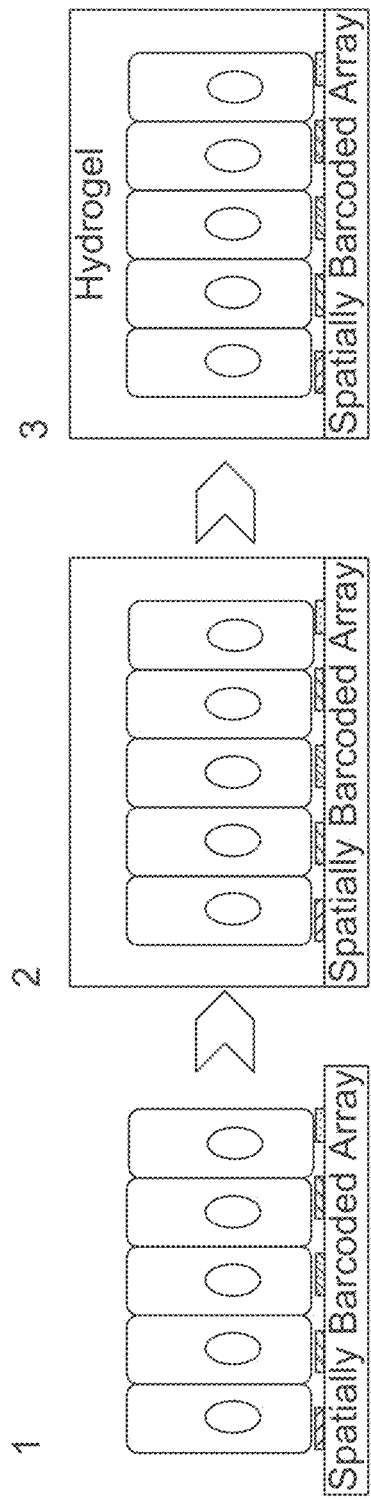
FIG. 9 shows an exemplary workflow depicting the steps involved in contacting a biological sample with a spatially barcoded array and embedding the biological sample in a hydrogel matrix.
Figure 10:
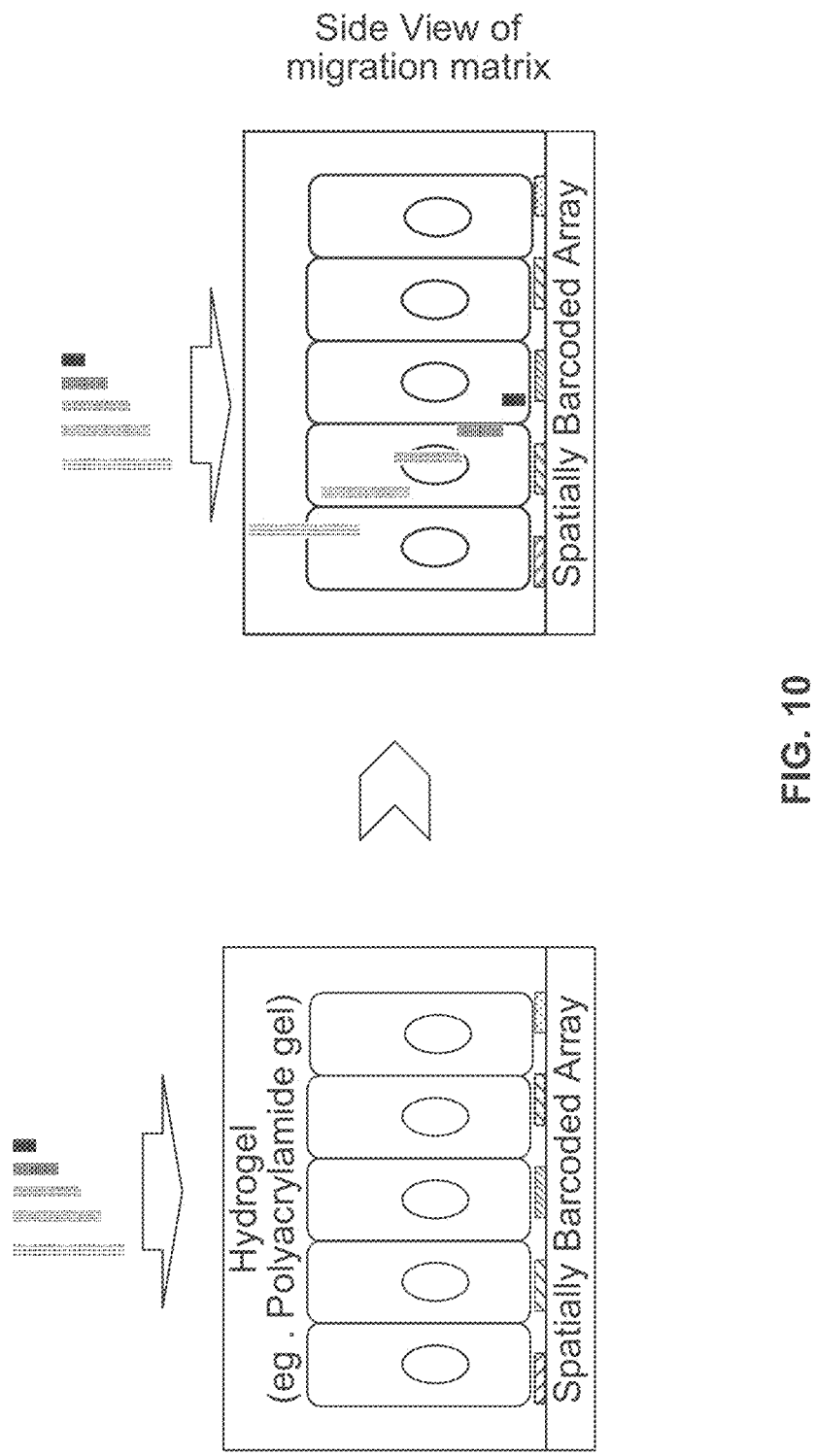
FIG. 10 shows an exemplary process of introducing z-dimensional, or spatially programmed, capture probes to a biological sample, and migrating the capture probes along a direction through the biological sample, where the capture probes migrate to a migration position in the biological sample.
Figure 15B:
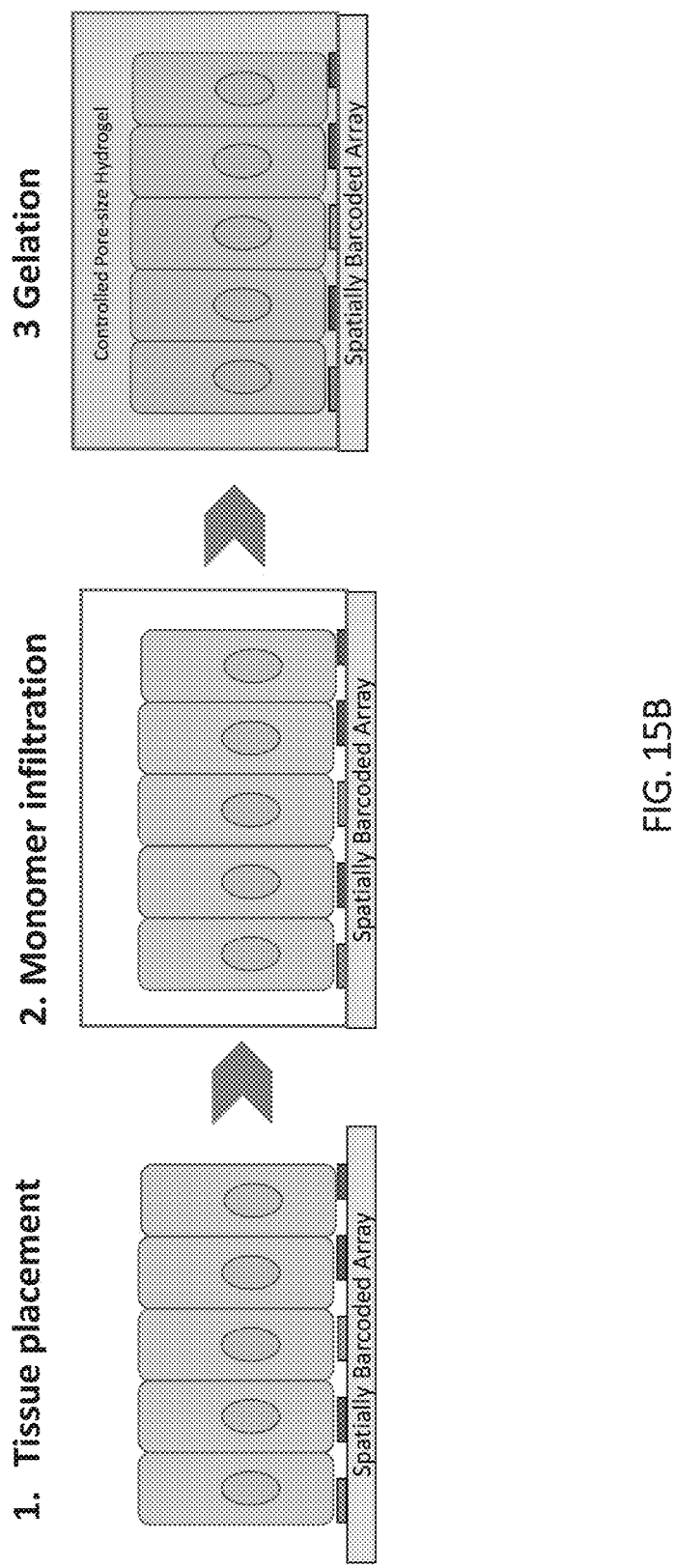
FIG. 15B is an embodiment depicting hydrogel embedding of a biological sample.

Disclosed herein are various hydrogels (also called hydrogel matrices) that can be used to facilitate probe migration. In some embodiments, a biological sample (e.g., tissue section) is embedded in a hydrogel. In some embodiments, the present disclosure utilizes a multi-step method to embed a biological sample in hydrogel. As shown in FIG. 9, a biological sample is placed onto a spatial array (i.e., "spatially barcoded array" in FIG. 9). After, a hydrogel is placed onto the biological sample. As shown in FIG. 10, spatially-programmed capture probes migrate through the hydrogel and biological sample and is imaged (FIG. 11). In an additional embodiment, referring to FIG. 15B, after the tissue is placed on the array (FIG. 15B, left), one or more spatially-programmed capture probe can be placed over the sample. The one or more monomers infiltrate the sample (FIG. 15B, middle). A step of gelation occurs (FIG. 15B, right), securing the biological sample in the hydrogel solution. In some embodiments, hydrogel subunits are infused into the biological sample, and polymerization of the hydrogel is initiated by an external or internal stimulus. A "hydrogel" as described herein can include a cross-linked three-dimensional (3D) network of hydrophilic polymer chains. A "hydrogel subunit" can be a hydrophilic monomer, a molecular precursor, or a polymer that can be polymerized (e.g., cross-linked) to form a 3D hydrogel network. In some embodiments, a hydrogel includes a natural material. In some embodiments, a hydrogel includes a synthetic material. In some embodiments, a hydrogel includes a hybrid material, e.g., the hydrogel material includes elements of both synthetic and natural polymers. Any of the variety of hydrogels described herein can be used. Non-limiting examples of materials used in hydrogels include collagen, fibrin, alginate, polyacrylamide, polyethylene glycol, hyaluronic acid, a polypeptide, chitosan, silk, poly(vinyl alcohol) (PVA), poly-N-isopropylacrylamide (pNIPAm), and dextran. See, e.g., Caliari et al., Nat Methods. 2016 Apr. 28; 13(5): 405-414, which is incorporated herein by reference in its entirety. Non-limiting examples of a hydrogel including a polypeptide-based material can include a synthetic peptide-based material including a combination of spider silk and a trans-membrane segment of human muscle L-type calcium channel (e.g., PEPGEL®), an amphiphilic 16-residue peptide containing a repeating arginine-alanine-aspartate-alanine sequence (RADARADARADARADA (SEQ ID NO:1)) (e.g., PURAMATRIX®), EAK16 (AEAEAKAKAEAEAKAK (SEQ ID NO:2)), KLD12 (KLDLKLDLKLDL (SEQ ID NO:3)), and PGMATRIX™. Additional non-limiting methods that can be used to immobilize a biological sample (e.g., a permeabilized biological sample) disposed on an array in a hydrogel matrix are described herein. Additional exemplary aspects of a hydrogel matrix are also described herein.

In some instances, a hydrogel can comprise a natural polymer, a synthetic polymer or both natural and synthetic polymers. Examples of natural polymers include proteins such as collagen and gelatin, and polysaccharides such as starch, alginate and agarose. Examples of synthetic polymers include acrylics, polyacrylamide, polyacrylate, polyethylene glycol, and the like. Hydrogels may also be formed from materials other than polymers, including lipids, micelles, ceramics, material composites, and other inorganic materials.

Figure 16A:
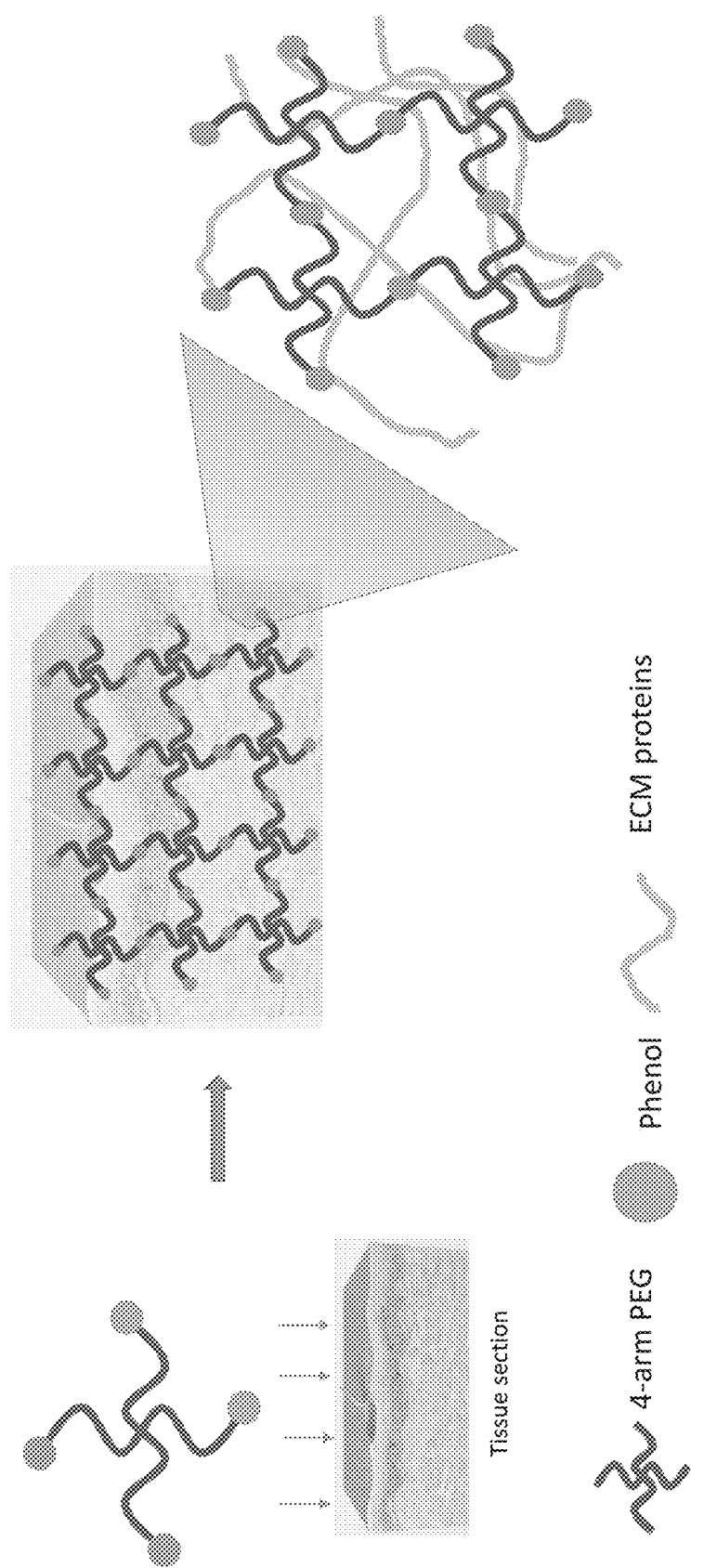
FIG. 16A is an embodiment depicting hydrogel embedding of a biological sample using a phenol-containing hydrogel.

In some instances, the hydrogel includes a polyether compound that aids in crosslinking extracellular matrix proteins in the biological sample. In some instances, the polyether compound is a polyethylene glycol (PEG). In some instances, the hydrogel includes multiple monomers of PEGs. In some instances, the hydrogel comprises at least 2, 3, 4, 5, 6, 7, 8, 9, or 10 monomers of PEGs that are bound together, forming a tetrahedral polymer comprising polyethylene glycol (PEG) monomers. In some instances, as shown in FIG. 16A (upper left image), the hydrogel includes four monomers bound together (e.g., a 4-arm PEG). In some instances, the hydrogel includes a homogenous polymer structure that includes multiple polymers (e.g., multiple units of four monomers PEGs). See, e.g., FIG. 16A, showing a 4-arm (e.g., tetrahedral) PEG. In some instances, the tetrahedral PEG monomers form a lattice-like polymer network resulted in hydrogels with extremely high structural homogeneity. The chemistry of forming PEG-lattice hydrogels is described further in Gao et al., "A highly homogeneous expansion microscopy polymer composed of tetrahedron-like monomers." bioRxiv 814111, October 2019, which is incorporated by reference in its entirety.

In at least one embodiment of the composition of the present disclosure, the hydrogel comprises cross-linked linear polymers, wherein the crosslinking moiety comprises a phenol moiety (e.g., a phenol group). In some instances, the tetrahedral polyethylene glycol (PEG) monomers include phenol groups adhered (e.g., bound) to the PEG monomers. In some instances, as shown in FIG. 16A, the phenol group is bound to the PEG monomers at the terminal ends of the PEG moiety to form a phenol-PEG moiety. In some instances, as shown in FIG. 16A (right side of FIG. 16A), the phenol-PEG moieties form a lattice network both inside a cell and in the extracellular matrix (ECM). The lattice structure interacts with the macromolecules of the biological sample and crosslinks the macromolecules in three-dimensional space. In some instances, the macromolecule to which phenol-PEG moiety crosslinks is one or more extracellular matrix protein in the biological sample. In some instances, the macromolecule is a protein. In some instances, an amino acid (e.g., tyrosine) from a protein (e.g., an ECM protein) undergoes crosslinking with the hydrogel matrix during gelation. In some instance, the phenol-PEG-moiety crosslinks to one or more intracellular macromolecules in the biological sample.

In some instances, the hydrogel can include the following structure:

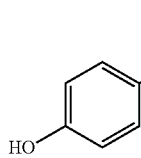
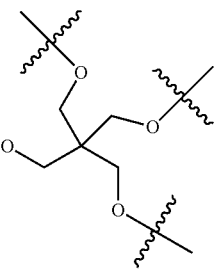

In some instances, the hydrogel comprises cross-linked linear polymers, wherein the crosslinking moieties comprise one or more azide moieties (e.g., azide groups). In some instances, the hydrogel comprises cross-linked linear polymers, wherein the crosslinking moieties comprise one or more alkyne moieties (e.g., alkyne groups). In some instances, the hydrogel comprises cross-linked linear polymers, wherein the crosslinks comprise both (1) one or more azide groups and (2) one or more alkyne groups. In some instances, the hydrogel comprises a hydrogel that includes both (1) one or more azide groups and (2) one or more alkyne groups at equal ratios. In some embodiments, the linear polymers are modified using NHS chemistry to include one or more azide groups and/or one or more alkyne groups In some instances, the hydrogel comprises a hydrogel that includes more (e.g., about 1, 2, 3, 4, 5, 6, 7, 8, 9 10, 15, 20, 25, 30, 35, 40, 45, 50, 55, 60, 65, 70, 75, 80, 85, 90, 95, 100%, 1.25×, 1.5×, 1.75×, 2×, or more) of (1) one or more azide groups than (2) one or more alkyne groups. In some instances, the hydrogel comprises a hydrogel that includes less (e.g., about 1, 2, 3, 4, 5, 6, 7, 8,9 10, 15, 20, 25, 30, 35, 40, 45, 50, 55, 60, 65, 70, 75, 80, 85, 90, 95, 1.25×, 1.5×, 1.75×, 2×, or less) of (1) one or more azide groups than (2) one or more alkyne groups.

Figure 16B:
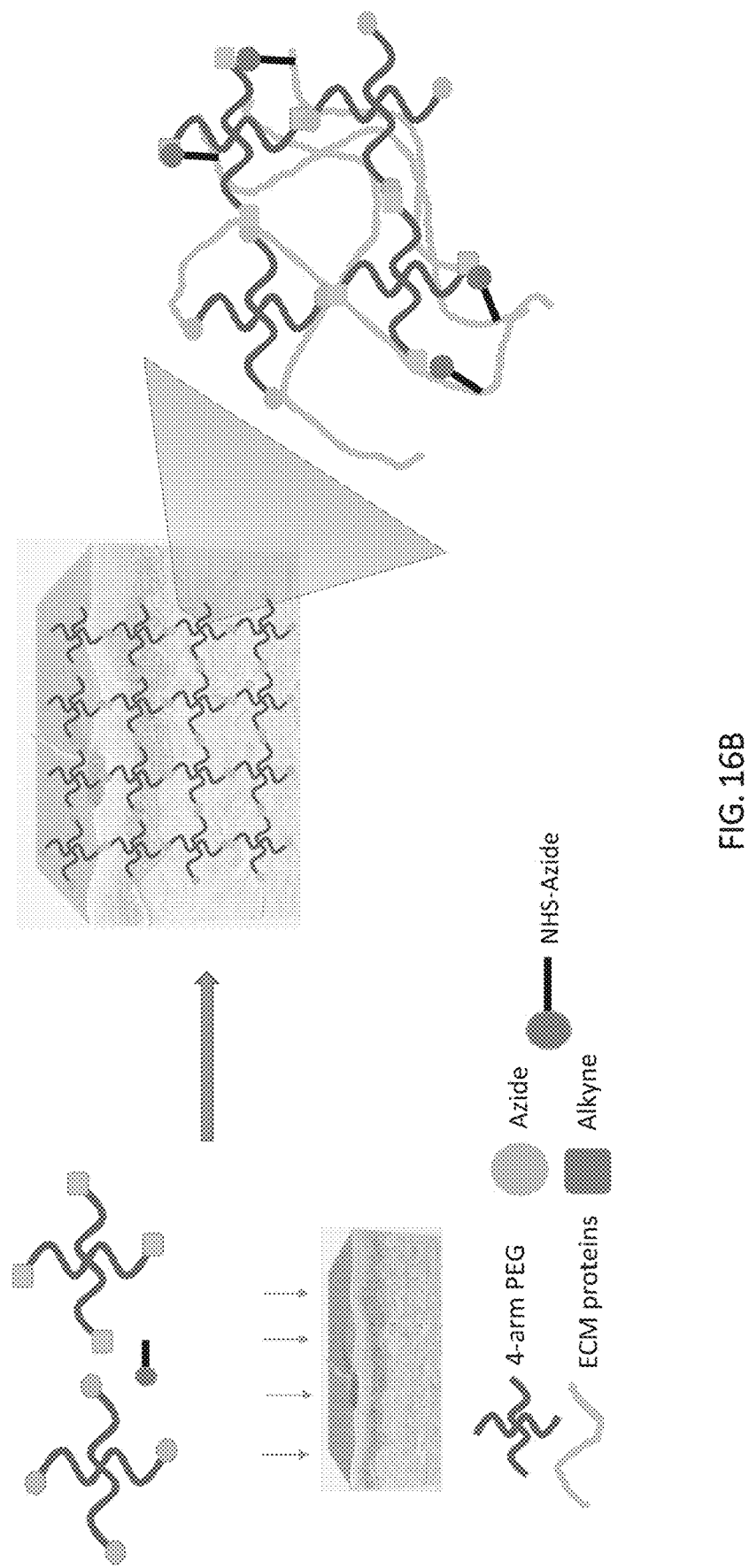
FIG. 16B is an embodiment depicting hydrogel embedding of a biological sample using an azide- and/or alkyne-containing hydrogel.

As an exemplary embodiment, as shown in FIG. 16B, a hydrogel includes PEG moieties that include both azide and alkyne moieties, creating a tetrahedral PEG hydrogel. The hydrogel is placed on the biological sample and infiltrates the biological sample. In some instances, the azide and alkyne-modified tetrahedral PEG moieties form a lattice structure both inside a cell and in the extracellular matrix of a biological sample. In some instances, the azide and/or alkyne moieties interact with macromolecules in the biological sample. In some instances, the azide and/or alkyne moieties interact with proteins in the biological sample. In some instances, the protein of the biological sample includes an azide that interacts with the tetrahedral PEG moiety (e.g., at the azide and/or alkyne moieties).

In at least one embodiment, the composition further comprises a crosslink-catalyzing enzyme distributed throughout the hydrogel, wherein the enzyme is not attached to the cell or the linear polymer; optionally, wherein the crosslink-catalyzing enzyme is selected from horse radish peroxidase (HRP); transglutaminase; tyrosinase; and laccase.

In some instances, a hydrogel can swell in the presence of water. In some embodiments, a hydrogel comprises a natural material. In some embodiments, a hydrogel includes a synthetic material. In some embodiments, a hydrogel includes a hybrid material, e.g., the hydrogel material comprises elements of both synthetic and natural polymers. Any of the materials used in hydrogels or hydrogels comprising a polypeptide-based material can be used. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art. For example, the biological sample can be immobilized in the hydrogel by polyacrylamide crosslinking. Further, analytes of a biological sample can be immobilized in a hydrogel by crosslinking (e.g., polyacrylamide crosslinking).

The composition and application of the hydrogel to a biological sample typically depends on the nature and preparation of the biological sample (e.g., sectioned, non-sectioned, fresh-frozen tissue, type of fixation). A hydrogel can be any appropriate hydrogel where upon formation of the hydrogel on the biological sample the biological sample becomes anchored to or embedded in the hydrogel. Non-limiting examples of hydrogels are described herein or are known in the art. As one example, where the biological sample is a tissue section, the hydrogel can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel are formed in compartments, including but not limited to devices used to culture, maintain, or transport the cells. For example, hydrogels can be formed with monomer solution plus APS/TEMED added to the compartment to a depth ranging from about 0.1 m to about 5 mm (e.g., about 0.5 m to about 5 mm, about 1.0 m to about 5 mm, about 10 m to about 5 mm, about 100 m to about 5 mm, about 1 mm to about 5 mm, about 2 mm to about 5 mm, about 3 mm to about 5 mm, about 4 mm to about 5 mm, about 0.1 m to about 4 mm, about 0.1 m to about 3 mm, about 0.1 m to about 2 mm, about 0.1 m to about 1 mm, about 0.1 m to about 100 μm, about 0.1 m to about 10 μm, about 0.1 m to about 1 μm, or about 0.1 m to about 0.5 μm).

In some embodiments, a hydrogel includes a linker that allows anchoring of the biological sample to the hydrogel. In some embodiments, a hydrogel includes linkers that allow anchoring of biological analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl)amino) hexanoic acid (Acryloyl-X SE) (available from ThermoFisher, Waltham, MA), Label-IT Amine (available from MirusBio, Madison, WI) and Label X (Chen et al., Nat. Methods 13:679-684, (2016)).

In some embodiments, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., capture probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, protease, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell tagging agent is added to the hydrogel before, contemporaneously with, and/or after polymerization. In some embodiments, a cell-penetrating agent is added to the hydrogel before, contemporaneously with, and/or after polymerization.

In some embodiments, a biological sample is embedded in a hydrogel to facilitate sample transfer to another location (e.g., to an array). For example, archived biological samples (e.g., FFPE tissue sections) can be transferred from storage to a spatial array to perform spatial analysis. In some embodiments, a biological sample on a substrate can be covered with any of the prepolymer solutions described herein. In some embodiments, the prepolymer solution can be polymerized such that a hydrogel is formed on top of and/or around the biological sample. Hydrogel formation can occur in a manner sufficient to anchor (e.g., embed) the biological sample to the hydrogel. After hydrogel formation, the biological sample is anchored to (e.g., embedded in) the hydrogel wherein separating the hydrogel from the substrate (e.g., glass slide) results in the biological sample separating from the substrate along with the hydrogel. The biological sample contained in the hydrogel can then be contacted with a spatial array, and spatial analysis can be performed on the biological sample.

Any variety of characteristics can determine the transfer conditions required for a given biological sample. Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)).

In some embodiments, the hydrogel is removed after contacting the biological sample with the spatial array. For example, methods described herein can include a stimulus-dependent (e.g., light, or chemical) depolymerizing hydrogel, wherein upon application of the stimulus (e.g., external stimulus) the hydrogel depolymerizes. In one example, a biological sample can be anchored to a DTT-sensitive hydrogel, where addition of DTT can cause the hydrogel to depolymerize and release the anchored biological sample.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored in a medium before or after clearing of hydrogel (e.g., a mounting medium, methylcellulose, or other semi-solid mediums).

In some embodiments, the hydrogel chemistry can be tuned to specifically bind (e.g., retain) particular species of analytes (e.g., RNA, DNA, protein, etc.). In some embodiments, a hydrogel includes a linker that allows anchoring of the biological sample to the hydrogel. In some embodiments, a hydrogel includes linkers that allow anchoring of biological analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl)amino) hexanoic acid (Acryloyl-X SE), Label-IT Amine and Label X (Chen et al., Nat. Methods 13:679-684, (2016)). Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)).

Additional methods and aspects of hydrogel embedding of biological samples are described for example in Chen et al., Science 347(6221):543-548, 2015, the entire contents of which are incorporated herein by reference.

(ii) Preparation of Hydrogels and Moieties

Figure 18:
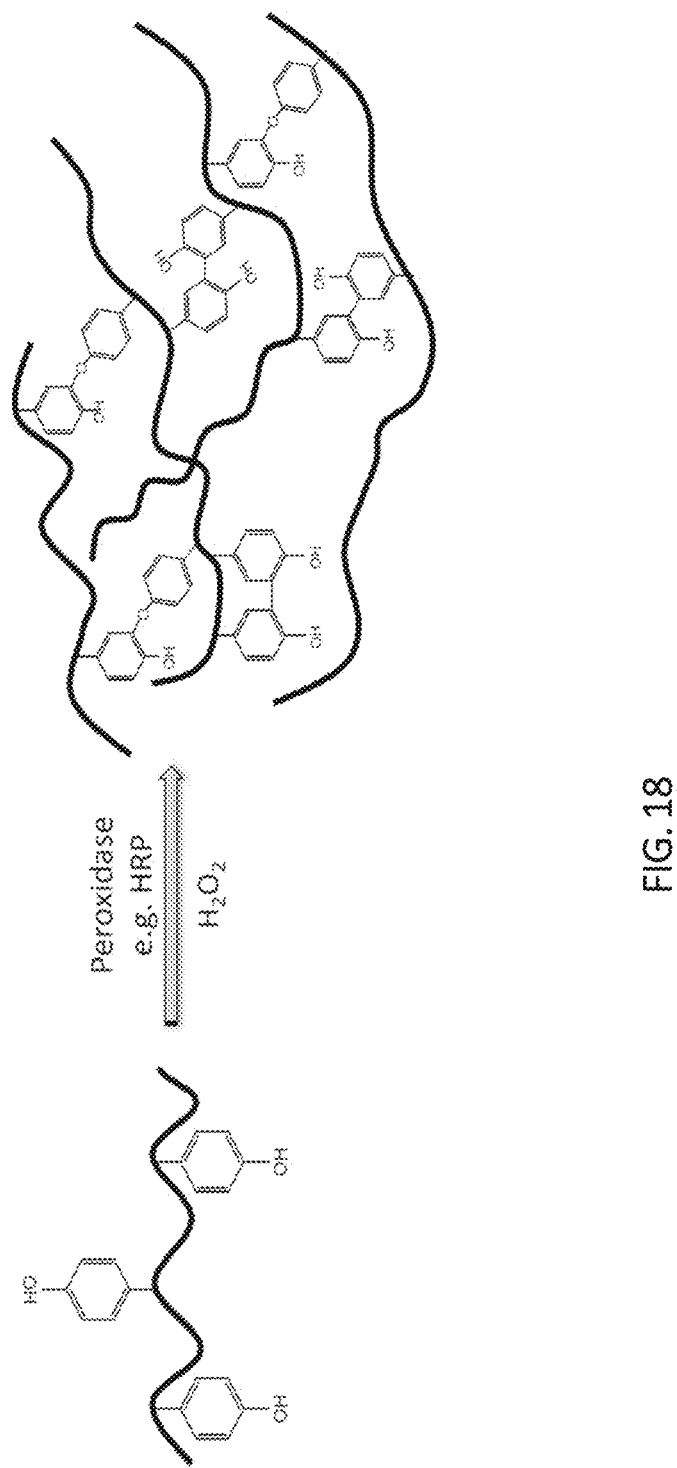
FIG. 18 depicts an exemplary scheme for peroxidase catalyzed crosslinking of phenol-modified linear polymers in the presence of co-substrate $H_2O_2$ to form a hydrogel matrix.

In another embodiment, the present disclosure provides hydrogel-coated cell compositions and methods for their preparation via a two-step enzymatically catalyzed gelation process. Generally, the methods and compositions of the present disclosure include the formation of a hydrogel-coating around a cell. The hydrogel-coating is formed by providing in the solution around the cell, one or more linear polymers, wherein the linear polymers are modified with a chemical moiety (e.g., an azide group, an alkyne group, a phenol group) capable of undergoing a reaction that forms a covalent crosslink (i.e., a crosslink precursor moiety) with another linear polymer in the mixture. See e.g., FIG. 18. Formation of these crosslinks between the linear polymers in a partition solution containing a cell results in the formation of a hydrogel with a cell embedded or entrapped in the matrix. Linear polymers useful in the methods and compositions of the present disclosure include, an olefin copolymer, a polyolefin, an acrylic, a polyacrylamide, a poly (oxazoline), a vinyl polymer, a polyester, a polycarbonate, a polyamide, a polyimide, a formaldehyde resin, a polyurethane, an ether polymer, a cellulosic, a thermoplastic elastomer, and a thermoplastic polyurethane. In some instances, the polymer is a polyethylene glycol. Materials and methods for forming hydrogel matrices in partitions by crosslinking linear polymers are known in the art. See e.g., US Pat. Publ. Nos. 2019/0100632A1, and 2019/0233878A1, each of which is hereby incorporated by reference herein.

Figure 19:
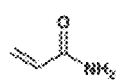
FIG. 19 depicts an exemplary 1-step scheme for preparing phenol-modified linear polymers capable of undergoing enzyme-catalyzed crosslinking to form a hydrogel matrix.
Figure 19:
Figure 19:
Figure 19:
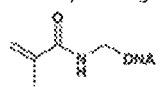
Figure 19:
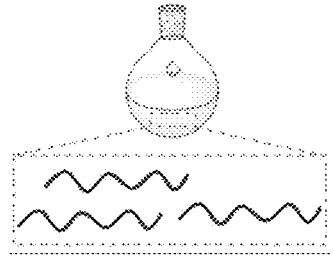
Figure 19:
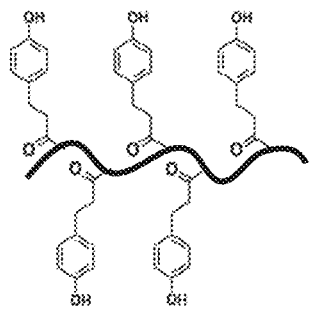

FIG. 19 depicts an exemplary scheme for preparing phenol-modified linear polymers capable of undergoing enzyme-catalyzed crosslinking to form a hydrogel matrix. In a first step, an aqueous monomer solution is prepared of monomers capable of forming linear polymers with modifiable side chains. In at least one embodiment the monomers are acrylamide and 3-aminopropyl methylacrylamide. The aminopropyl group provides a side chain that can be modified for attachment of other groups. Also included is sodium formate as a chain transfer agent to facilitate the formation of linear polymers. In at least one embodiment, a 5'-acrydite oligonucleotide is also included to provide linear polymers modified with oligonucleotides.

Linear polymers can be generated in solution via a range of polymerization methods. For example, polymerization can be initiated by free-radical generating compounds, such as, for example, benzoyl peroxide, 2,2-azo-isobutyronitrile (AIBN), and ammonium peroxodisulphate, or by using UV-, gamma-, or electron beam-radiation. In at least one embodiment, shown in step 2 of FIG. 19, linear polymers are generated from acrylamide monomers using a VA-044 thermal initiated polymerization method.

As shown in step 3 of FIG. 19, in at least one embodiment, the linear polymers once formed are then modified (or functionalized) with crosslink precursor moieties which are capable of acting as a substrate for a crosslink-catalyzing enzyme moiety. In the exemplary embodiment of FIG. 19, the crosslink precursor moieties coupled to the linear polymers are phenol groups. The modification of the linear polymers with crosslink precursor moieties, such as phenol groups, can be carried out using any of range of known bioconjugation chemistries used for attaching biomolecules such as enzymes or antibodies to other biomolecules, polymers, and/or solid supports. Typically, the conjugation is not direct to the linear polymer side chain but includes a linker moiety between the enzyme and the amine group. A range of linkers (also referred to as spacers), including linkers comprising cleavable linker moieties, are known in the art of bioconjugation and can be used in the methods and compositions of the present disclosure. Among the known linkers useful in the compositions and methods of the present disclosure are: non cleavable alkyl linkers, 5'-thiol Modifier C6 S—S linkers, photocleavable spacers, UDG-cleavable spacers, and oligonucleotides.

Figure 20:
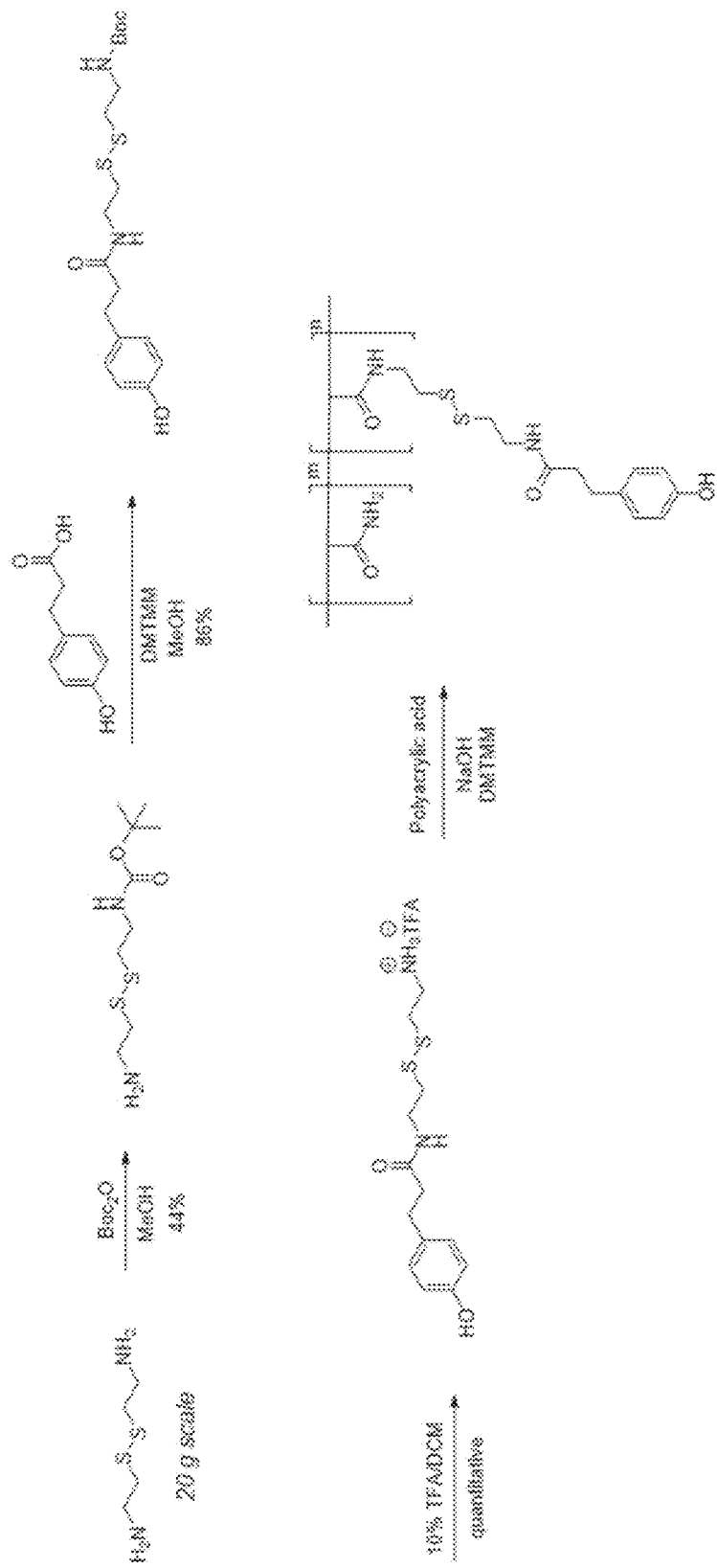
FIG. 20 depicts an exemplary reaction scheme for modifying polyacrylamide with phenol groups attached through a linker comprising a cleavable disulfide moiety.

In one embodiment of the methods and compositions of the present disclosure, the linear polymers (e.g., polyacrylamide) are modified with crosslink precursor moieties (e.g., phenol groups) that are attached via a cleavable linker. An exemplary reaction scheme for modifying a polyacrylamide with a phenol groups attached through a linker comprising a cleavable disulfide moiety is shown in FIG. 20. The disulfide linkages permit the linkers to be cleaved upon exposure to a stimulus, such as a reducing agent (e.g., DTT), thereby allowing for the hydrogel matrix to be selectively degraded or dissolved. The ability to selectively degrade a hydrogel-coating that entraps a cell can provide for the hydrogel-coated cells in a variety of methods of selective cell-culturing, cell-storage, and/or cell assays. Techniques and methods for the preparation and use of degradable hydrogels in partitions is known in the art. See e.g., US Pat. Publ. Nos. 2019/0100632A1, and 2019/0233878A1, each of which is hereby incorporated by reference herein.

(c) Biological Samples and Preparation of the Same

To facilitate visualization, biological samples can be stained using a wide variety of stains and staining techniques. In some embodiments, a sample can be stained using any number of biological stains, including but not limited to, cresyl violet, DAPI, eosin, hematoxylin, and Hoechst stains.

The sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other low pH acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in a low pH acid (e.g., HCl). In some embodiments, destaining can include adding HCl to a downstream solution (e.g., permeabilization solution). In some embodiments, destaining can include dissolving an enzyme used in the disclosed methods (e.g., pepsin) in a low pH acid (e.g., HCl) solution. In some embodiments, after destaining hematoxylin with a low pH acid, other reagents can be added to the destaining solution to raise the pH for use in other applications. For example, SDS can be added to a low pH acid destaining solution in order to raise the pH as compared to the low pH acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

The compositions and methods include any one of the biological samples described herein. In some instances, the biological sample can be a permeabilized biological sample. In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). In some embodiments, the biological sample can be permeabilized using any of the methods described herein (e.g., using any of the detergents described herein, e.g., SDS and/or N-lauroylsarcosine sodium salt solution) before or after enzymatic treatment (e.g., treatment with any of the enzymes described herein, e.g., trypin, proteases (e.g., pepsin and/or proteinase K)).

In some embodiments, a biological sample can be permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsarcosine or N-lauroylsarcosine sodium salt. In some embodiments, a biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsarcosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In some embodiments, the biological sample can be incubated with a permeabilizing agent to facilitate permeabilization of the sample. Additional methods for sample permeabilization are described, for example, in Jamur et al., Method Mol. Biol. 588:63-66, 2010, the entire contents of which are incorporated herein by reference.

In some instances, the biological sample is permeabilized before the spatially-programmed capture probes are added to the sample. In some instances, the permeabilized biological sample is a tissue sample. In some instances, the tissue sample is a tissue section. In some instances, the tissue sample is a formalin-fixed, paraffin-embedded tissue sample, a fresh tissue sample, or a fresh, frozen tissue sample. In some instances, the tissue sample includes a tumor cell. The biological sample includes one or more nucleic acid analytes to be detected. In some instances, the nucleic acid analyte is RNA (e.g., any of the types of RNA described herein). In some instances, the RNA can be mRNA. In some instances, the nucleic acid analyte is DNA. In some instances, the nucleic acid analyte is immobilized in a hydrogel matrix. In some instances, the nucleic acid analyte is immobilized in a hydrogel matrix by cross-linking.

In some instances, the biological sample is permeabilized to allow access to the biological analyte and to allow spatially-programmed capture probes to enter into cell(s) within the biological sample. In some instances, the biological sample is permeabilized using an organic solvent (e.g., methanol or acetone). In some instances, a detergent (e.g., saponin, Triton X-100™ or Tween-20™) is used to permeabilize cells of a biological sample. In some instances, an enzyme (e.g., trypsin) may be used to permeabilize cells of a biological sample. Methods for cellular permeabilization are known in the art (see, e.g., Jamur and Oliver, Method Mol. Biol., 2010, 588:63-66). Any variety of suitable methods of cell permeabilization may be used to practice the methods disclosed herein. Additional exemplary methods for permeabilizing a biological sample are described herein. In some instances, the biological sample can be permeabilized before the biological sample is immobilized using e.g., a hydrogel. In some instances, the biological sample can be permeabilized after the biological sample is immobilized using e.g., a hydrogel. Some embodiments of any of the methods described herein can further include permeabilizing the biological sample (e.g., using any of the methods for permeabilizing a biological sample described herein).

(d) Methods for Delivering a Spatially-Programmed Capture Probe to a

Permeabilized Biological Sample

In some embodiments, also provided herein are methods for delivering a spatially-programmed capture probe to a permeabilized biological sample (e.g., any of the exemplary biological samples described herein) that include: (a) immobilizing the permeabilized biological sample disposed on an array (e.g., any of the exemplary arrays described herein) in a hydrogel matrix (e.g., any of the exemplary hydrogels described herein); (b) providing a plurality of spatially-programmed capture probes, where a spatially-programmed capture probe in the plurality of spatially-programmed capture probes includes: (i) a programmable migration domain (e.g., any of the exemplary programmable migration domains described herein); (ii) a detectable moiety (e.g., any of the exemplary detectable moieties described herein); and (iii) a capture domain that binds specifically to a sequence within a nucleic acid analyte in the permeabilized biological sample; and (c) migrating the spatially-programmed capture probe into the hydrogel matrix from a surface of the hydrogel matrix that is opposite to a surface of the hydrogel matrix contacting the array.

Also provided herein are methods for delivering a pair of spatially-programmed capture probes to a permeabilized biological sample (e.g., any of the exemplary biological samples described herein) that include: (a) immobilizing the permeabilized biological sample disposed on an array (e.g., any of the exemplary arrays described herein) in a hydrogel matrix; (b) providing a plurality of pairs of spatially-programmed capture probes, where a pair of spatially-programmed capture probes in the plurality of pairs of spatially-programmed capture probes includes a first and a second spatially-programmed capture probe, where: at least one of the first and the second spatially-programmed capture probe comprises a detectable moiety (e.g., any of the exemplary detectable moieties described herein); the first and the second spatially-programmed capture probe, when hybridized to a nucleic acid analyte in the biological sample, are capable of being ligated together; and each of the first and the second spatially-programmed capture probes comprise a programmable migration domain (e.g., any of the programmable migration domains described herein), and (c) migrating the pair of spatially-programmed capture probes into the hydrogel matrix from a surface of the hydrogel matrix that is opposite to a surface of the hydrogel matrix contacting the array.

Figures 13A, 13B, 13C, 13D, 13E:
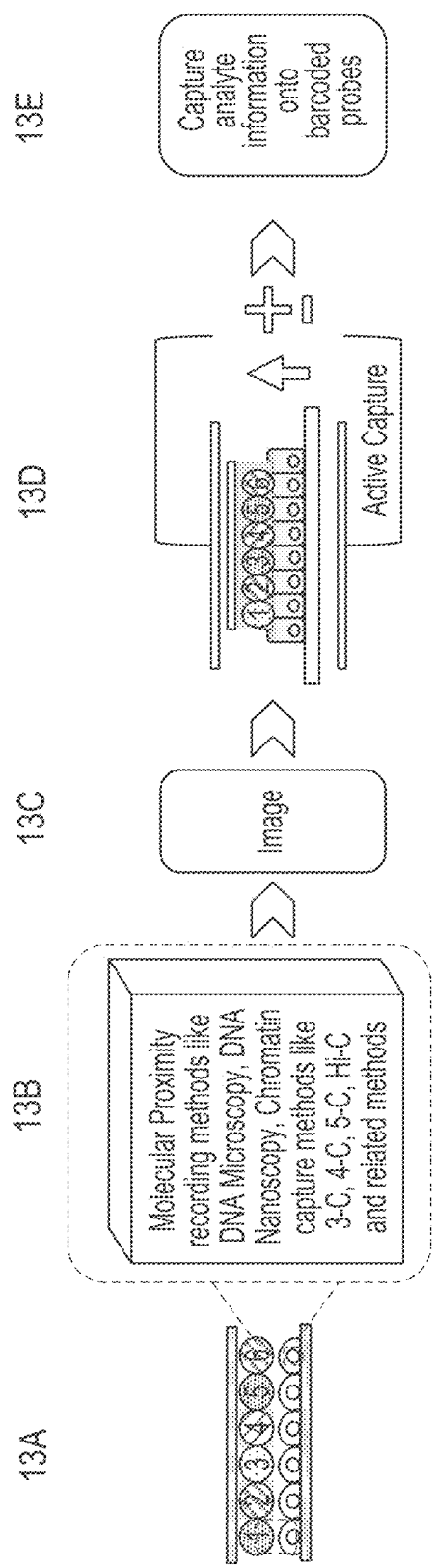
FIGS. 13A-13E and 14A-14E show a schematic diagram showing an exemplary workflow for a method for 3-dimensional spatial profiling of a biological analyte in a biological sample.
Figures 14A, 14B, 14C, 14D, 14E:
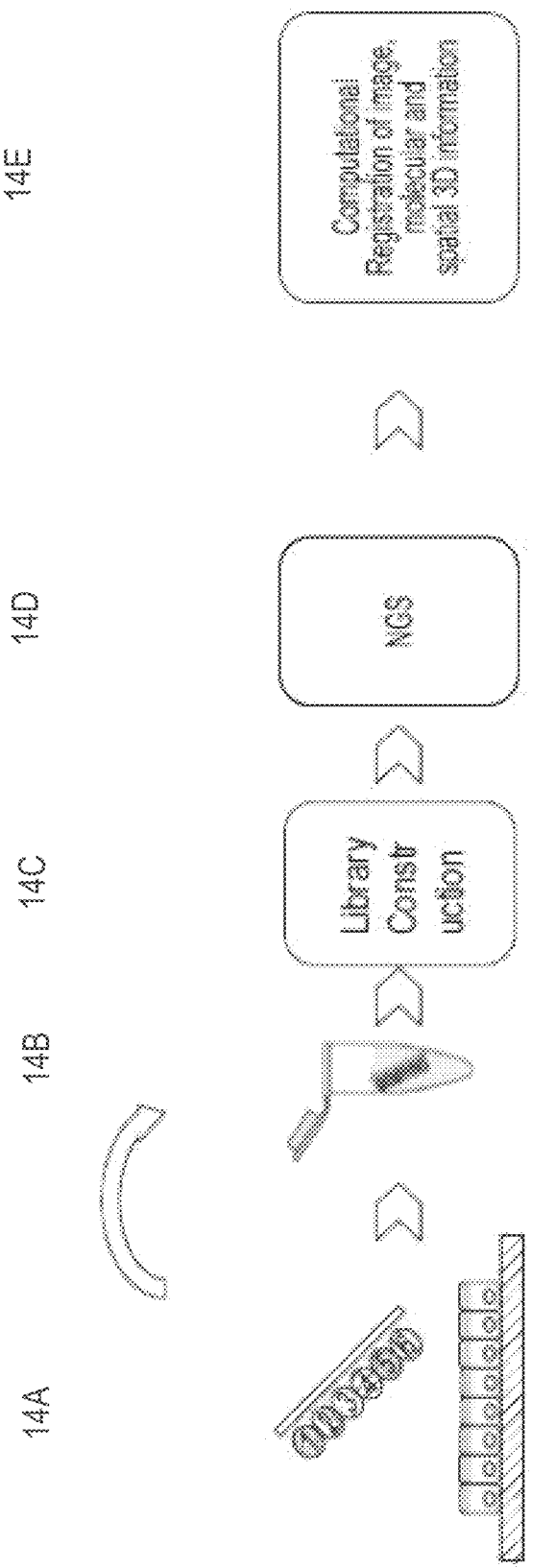

In some instances, referring to FIGS. 13A-13E and 14A-14E, the cells of the biological sample can be immobilized on a solid substrate (FIG. 13A). A proximity ligation reaction can then be performed on the biological sample such that pairs of proximal biological analytes are associated with each other (FIG. 13B). The biological sample can then be imaged (FIG. 13C). The biological sample can then be contacted with a substrate (e.g., a solid support) comprising a plurality of capture probes, wherein the capture probes individually comprise a spatial barcode and a capture domain, such that the proximally-associated biological analytes in the biological sample can interact with the capture probes (FIGS. 13D-13E). Referring next to FIGS. 14A-14E, the capture probes/proximally-associated biological analyte pairs can be analyzed, and the proximally-associated biological analyte pairs can be correlated with the distinct spatial position of the substrate (e.g., a solid support). The 3-dimensional spatial profile of the biological analytes in the biological sample can be reconstructed by analyzing the determined 2-dimensional spatial profile of the one or more captured proximally-associated analyte pairs in conjunction with the determined identities of the biological analytes of one or more proximally-associated biological analyte pairs.

In some embodiments, a method for delivering spatially-programmed capture probes in a biological sample can include: immobilizing the sample in a matrix; providing a plurality of spatially-programmed capture probes as described herein; and allowing the plurality of spatially-programmed capture probes to migrate in the matrix, thereby delivering spatially-programmed capture probes in the biological sample. As another example, a method for determining a three-dimensional location of a plurality of one or more biological analyte of interest in a biological sample can include: immobilizing the biological sample in a matrix; providing a plurality of spatially-programmed capture probes as described herein; allowing the plurality of spatially-programmed capture probes to migrate in the matrix; immobilizing the plurality of spatially-programmed capture probes in the matrix; determining the location of the plurality of spatially-programmed capture probes in the matrix by imaging; allowing the plurality of spatially-programmed capture probes to contact a plurality of biological analytes; and binding the biological analyte of interest from the plurality of biological analytes to the capture probes, thereby determining location of the biological analyte of interest.

In some embodiments, the cells from the biological sample are immobilized on the substrate (e.g., a solid support). In some embodiments, the cells are immobilized in a matrix to prevent lateral diffusion of the cells and/or to provide a matrix for the migration of a plurality of spatially-programmed capture probes. For example, a hydrogel can be used to immobilize the cells and to provide the matrix. In some embodiments, the hydrogel is any of the hydrogels described herein. In some embodiments, the hydrogel includes a polypeptide-based material. Non-limiting examples of a hydrogel including a polypeptide-based material can include a synthetic peptide-based material including a combination of spider silk and a trans-membrane segment of human muscle L-type calcium channel (e.g., PEPGEL®), an amphiphilic 16 residue peptide containing a repeating arginine-alanine-aspartate-alanine sequence (RADARADARADARADA (SEQ ID NO:1)) (e.g., PURAMATRIX®), EAK16 (AEAEAKAKAEAEAKAK (SEQ ID NO:2)), KLD12 (KLDLKLDLKLDL (SEQ ID NO:3)), and PGMATRIX™.

In some embodiments, the matrix is uniform. In some embodiments, the matrix is non-uniform. In some embodiments, the biological sample is embedded in a uniform hydrogel matrix. In some embodiments, the biological sample is embedded in a gradient hydrogel. In some embodiments, the matrix can be configured to have an overall positive charge. In some embodiments, the matrix can be configured to have an overall negative charge. In some embodiments, the matrix includes a charge gradient. In some embodiments, the matrix can be configured to have various pore sizes. For example, a matrix having a larger pore size (e.g., larger average pore size) can allow one or more spatially-programmed capture probes to migrate (e.g., actively migrate or passively migrate) through the hydrogel more quickly and easily than an otherwise identical matrix having a smaller pore size (e.g., smaller average pore size). In some embodiments, one or more biological analytes of interest are cross-linked to the matrix.

In some instances, the biological sample is embedded in a gradient hydrogel. In some instances, the gradient is due to changing pore size in the hydrogel (e.g., from larger pore size to smaller pore size), allowing probes to diffuse through the hydrogel. A gradient can be synthesized by assembling a silicon sheet with two graphite electrodes. After assembly, a hydrogel composition as described herein is dispersed in between the two electrodes, and the hydrogel polymerizes over a period of time (e.g., for 24 hours) while being exposed to an electrical gradient. After exposure to an electrical gradient, a pore-size gradient can form along the direction of the electric field.

In some embodiments, the migration of the plurality of spatially-programmed capture probes includes thermophoresis, electrophoresis, magnetophoresis, or combinations thereof. In some embodiments, the migration of the plurality of spatially-programmed capture probes is performed using active migration. In some embodiments, active migration includes applying an electric field. In some embodiments, the electric field is dynamic. In some embodiments, the electric field is static. In some embodiments, active migration includes a applying a magnetic field. In some embodiments, the magnetic field is dynamic. In some embodiments, the magnetic field is static. In some embodiments, the migration of the plurality of spatially-programmed capture probes is performed using passive migration.

In some embodiments, more than one migration of a plurality of spatially-programmed capture probes is performed. In some embodiments, the migration of the plurality of spatially-programmed capture probes can be conducted along one or more dimensions of the matrix. In some embodiments, a migration of a plurality of spatially-programmed capture probes is first conducted along a first dimension of the matrix and then another migration of the plurality of spatially-programmed capture probes conducted along a second dimension of the matrix, wherein the first and second dimensions are perpendicular. In some embodiments, a migration of a plurality of spatially-programmed capture probes is conducted along a first dimension, a second dimension, and a third dimension of the matrix, wherein each dimension is perpendicular.

In some embodiments, the migrated plurality of spatially-programmed capture probes are immobilized in the matrix. In some embodiments, the migrated plurality of spatially-programmed capture probes are cross-linked to the matrix. In some embodiments, the migrated plurality of spatially-programmed capture probes are cross-linked to the matrix using UV crosslinkable moieties.

In some embodiments, the migrated plurality of spatially-programmed capture probes is used to determine the location of at least one biological analyte of interest. As an example, the spatially-programmed capture probes can migrate different distances within the matrix depending on the properties of the spatially-programmed capture probes and/or properties of the matrix as described above. The spatially-programmed capture probes can then be imaged via optical labeled probe and/or optical visualization domain, which is used to determine the location of the spatially-programmed capture probes in the matrix. Any of the variety of methods disclosed herein that can be used to identify the analyte, identify the location of the analyte, or otherwise analyze an analyte bound to a capture probe can be used. For example, if the spatially-programmed capture probes have bound to a biological analyte, sequencing can be used in combination with the imaging data to associate a biological analyte of interest from the plurality of biological analytes to a spatially-programmed capture probe and a location.

(e) Spatially Programmed Capture Probes

In some instances, the spatially-programmed capture probe can include one or more of (i) a programmable migration domain; (ii) a detectable moiety; and (iii) a capture domain that binds specifically to a sequence within the nucleic acid. In some instances, the spatially-programmed capture probe further include a cleavage domain, where upon cleavage of the cleavage domain, the programmable migration domain is released from the spatially-programmed capture probe. The release of the programmable migration domain can, e.g., allow for subsequent rapid migration of the extension product to the array. In some examples, cleaving the cleavage domain to release the programmable migration domain from the spatially-programmed capture probe can be performed between steps (e) and (f). In some examples, the cleavage domain can include a recognition sequence for a restriction endonuclease. In some examples, the spatially-programmed capture probe is an oligonucleotide probe.

Figure 8:
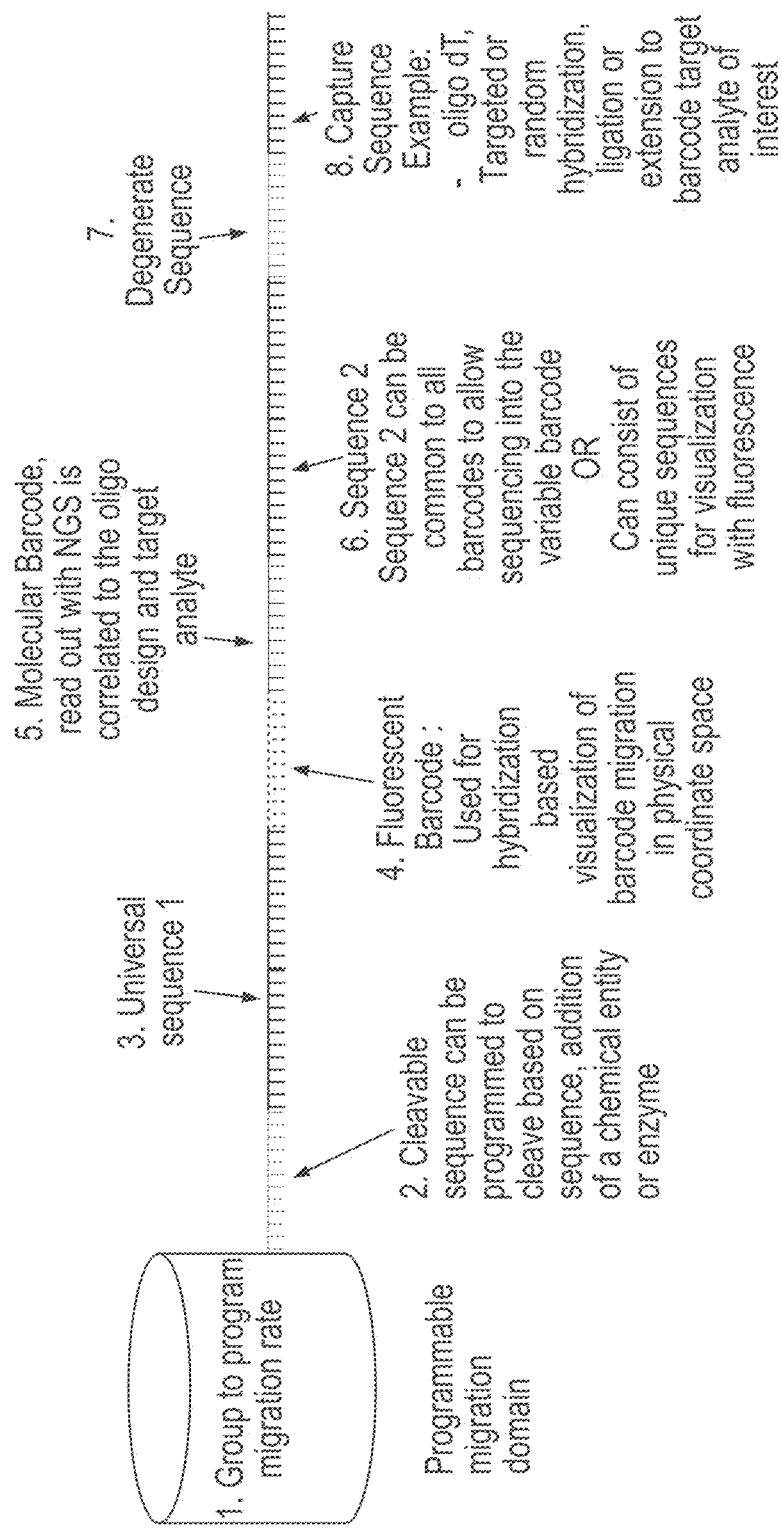
FIG. 8 is a schematic showing an exemplary spatially-programmed capture probe. As an example, a spatially-programmed capture probe can comprise a programmable migration domain, a cleavage domain, a first universal sequence, a barcode sequence for an optical labeled probe (e.g., a fluorescent barcode), a spatial barcode, a second universal sequence, a degenerate sequence, and a capture domain.

Referring to FIG. 8, the spatially-programmed capture probes as described herein can include one or more of a programmable migration domain, a cleavable sequence, an x-y spatial barcode (or molecular barcode), a fluorescent barcode that can be used to determine the z-location of the analyte, one or more of a universal probe sequence, a degenerate sequence, an additional barcode sequence (Sequence2), a capture sequence, and any combination thereof.

In some examples, the capture domain in the spatially-programmed capture probe can include an oligo(dT) sequence (e.g., an oligo(dT) sequence including about 5 to about 50 Ts, about 5 to about 45 Ts, about 5 to about 40 Ts, about 5 to about 35 Ts, about 5 to about 30 Ts, about 5 to about 25 Ts, about 5 to about 20 Ts, about 5 to about 15 Ts, about 5 to about 10 Ts, about 10 to about 50 Ts, about 10 to about 45 Ts, about 10 to about 40 Ts, about 10 to about 35 Ts, about 10 to about 30 Ts, about 10 to about 25 Ts, about 10 to about 20 Ts, about 10 to about 15 Ts, about 15 to about 50 Ts, about 15 to about 45 Ts, about 15 to about 40 Ts, about 15 to about 35 Ts, about 15 to about 30 Ts, about 15 to about 25 Ts, about 15 to about 20 Ts, about 20 to about 50 Ts, about 20 to about 45 Ts, about 20 to about 40 Ts, about 20 to about 35 Ts, about 20 to about 30 Ts, about 20 to about 25 Ts, about 25 to about 50 Ts, about 25 to about 45 Ts, about 25 to about 40 Ts, about 25 to about 35 Ts, about 25 to about 30 Ts, about 30 to about 50 Ts, about 30 to about 45 Ts, about 30 to about 40 Ts, about 30 to about 35 Ts, about 35 to about 50 Ts, about 35 to about 45 Ts, about 35 to about 40 Ts, about 40 to about 50 Ts, about 40 to about 45 Ts, or about 45 to about 50 Ts). In some examples, the migration of the spatially-programmed capture probe is performed using passive migration. In some examples, the migration of the spatially-programmed capture probe is performed using active migration (e.g., active migration performed using an electric field, a magnetic field, a charged gradient, or any combination thereof). In some examples, active migration can be performed using pulsed-field electrophoresis and/or rotating field electrophoresis. Additional methods for performing active migration are described herein, and are known in the art. In some examples, the migration of the spatially-programmed capture probe can be performed in a linear or a non-linear direction.

In some instances, the spatially-programmed capture probe is an oligonucleotide probe. In some instances, the spatially-programmed capture probe includes a DNA sequence. In some instances, the DNA sequence is single-stranded. In some instances, the spatially-programmed capture probe includes an RNA sequence.

For example, provided herein are spatially-programmed capture probes that include (i) a programmable migration domain (e.g., any of the exemplary programmable migration domains described herein), (ii) a detectable moiety (e.g., any of the exemplary detectable moieties described herein or known in the art), and (iii) a capture domain (e.g., any of the exemplary capture domains described herein) that binds specifically to a sequence within a nucleic acid analyte.

Also provided are pairs of spatially-programmed capture probes, where each pair includes a first and a second spatially-programmed capture probe, where: at least one of the first and the second spatially-programmed capture probe includes a detectable moiety (e.g., any of the exemplary detectable moieties described herein or known in the art), the first and second spatially-programmed probe, when hybridized to a nucleic acid analyte, are capable of being ligated together, and each of the first and the second spatially-programmed capture probes include a programmable migration domain (e.g., any of the programmable migration domains described herein).

As used herein, a "programmable migration domain" refers to an agent that can influence and/or control the migration rate of the capture probe. For example, the programmable migration domain can influence and/or control the rate of migration of the capture probe due to the charge, size, electromagnetic properties, or a combination thereof of the programmable migration domain. In some embodiments, the programmable migration domain includes a charged domain, a size-specific domain, an electromagnetic domain, or any combinations thereof. In some instances, the programmable migration domain can include a fluorescent tag or marker as disclosed herein.

A "charged domain," as used herein includes an agent that has a net positive or negative charge. In some instances, a charged domain includes a domain that has a charge at a portion of a domain. In some instances, a programmable migration domain is charged at one end and has no charge at another end. In some instances, a programmable migration domain is charged at both ends of the domain. For example, in some instances, a programmable migration domain has a negative charge at both ends of the domain. In some instances, a programmable migration domain has a positive charge at both ends of the domain. In some instances, the programmable migration domain has both negative and positive charges. In some instances, the programmable migration domain has a negative charge at one end and a positive charge at another end.

A "size-specific" domain as used herein refers to a programmable migration domain that differs from other programmable migration domains based on size of the domain. In some instances, the size-specific domain includes a moiety (e.g., as disclosed herein; e.g., a protein, a nucleic acid, a small molecule, and the like) that differs from other moieties in a programmable migration domain. In some embodiments, a size-specific domain can limit migration of the probe if the size of the programmable migration domain is increased. In some embodiments, a size-specific domain can increase migration of the probe if the size of the programmable migration domain is decreased in size.

An "electromagnetic" domain as used herein refers to a programmable migration domain that is able to migrate in a particular direction (e.g., through a dimension, or a dimension, in a three-dimensional area (e.g., in a biological sample)). In some instances, an electromagnetic or electric field (e.g., electrophoresis) is applied to a biological sample, allowing probes having electromagnetic domain to migrate to different areas of a biological sample based on differences in e.g., conductivity or charge.

In some instances, a programmable migration domain can have a hydrodynamic radius (Rh) or Stokes radius that modifies the diffusion of a spatially-programmed capture probe or any other molecule that includes the programmable migration domain. For example, a programmable migration domain can have an Rh of greater than about 1 nm, greater than about 10 nm, greater than about 20 nm, greater than about 40 nm, greater than about 60 nm, greater than about 80 nm, greater than about 100 nm, greater than about 200 nm, greater than about 300 nm, or greater than about 400 nm. In some examples, a programmable migration domain can have an Rh of about 1 nm to about 400 nm, about 1 nm to about 300 nm, about 1 nm to about 200 nm, about 1 nm to about 100 nm, about 1 nm to about 80 nm, about 1 nm to about 60 nm, about 1 nm to about 40 nm, about 1 nm to about 20 nm, about 1 nm to about 10 nm, about 1 nm to about 5 nm, about 10 nm to about 400 nm, about 10 nm to about 200 nm, about 10 nm to about 100 nm, about 10 nm to about 20 nm, about 20 nm to about 400 nm, about 20 nm to about 300 nm, about 20 nm to about 200 nm, about 20 nm to about 100 nm, about 100 nm to about 400 nm, about 100 nm to about 300 nm, about 100 nm to about 200 nm, about 100 nm to about 120 nm, about 200 nm to about 400 nm, about 200 nm to about 300 nm, about 200 nm to about 220 nm, about 300 nm to about 400 nm, about 300 nm to about 360 nm, about 300 nm to about 320 nm, about 360 nm to about 400 nm, about 360 nm to about 380 nm, or about 380 nm to about 400 nm.

In some examples, a programmable migration domain can be charged (e.g., have a net positive/negative charge at a neutral pH (e.g., a pH of about 6 to about 8, about 6.5 to about 7.5, or about 6.8 to about 7.2)) and/or have electromagnetic properties (e.g., magnetic or paramagnetic at a neutral pH (e.g., a pH of about 6 to about 8, about 6.5 to about 7.5, or about 6.8 to about 7.2)) that allow a spatially-programmed capture probe or any other molecule that includes the programmable migration domain to be actively migrated through a hydrogel matrix. Non-limiting aspects and examples of programmable migration domains are described herein.

In some embodiments, the programmable migration domain comprises a nucleic acid. In some embodiments, the programmable migration domain comprises an aptamer. In some embodiments, the programmable migration domain can be an aptamer designed to bind to a fluorophore. In some embodiments, the programmable migration domain is a folded nucleic acid (e.g., comprising at least one hairpin or double-stranded portion). In some embodiments, the programmable migration domain is a nucleic acid folded into a three-dimensional structure (e.g. square, cube, triangle, or sphere). See, e.g., Veneziano et al. Science, 352(6293), 1534-1534 (2016), which is incorporated herein by reference in its entirety.

In some embodiments, the programmable migration domain comprises an electromagnetic domain. In some embodiments, the programmable migration domain can be a metallic nanoparticle (see, e.g., Hanauer et al., Nano Lett. 2007; 7(9):2881-2885, which is incorporated herein by reference in its entirety). In some embodiments, the programmable migration domain is a metallic nanoparticle made of a magnetic material (e.g., iron, nickel, cobalt, and/or magnetite). In some embodiments, the programmable migration domain is a metallic nanoparticle made of a paramagnetic material (e.g., iron oxide, manganese, and/or gadolinium). In some embodiments, the programmable migration domain can be a metallic nanoparticle made of a non-magnetic material (e.g., polyethelene, aluminum, pyrite, and/or biotite). In some embodiments, the programmable migration domain can be a non-magnetic metallic nanoparticle that has been coated in a paramagnetic material and/or a magnetic material. In some embodiments, the programmable migration domain can be a magnetic metallic nanoparticle that has been coated in a paramagnetic material and/or a non-magnetic material. In some embodiments, the programmable migration domain can be a paramagnetic metallic nanoparticle that has been coated in a magnetic material and/or a non-magnetic material.

In some embodiments, the programmable migration domain can be a metallic nanoparticle that has been functionalized. In some embodiments, the programmable migration domain can be a metallic nanoparticle that has been functionalized with antibodies. In some embodiments, the programmable migration domain can be a metallic nanoparticle that has been functionalized with biotin, avidin, streptavidin, or a combination thereof. In some embodiments, the programmable migration domain can be a metallic nanoparticle that has been functionalized with one or more fluorophore (e.g., two or more, three or more, four or more). In some embodiments, the programmable migration domain is a small metallic nanoparticle (e.g., a diameter of 2 to 10 nm, 2 to 4 nm, 3 to 5 nm, 4 to 6 nm, 5 to 7 nm, 6 to 8 nm, 7 to 9 nm, or 8 to 10 nm). In some embodiments, the programmable migration domain can be a medium metallic nanoparticle (e.g., a diameter of 20 to 500 nm, 20 to 50, 51 to 100 nm, 101 to 150 nm, 151 to 200 nm, 201 to 250 nm, 251 to 300 nm, 301 to 350 nm, 351 to 400 nm, 401 to 450 nm, or 451 to 500 nm). In some embodiments, the programmable migration domain can be a large metallic nanoparticle (e.g., a diameter of 501 to 600 nm, 601 to 700 nm, 701 to 800 nm, 801 to 900 nm, 901 to 1000 nm, 1001 to 1100 nm, 1101 to 1200 nm, 1201 to 1300 nm, 1301 to 1400 nm, 1401 to 1500 nm, 1501 to 1600 nm, 1601 to 1700 nm, 1701 to 1800 nm, 1801 to 1900 nm, or 1901 to 2000 nm). In some embodiments, the programmable migration domain is a non-metallic nanoparticle (e.g., borosilicate glass, soda-lime glass, and/or barium titanate glass). In some embodiments, the programmable migration domain can be a non-metallic nanoparticle coated in a paramagnetic, magnetic, and/or non-magnetic material. See Wang et al., *Journal of Materials Science*, 47(16), 5946-5954.:5946-54 (2012), which is incorporated herein by reference in its entirety.

In some embodiments, the programmable migration domain can be a protein. In some embodiments, the programmable migration domain can be a protein comprising avidin, biotin, streptavidin, or a combination thereof. In some embodiments, the programmable migration domain can be a protein with one or more subunits (e.g., two or more, three or more, four or more, five or more, six or more, seven or more, eight or more, nine or more). In some embodiments, the programmable migration domain can be a protein with multiple subunits of the same net charge or different net charge (e.g., at a neutral pH (e.g., neutral pH (e.g., a pH of about 6 to about 8, about 6.5 to about 7.5, or about 6.8 to about 7.2)) (e.g., one charged subunit, two charged subunits, three charged subunits, four charged subunits) (see Heinová, D., Kostecká, Z., & Petrovová, E. (2018), Lactate Dehydrogenase Isoenzyme Electrophoretic Pattern in Serum and Tissues of Mammalian and Bird Origin. *Electrophoresis: Life Sciences Practical Applications*, 81, which is incorporated herein by reference in its entirety). In some embodiments, the programmable migration domain can be a protein that has been functionalized. In some embodiments, the programmable migration domain can be a protein that has been functionalized with antibodies. In some embodiments, the programmable migration domain can be a protein that has been functionalized with biotin, avidin, streptavidin, or a combination thereof. In some embodiments, the programmable migration domain can be a protein that has been functionalized with one or more fluorophore (e.g., two or more, three or more, four or more). In some embodiments, the programmable migration domain can be a protein that has been functionalized with polyethelyne glycol (PEG). In some embodiments, the programmable migration domain can be a protein that has been functionalized with branched PEG or linear PEG, or a combination thereof. In some embodiments, the programmable migration domain can be a protein that has been functionalized with PEG of a low molecular mass (e.g., 20 to 29 Daltons, 30 to 39 Daltons, 40 to 49 Daltons, 50 to 59 Daltons, 60 to 69 Daltons, 70 to 79 Daltons, 80 to 89 Daltons, or 90 to 100 Daltons). In some embodiments, the programmable migration domain can be a protein that has been functionalized with PEG of a medium molecular mass (e.g., 200 to 299 Daltons, 300 to 399 Daltons, 400 to 499 Daltons, 500 to 599 Daltons, 600 to 699 Daltons, 700 to 799 Daltons, 800 to 899 Daltons, or 900 to 1000 Daltons). In some embodiments, the programmable migration domain can be a protein that has been functionalized with a PEG (e.g., a PEG having a molecular mass of 2000 Daltons or more, 3000 Daltons or more, 4000 Daltons or more, 5000 Daltons or more, 6000 Daltons or more, 7000 Daltons or more, 8000 Daltons or more). See, e.g., Van Vught et al., *Computational and structural biotechnology journal,* 9(14) (2014), which is incorporated herein by reference in its entirety.

In some embodiments, the programmable migration domain can be a PEG. In some embodiments, the programmable migration domain can be a branched PEG or a linear PEG, or a combination thereof. In some embodiments, the programmable migration domain can include a PEG having a molecular mass of 20 to 29 Daltons, 30 to 39 Daltons, 40 to 49 Daltons, 50 to 59 Daltons, 60 to 69 Daltons, 70 to 79 Daltons, 80 to 89 Daltons, or 90 to 100 Daltons). In some embodiments, the programmable migration domain can be a PEG having a molecular mass of 200 to 299 Daltons, 300 to 399 Daltons, 400 to 499 Daltons, 500 to 599 Daltons, 600 to 699 Daltons, 700 to 799 Daltons, 800 to 899 Daltons, or 900 to 1000 Daltons. In some embodiments, the programmable migration domain can be a PEG having a molecular mass of 2000 Daltons or more, 3000 Daltons or more, 4000 Daltons or more, 5000 Daltons or more, 6000 Daltons or more, 7000 Daltons or more, 8000 Daltons or more.

In some embodiments, a programmable migration domain can include a polymer (e.g., polyvinyl alcohol, poly(ethylene glycol), poly(N-2-hydroxypropyl methacrylamide), poly(N-isopropylacrylamide), a polyphosphazene, a polyanhydride, a polyacetal, a poly(ortho ester), a polyphosphoester, a polycaprolactone, a polyurethane, a polylactide, a polycarbonate, a polyamide, poly(alpha-ester), or poly(lactide-co-glycolide)(PLGA), or any combination thereof). See, e.g., Ulery et al., *J Polym. Sci. B Polym. Phys.* 49(12): 832-864, 2011.

In some instances, the spatially-programmed capture probe includes a detectable moiety (e.g., one or more of any of the detectable moieties described herein). In some instances, the spatially-programmed capture probe includes more than one detectable moiety. In some instances, the detectable moiety is a fluorescent moiety. In some instances, the detectable moiety is a luminescent moiety or a chemiluminescent moiety and includes, but is not limited to, peroxidases such as horseradish peroxidase (HRP), soybean peroxidase (SP), alkaline phosphatase, and luciferase.

In some embodiments, a spatially-programmed capture probe can further includes one or more functional domains. In some instances, the functional domain is a primer sequence. In some embodiments, a spatially-programmed capture probe can include a first functional domain. In some embodiments, a spatially-programmed capture probe can further include a second functional domain. In some embodiments, the first functional domain can include a first universal sequence. For example, a first universal sequence common to a plurality of spatially-programmed capture probes. In some embodiments, the second functional domain can include a second universal sequence. For example, a second universal sequence common to a plurality of spatially-programmed capture probes. In some embodiments, a first functional domain or a first universal sequence is different from a second functional domain or a second universal sequence. In some embodiments, the second universal domain includes a sequence for initiating a sequencing reaction, a sequence for optical visualization, or a combination thereof. In some embodiments, the sequencing reaction is a sequencing-by-synthesis reaction.

In some embodiments, a spatially-programmed capture probe can further include a barcode sequence for an optical labeled probe. In some embodiments, the sequence for a barcode sequence for an optical labeled probe is configured to hybridize to the sequence of an optical labeled probe. In some embodiments, an optical labeled probe includes a fluorescent tag or agent. In some embodiments, a spatially-programmed capture probe includes an optical visualization domain. In some embodiments, an optical visualization domain includes a fluorescent agent. In some embodiments, an optical labeled probe and/or optical visualization domain is imaged within a matrix immobilizing the biological sample. In some embodiments, the imaging of the optical labeled probe and/or optical visualization is used to determine the migration of the associated spatially-programmed capture probe in the matrix.

In some embodiments, a spatially-programmed capture probe can further include a spatial barcode as described herein. In some instances, the spatial barcode provides a unique sequence that is associated with a location in a biological sample. In some embodiments, a spatially-programmed capture probe can further includes one or more UMI (or "degenerate sequence(s)"). In some embodiments, the UMI or degenerate sequence domain includes a nucleic acid sequence that is configured to determine a total number of capture probes.

In some embodiments, a spatially-programmed capture probe can further include a cleavage domain, as described herein. In some embodiments, the cleavage domain includes a sequence that can be programed to cleave based on the sequence. In some embodiments, upon cleavage of the cleavage domain, the programmable migration domain is released from the spatially-programmed capture probe. In some instances, the cleavage domain comprises a recognition sequence for a restriction endonuclease (i.e., a restriction enzyme). In some instances, for example, the cleavage domain can include a restriction endonuclease recognition sequence.

In some embodiments, a spatially-programmed capture probe includes a capture domain, e.g., any of the exemplary capture domains described herein. In some embodiments, the capture domain includes a poly dT (e.g., an oligo (dT)) sequence. In some embodiments, the capture domain includes a sequence that is substantially complementary (e.g., at least 70%, at least 75%, at least 80%, at least 90%, at least 91%, at least 92%, at least 93%, at least 94%, at least 95%, at least 96%, at least 97%, at least 98%, or at least 99% or higher) to a nucleic acid sequence present in or associated with a biological analyte. In some embodiments, the capture domain includes a sequence that is fully complementary to a nucleic acid sequence present in or associated with a nucleic acid analyte. In some embodiments, the capture domain includes a sequence that is substantially complementary (e.g., at least 70%, at least 75%, at least 80%, at least 90%, at least 91%, at least 92%, at least 93%, at least 94%, at least 95%, at least 96%, at least 97%, at least 98%, at least 99% or higher) to one or more particular target sequence(s) of interest. In some embodiments, the capture domain includes a sequence that is fully complementary to one or more particular target sequence(s) of interest.

In some embodiments, a spatially-programmed capture probe includes (i) a programmable migration domain (e.g., any of the exemplary programmable migration domain described herein); (ii) a detectable moiety (e.g., one or more of any of the exemplary detectable moieties described herein); and (iii) a capture domain (e.g., any of the exemplary capture domains described herein) that binds specifically to a sequence within a nucleic acid analyte. In some instances, the disclosure includes the use of a pair of spatially-programmed capture probes including a first and a second spatially-programmed capture probe, wherein at least one of the first and the second spatially-programmed capture probe comprises a detectable moiety (e.g., one or more of any of the exemplary detectable moieties described herein); the first and the second spatially-programmed capture probe, when hybridized to a nucleic acid analyte, are capable of being ligated together; and each of the first and the second spatially-programmed capture probes comprise a programmable migration domain (e.g., any of the exemplary programmable migration domains described herein).

In some embodiments, a spatially-programmed capture probe includes: (a) a programmable migration domain; (b) a first functional domain; (c) a barcode sequence for an optical labeled probe; and (d) a capture domain. In some embodiments, the spatially-programmed capture probe further includes one or more of the following: (a) a spatial barcode; (b) a cleavage domain; (c) a second functional domain; and (d) a UMI or degenerate sequence domain. In some embodiments, the first functional domain is a first universal sequence domain. For example, a first sequence common to a plurality of spatially-programmed capture probes. In some embodiments, the second functional domain is a second universal sequence. For example, a second sequence common to a plurality of spatially-programmed capture probes. In some embodiments, a first functional domain or a first universal sequence is different from a second functional domain or a second universal sequence.

In some embodiments, a spatially-programmed capture probes includes: (a) a programmable migration domain; (b) a first universal functional domain; (c) an optical visualization domain; (d) a spatial barcode; and (e) a capture domain. In some embodiments, the spatially-programmed capture probe further includes one or more of the following: (a) a cleavage domain; (b) a second universal functional domain; and (c) a UMI or degenerate sequence domain.

For example, in some instances, the detectable moiety is a luminescent moiety or a chemiluminescent moiety and includes but is not limited to peroxidases such as horseradish peroxidase (HRP), soybean peroxidase (SP), alkaline phosphatase, and luciferase.

Z-Dimensional Capture Probes

In some embodiments, the methods provided herein include introducing to a biological sample (or a matrix including a biological sample) one or a plurality of spatially-programmed capture probe and can be called z-dimensional capture probes. In some embodiments, the z-dimensional capture probe(s) can be any of the capture probes described herein. In some embodiments, z-dimensional capture probe(s) include a hybridization domain (e.g. any of the hybridization domains described herein), a z-dimensional barcode (e.g. any of the barcodes described herein), and a capture domain (e.g. any of the capture domains described herein).

In some embodiments, the z-dimensional capture probe(s) are migrated through the biological sample (or a matrix including a biological sample) in one or more directions. In some embodiments, the z-dimensional capture probe(s) are migrated through the biological sample (or a matrix including a biological sample) in one direction. In some embodiments, one or more z-dimensional capture probes migrate to distinct migration positions in the biological sample. In some embodiments, one or more z-dimensional capture probes migrate to migration positions in proximity with each other. In some embodiments, migrating the z-dimensional capture probe(s) includes applying a force (e.g. mechanical, centrifugal or electromagnetic) to the biological sample to facilitate migration of the capture probe(s) into and/or through the biological sample.

In some embodiments, a biological sample (or a matrix including a biological sample) is treated with one or more reagents to facilitate migration of z-dimensional capture probe(s). For example, an organic solvent (e.g., methanol or acetone) may be used to permeabilize cells of a biological sample. For example, a detergent (e.g., saponin, Triton X-100™ or Tween-20™) may be used to permeabilize cells of a biological sample. In another example, an enzyme (e.g., trypsin) may be used to permeabilize cells of a biological sample. Methods for cellular permeabilization are known in the art (see, e.g., Jamur and Oliver, Method Mol. Biol., 2010, 588:63-66). Any variety of suitable method of cell permeabilization may be used to practice the methods disclosed herein. In some embodiments, a biological sample is incubated with a cellular permeabilization reagent after introducing the z-dimensional capture probe(s) to the biological sample.

In some embodiments, migrating the z-dimensional capture probe(s) into or through a biological sample includes passive migration (e.g., diffusion). In some embodiments, migrating the z-dimensional capture probe(s) into or through a biological sample includes active migration (e.g., electrophoretic migration). In some embodiments, markers (e.g., upper and lower markers) along the direction of migration can be used to determine the migration limits of the z-dimensional capture probe(s). In some embodiments, the markers can include one or more detectable moieties as described herein.

In some embodiments, migrating the z-dimensional capture probe(s) into or through a biological sample includes use of a cell-penetrating agent. A "cell-penetrating agent" as used herein refers to an agent capable of facilitating the introduction of a capture probe into a cell of a biological sample (see, e.g., Lovatt et al. Nat Methods. 2014 February; 11(2):190-6, which is incorporated herein by reference in its entirety). In some embodiments, a cell-penetrating agent is a cell-penetrating peptide. A "cell-penetrating peptide" as used herein refers to a short peptide, e.g., usually not exceeding 30 residues, that have the capacity to cross cellular membranes.

In some embodiments, a cell-penetrating peptide may cross a cellular membrane using an energy-dependent or an energy-independent mechanism. For example, a cell-penetrating peptide may cross a cellular membrane through direct translocation through physical perturbation of the plasma membrane, endocytosis, adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS—Phosducin—like protein C terminus), Cys(Npys) antennapedia, Cys(Npys)-(Arg)9, Cys(Npys)-TAT (47-57), HIV-1 Tat (48-60), KALA, mastoparan, penetratin-Arg, pep-1-cysteamine, TAT(47-57)GGG-Cys(Npys), Tat-NR2Bct, transdermal peptide, SynB1, SynB3, PTD-4, PTD-5, FHV Coat-(35-49), BMV Gag-(7-25), HTLV-II Rex-(4-16), R9-tat, SBP, FBP, MPG, MPG(ΔNLS), Pep-2, and a polylysine peptide (see, e.g., Bechara et al. FEBS Lett. 2013 Jun. 19; 587(12):1693-702, which is incorporated by reference herein in its entirety.) In some embodiments, migrating the z-dimensional capture probe(s) into or through a biological sample includes use of an antibody and/or viral transfection.

In some embodiments, the z-dimensional location of a migrated z-dimensional capture probe is determined after migration. Any of the variety of techniques described herein or otherwise known in the art can be used to determine the z-dimensional location of a migrated z-dimensional capture probe. For example, imaging (e.g., any of the variety of imaging techniques described herein) can be used to determine the z-dimensional location of a migrated z-dimensional capture probe. In some embodiments, a z-dimensional capture probe includes one or more optical labels, which can be detected by imaging. In some embodiments, an imaging apparatus can be used to determine the z-dimensional location of a migrated z-dimensional capture probe, which imaging apparatus is able to image an intact biological sample (e.g., an intact biological sample, e.g., a matrix that includes the biological sample, through which a z-dimensional capture probe has been migrated). In some embodiments, the imaging employs confocal microscopy. In some embodiments, the imaging apparatus used to determine the z-dimensional location of a migrated z-dimensional capture probe is a confocal microscope.

(f) Capture of the Three-Dimensional Probe on a Substrate

In some embodiments, the methods provided herein include contacting the biological sample with a solid substrate (e.g., support) including a plurality of probes (e.g., also called x-y dimensional capture probes). In some embodiments, the x and y dimensions form a plane that is at an angle with the z dimension. In some embodiments, the angle is at least 10 degrees, 20 degrees, 30 degrees, 40 degrees, 50 degrees, 60 degrees, 70 degrees, 80 degrees or 90 degrees. In some embodiments, the angle is about 90 degrees. In some embodiments, the angle is 90 degrees. In some embodiments, the x-y dimensional capture probes can be any of the capture probes described herein. In some embodiments, an x-y dimensional capture probe can interact with a z-dimensional capture probe that is migrates to an array that includes the x-y dimensional capture probe such that the x-y dimensional capture probe associates with the z-dimensional capture probe. In some embodiments, a z-dimensional capture probe that interacts with an x-y dimensional capture probe on an array is associated with an analyte from the biological sample (e.g., the z-dimensional capture probe can capture the analyte before migrating to and interacting with the x-y dimensional capture probe). In some embodiments, the x-y dimensional capture probe(s) include a hybridization domain (e.g. any of the hybridization domains described herein) and an x-y dimensional barcode (e.g. any of the barcodes described herein). In some embodiments, the z-dimensional capture probe(s) (e.g. any of the z-dimensional capture probes described herein) may hybridize with the x-y dimensional capture probes through the one or more hybridization domains.

In some instances, a reverse transcriptase (e.g., any reverse transcriptase disclosed herein) is added to the hydrogel matrix. In some instances, reverse transcription is performed in situ on the biological sample, before adding the spatially-programmed capture probes to the sample.

In some instances, after hybridization of the spatially-programmed capture probe to the analyte, the 3' end of the spatially-programmed capture probe is extended using the nucleic acid as a template, to generate an extension product.

Figure 17:
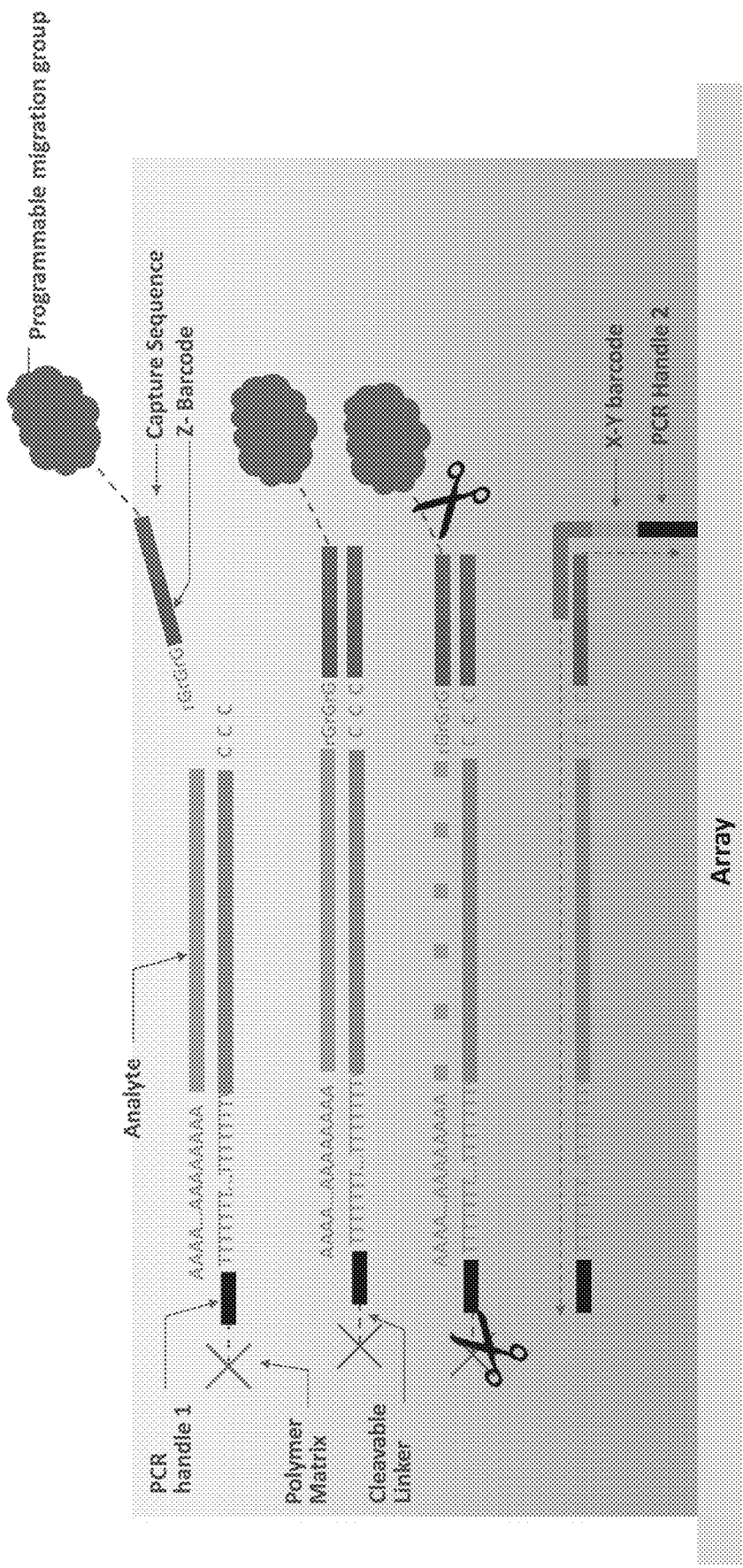
FIG. 17 shows an embodiment of the disclosure providing hybridization and capture of an analyte.

In some instances, as shown in FIG. 17, the programmable migration domain of the spatially-programmed capture probe is cleaved prior to migration of the spatially-programmed capture probe to the array. In some instances where a spatially-programmed capture probe has a cleavable linker, the spatially-programmed capture probe is cleaved at the cleavable linker prior to migration of the spatially-programmed capture probe to the array.

In some examples, the method also include includes sequencing (i) all or a part of the sequence in the extension product that is not present in the spatially-programmed capture probe, or a complement thereof, and (ii) all or a part of the sequence of the spatial barcode, or a complement thereof. Any of the non-limiting methods for sequencing a nucleic acid sequence described herein or known in the art can be used in step (g). For example, the sequencing can be performed using sequencing-by-synthesis (SBS), sequential fluorescence hybridization, sequencing by ligation, nucleic acid hybridization, or high-throughput digital sequencing techniques.

As a non-liming example, one or more of the z-dimensional capture probes can migrate through the biological sample (or a matrix including a biological sample) in one or more directions, the migrated z-dimensional capture probes can interact with (e.g. bind to or hybridize to) analytes, the z-dimensional capture probes can then migrate to a spatial array (e.g., a substrate that includes a plurality of x-y dimensional capture probes), and spatial analysis can be performed according to any of the variety of methods described herein.

In some instances, the spatially-programmed capture probes bind to the capture probe on the array. In some instances, binding is accomplished through hybridization (e.g., hybridization of the spatially-programmed capture probes to the capture domain of the capture probe).

In some instances, binding is accomplished through ligation (e.g., ligation of the spatially-programmed capture probes to the capture probe). In instances of ligation, a splint oligonucleotide can be used. In some instances, binding is accomplished through hybridization (e.g., hybridization of the spatially-programmed capture probes to the capture domain of the capture probe) followed by extension or reverse transcription.

In such an exemplary method, the three-dimensional location of the analytes in the biological sample can be determined. For example, in some instances, the capture probes (hybridized/associated with the spatially-programmed capture probes) are cleaved and prepared for next-generation sequencing using known library preparation methods. In some instances, the spatial barcodes on the spatially-programmed capture probes and the capture probe are correlated with spatial positions using spatial locations.

In some instances, the peak fluorescence from different migration depths can be measured using imaging and correlated with barcodes from spatially-programmed capture probes resulting from sequencing techniques.

Capture of Analytes and Spatially-Programmed Capture Probes

In some embodiments, a z-dimensional capture probe can capture an analyte via ligation. For example, a z-dimensional capture probe including a programmable migration domain can be migrated through a biological sample (e.g., a matrix including a biological sample) to a given location and an analyte can be ligated to the migrated z-dimensional capture probe. In some embodiments, the analyte is ligated to the migrated z-dimensional capture probe via use of a splint oligonucleotide (e.g., any of the variety of splint oligonucleotides described herein). In some embodiments, the analyte is ligated to the migrated z-dimensional capture probe without use of a splint oligonucleotide. In some embodiments, the analyte is a nucleic acid (e.g., DNA or RNA). In some embodiments, once an analyte is ligated to a z-dimensional capture probe, the ligated analyte/z-dimensional capture probe is migrated to a substrate that includes a plurality of x-y dimensional capture probes. In some embodiments, active migration is used to migrate the ligated analyte/z-dimensional capture probe to the substrate. In some embodiments, passive migration is used to migrate the ligated analyte/z-dimensional capture probe to the substrate. In some embodiments, an x-y dimensional capture probe can interact with a ligated analyte/z-dimensional capture probe that is migrated to an array that includes the x-y dimensional capture probe such that the x-y dimensional capture probe associates with the ligated analyte/z-dimensional capture probe. In some embodiments, the x-y dimensional capture probe is ligated to the ligated analyte/z-dimensional capture probe. In some embodiments, the x-y dimensional capture probe is ligated to the ligated analyte/z-dimensional capture probe via use of a splint oligonucleotide (e.g., any of the variety of splint oligonucleotides described herein). In some embodiments, the x-y dimensional capture probe is ligated to the ligated analyte/z-dimensional capture probe without use of a splint oligonucleotide. In some embodiments, the ligated analyte/z-dimensional capture probe/x-y dimensional capture probe is released from the substrate for further analysis (e.g., via cleavage). In some embodiments, the ligated analyte/z-dimensional capture probe/x-y dimensional capture probe is amplified prior to release. In some embodiments, the amplified analyte/z-dimensional capture probe/x-y dimensional capture probe is released from the substrate. In some embodiments, the x-y dimensional capture probe is hybridized to the ligated analyte/z-dimensional capture probe. In some embodiments, the z-dimensional capture probe is used as a template for polymerase-based extension of the x-y dimensional capture probe. In some embodiments, the polymerized product is released from the substrate (e.g., via cleavage) for further analysis. In some embodiments, polymerized product is amplified prior to release, and the amplified products are released.

In some embodiments, a z-dimensional capture probe can capture an analyte via hybridization. For example, a z-dimensional capture probe including a programmable migration domain including a programmable migration domain can be migrated through a biological sample (e.g., a matrix including a biological sample) to a given location and an analyte can be hybridized to the migrated z-dimensional capture probe. In some embodiments, the analyte is a nucleic acid (e.g., DNA or RNA). In some embodiments, once an analyte is hybridized to a z-dimensional capture probe, the hybridized analyte/z-dimensional capture probe is migrated to a substrate that includes a plurality of x-y dimensional capture probes. In some embodiments, active migration is used to migrate the hybridized analyte/z-dimensional capture probe to the substrate. In some embodiments, passive migration is used to migrate the hybridized analyte/z-dimensional capture probe to the substrate. In some embodiments, an x-y dimensional capture probe can interact with a ligated analyte/z-dimensional capture probe that is migrated to an array that includes the x-y dimensional capture probe such that the x-y dimensional capture probe associates with the ligated analyte/z-dimensional capture probe. In some embodiments, the x-y dimensional capture probe is ligated to the hybridized analyte/z-dimensional capture probe. In some embodiments, the x-y dimensional capture probe is ligated to the hybridized analyte/z-dimensional capture probe via use of a splint oligonucleotide (e.g., any of the variety of splint oligonucleotides described herein). In some embodiments, the x-y dimensional capture probe is ligated to the hybridized analyte/z-dimensional capture probe without use of a splint oligonucleotide. In some embodiments, the hybridized analyte/z-dimensional capture probe/x-y dimensional capture probe is released from the substrate for further analysis (e.g., via cleavage). In some embodiments, the hybridized analyte/z-dimensional capture probe/x-y dimensional capture probe is amplified prior to release. In some embodiments, the amplified analyte/z-dimensional capture probe/x-y dimensional capture probe is released from the substrate. In some embodiments, the x-y dimensional capture probe is hybridized to the hybridized analyte/z-dimensional capture probe. In some embodiments, the z-dimensional capture probe is used as a template for polymerase-based extension of the x-y dimensional capture probe. In some embodiments, the polymerized product is released from the substrate (e.g., via cleavage) for further analysis. In some embodiments, polymerized product is amplified prior to release, and the amplified products are released.

In some embodiments, further analysis of the analyte, the z-dimensional capture probe, and/or the x-y dimensional capture probe includes sequencing (e.g., any of the variety of sequencing methods described herein). In some embodiments, sequencing reveals that a given analyte that is associated with (e.g., is bound to or interacts with) a z-dimensional capture probe is associated with (e.g., is bound to or interacts with) a given x-y dimensional capture probe, thus identifying the three-dimensional location of the analyte in a biological sample. In some embodiments, sequencing is performed away from, or off, the substrate (e.g., after releasing the analyte, the z-dimensional capture probe, and/or the x-y dimensional capture probe from the substrate) according to any of the variety of sequencing methods described herein. In some embodiments, sequencing is performed in situ on the substrate (e.g., without releasing the analyte, the z-dimensional capture probe, and/or the x-y dimensional capture probe from the substrate). Any of a variety of in situ sequencing methods can be used. Non-limiting examples of in-situ sequencing include sequencing-by-ligation, and sequencing-by-hybridization (e.g., any of the variety of sequencing-by-ligation, and sequencing-by-hybridization methods described herein or otherwise known in the art).

(g) Proximity Capture Reactions

A "proximity capture reaction" as used herein refers to a reaction that detects two analytes that are spatially close (e.g., in proximity, or close in space) to each other and/or interacting with each other. For example, a proximity capture reaction can be used to detect sequences of DNA that are close in space to each other, e.g., the DNA sequences may be within the same chromosome, but separated by about 700 bp or less. As another example, a proximity capture reaction can be used to detect protein associations, e.g., two proteins that interact with each other. A proximity capture reaction can be performed in situ to detect two analytes (e.g., DNA and a protein, or RNA and a protein) that are spatially close to each other and/or interacting with each other inside a cell. For example, a proximity capture reaction can be used to detect nucleic acid-protein associations, e.g., where one analyte is a DNA or RNA molecule and one analyte is a protein. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). See, e.g., Miele and Dekker. Methods Mol Biol. 2009, 464; Simonis et al. Nat Genet. 2006, 38(11):1348-54; Raab et al. EMBO J. 2012 Jan. 18; 31(2): 330-350; and Eagen. Trends Biochem Sci. 2018 June; 43(6):469-478; each of which is incorporated herein by reference in its entirety. Other examples and methods that can be used in any of the variety of proximity capture methods described herein can be found in: Kolovos, P. et al. Investigation of the spatial structure and interactions of the genome at sub-kilobase-pair resolution using T2C. Nat. Protoc. 13, 459-477 (2018), Davies, J. O. J., Oudelaar, A. M., Higgs, D. R. & Hughes, J. R. How best to identify chromosomal 10 interactions: a comparison of approaches. Nat. Methods 14, 125-134 (2017). Mishra, A. & Hawkins, R. D. Three-dimensional genome architecture and emerging technologies: looping in disease. Genome Med. 9, 87 (2017), Han, J., Zhang, Z. & Wang, K. 3C and 3C-based techniques: the powerful tools for spatial genome organization deciphering. Mol. Cytogenet. 11, 21 (2018), Schaus, T. E., Woo, S., Xuan, F., Chen, X. & Yin, P. A DNA nanoscope via auto-cycling proximity recording. Nat. Commun. 8, 696 (2017), Boulgakov, A. A., Xiong, E., Bhadra, S., Ellington, A. D. & Marcotte, E. M. From Space to Sequence and Back Again: Iterative DNA Proximity Ligation and its Applications to DNA-Based Imaging. BioRxiv (2018). doi:10.1101/470211, and Weinstein, J. A., Regev, A. & Zhang, F. DNA microscopy: Optics-free spatio-genetic imaging by a stand-alone chemical reaction. BioRxiv (2018), doi:10.1101/471219, each of which is incorporated herein by reference in its entirety.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each, e.g., by binding the same target protein (complex), and the DNA ligation products that form are then used to template PCR amplification. See, e.g., Soderberg et al., Methods. 2008 July; 45(3):227-32. In some embodiments, proximity ligation can include chromosome conformation capture methods.

In some embodiments, the proximity capture reaction is performed on analytes within about 400 nm distance from each other. For example, the proximity capture reaction is performed on analytes within about 350 nm, about 300 nm, about 250 nm, about 225 nm, about 200 nm, about 175 nm, about 150 nm, about 125 nm, about 100 nm, about 75 nm, about 50 nm, about 25 nm, about 10 nm, or about 5 nm distance from each other. In some embodiments, the proximity capture reaction is irreversible. In some embodiments, the proximity capture reaction is reversible.

In some embodiments, a proximity capture reaction generates a plurality of proximally-associated biological analyte pairs, members of which are captured on a solid substrate (e.g., any of the variety of solid substrates described herein) including a plurality of capture probes (e.g., any of the variety of capture probes described herein). In some embodiments, capture probes on the solid substrate capture proximally-associated biological analyte pairs. In some embodiments, the 2-dimensional spatial profile of the one or more captured proximally-associated analyte pairs in the biological sample is determined (e.g., via any of the variety of methods for determining the spatial profile of analytes described herein). In some embodiments, the 3-dimensional spatial profile of biological analytes in the biological sample is determined by analyzing: 1) the 2-dimensional spatial profile of the one or more captured proximally-associated analyte pairs, and 2) the determined identities of the biological analytes of one or more proximally-associated biological analyte pairs.

In some embodiments, a proximity capture reaction followed by 2-dimensional spatial analysis can reveal information about analytes in a biological sample that 2-dimensional spatial analysis cannot reveal. When the two analytes are determined to be present in the biological sample at a given x-y coordinate or location, analysis of a proximity capture reaction can determine whether the two analytes are also present at a given z coordinate or location (e.g., whether the two analytes are proximal or spatially close in the biological sample). For example, two analytes in a biological sample can be subjected to a proximity capture reaction (e.g., any of the variety of proximity capture reactions described herein) such that they will interact if they are proximal to each other but will not interact if they are not proximal to each other, captured on a substrate (e.g. a spatial array that includes a plurality of spatially barcoded capture probes), and analyzed. When the 2-dimensional spatial analysis using the spatial array reveals that the two analytes are present at the same x-y coordinate or x-y location in the biological sample, whether or not the proximity capture reaction results in the two analytes interacting with each other can reveal whether the two analytes are proximal to each other in the biological sample, or whether they are not proximal to each other (e.g., in the z dimension) in the biological sample.

The results of a plurality of proximity capture reactions can be used to determine the relative proximity of three or more analytes in a biological sample. For example, when 2-dimensional spatial analysis using a spatial array reveals that the three analytes are present at the same x-y coordinate or x-y location in the biological sample, the results of a plurality of proximity capture reactions can reveal whether the three analytes are proximal to or near each other in three-dimensional space. In some embodiments, the results of a plurality of proximity capture reactions will reveal that the three analytes are proximal to or near each other in three-dimensional space (e.g., a first proximity capture reaction can show that the first and second analytes are near each other, a second proximity capture reaction can show that the second and third analytes are near each other, and a third proximity capture reaction can show that the first and third analytes are near each other, revealing that all three analytes are proximal to or near to each other.) In some embodiments, the results of a plurality of proximity capture reactions will reveal that only two of the three analytes are proximal to or near each other in three-dimensional space (e.g., a first proximity capture reaction can show that the first and second analytes are near each other, a second proximity capture reaction can show that the second and third analytes are not near each other, and a third proximity capture reaction can show that the first and third analytes are not near each other, revealing that only the first two analytes are proximal to or near to each other). In some embodiments, the results of a plurality of proximity capture reactions will reveal that only one of the three analytes is proximal to or near to the other two analytes in three-dimensional space, but that the other two analytes are not proximal to each other in three-dimensional space (e.g., a first proximity capture reaction can show that the first and second analytes are near each other, a second proximity capture reaction can show that the second and third analytes are near each other, and a third proximity capture reaction can show that the first and third analytes are not near each other, revealing that the second analyte is proximal to or near the first and third analytes, but that the first and third analytes are not proximal to or near each other, e.g., the second analyte is located between the first and third analytes in three-dimensional space.)

In some embodiments, a proximity capture reaction(s) as disclosed herein is used to increase effective resolution of three-dimensional analyte detection. FIG. 12 is a schematic showing how a 2D array can be used in 3D reconstruction of subcellular geometries at each voxel. The scales of x and y are in mm, and the scales of X", Y", and Z" are in nm. As shown in exemplary FIG. 11, use of proximity capture reaction(s) in combination with a 2-dimensional spatial array can be used to increase the resolution of three-dimensional analyte detection. A proximity capture reaction(s) can be used to bind or otherwise associate analytes that are proximal to each other in a biological sample to generate proximally-associated biological analyte pairs prior to capture of the proximally-associated biological analyte pairs on a 2-dimensional spatial array. In exemplary FIG. 11, five spatially-programmed capture probes 1100 are migrated into the migration matrix and undergo proximity capture reaction(s) to bind to target biological analytes within the migration matrix. In some embodiments, by analyzing the various proximally-associated biological analyte pairs, a 3-dimensional map of the analytes can be reconstructed, and the effective resolution of the three-dimensional analyte reconstruction is increased beyond the resolution of the 2-dimensional array used in the analysis.

In some embodiments, use of proximity capture reaction(s) increases resolution from a multi-cellular scale to a cellular scale (e.g., single-cell resolution) compared to resolution without the proximity capture reaction(s). In some embodiments, use of proximity capture reaction(s) increases resolution from a cellular scale to a subcellular scale compared to resolution without the proximity capture reaction(s). In some embodiments, resolution increases to detect analytes in organelles in a cell. For example, in some embodiments, resolution increases to detect a subcellular region including but not limited to cytosol, a mitochondria, a nucleus, a nucleolus, an endoplasmic reticulum, a lysosome, a vesicle, a Golgi apparatus, a plastid, a vacuole, a ribosome, cytoskeleton, or combinations thereof. In some embodiments, the subcellular region comprises at least one of cytosol, a nucleus, a mitochondria, and a microsome. In some embodiments, the subcellular region is cytosol. In some embodiments, the subcellular region is a nucleus. In some embodiments, the subcellular region is a mitochondria. In some embodiments, the subcellular region is a microsome.

In some embodiments, use of a proximity capture reaction(s) increases three-dimensional resolution from a micrometer scale to a nanometer scale compared to three-dimensional resolution without the proximity capture reaction(s). In some embodiments, resolution increases by about 1.1-fold, by about 1.2-fold, by about 1.3-fold, by about 1.4-fold, by about 1.5-fold, by about 1.6-fold, by about 1.7-fold, by about 1.8-fold, by about 1.9-fold, by about 2-fold, by about 3-fold, by about 4-fold, by about 5-fold, by about 6-fold, by about 7-fold, by about 8-fold, by about 9-fold, by about 10-fold, by about 20-fold, by about 30-fold, by about 40-fold, by about 50-fold, by about 100-fold, by about 200-fold, by about 300-fold, by about 400-fold, by about 500-fold, by about 600-fold, by about 700-fold, by about 800-fold, by about 900-fold, by about 1,000-fold, by about 10,000-fold, or by any amount between these values. In some embodiments, resolution of analyte capture using a proximity capture reaction(s) in three-dimensional spatial analysis as disclosed herein increases resolution by about 1 nm, by about 5 nm, by about 10 nm, by about 15 nm, by about 20 nm, by about 25 nm, by about 30 nm, by about 35 nm, by about 40 nm, by about 45 nm, by about 50 nm, by about 55 nm, by about 60 nm, by about 65 nm, by about 70 nm, by about 75 nm, by about 80 nm, by about 85 nm, by about 90 nm, by about 95 nm, by about 100 nm, by about 150 nm, by about 200 nm, by about 250 nm, by 10 about 300 nm, by about 350 nm, by about 400 nm, by about 450 nm, by about 500 nm, by about 550 nm, by about 600 nm, by about 650 nm, by about 700 nm, by about 750 nm, by about 800 nm, by about 850 nm, by about 900 nm, by about 950 nm, or by about 1.0 μm compared to resolution without the proximity capture reaction(s).

In some embodiments, following proximity capture, the proximally-associated biological 15 analyte pairs are migrated (e.g., actively or passively) to a substrate having a plurality of capture probes. In some embodiments, such capture probes are capable of binding proximally-associated biological analyte pairs, but lack an x-y barcode. In some embodiments, by analyzing the various proximally-associated biological analyte pairs, a 3-dimensional map of the analytes can be reconstructed. In some embodiments, a 3-dimensional map of the analytes of the proximally-associated biological analyte pairs can be reconstructed even without the benefit of capture probes that include an x-y barcode. For example, a plurality of capture proximally-associated biological analyte pairs can be analyzed, and the various parings between members of the plurality of capture proximally-associated biological analyte pairs can be used to create a three-dimensional pairing map. In some embodiments, a substrate can include capture probes (e.g., capture probes that are capable of capturing proximally-associated biological analyte pairs) that include an x-y barcode and capture probes that do not include an x-y barcode. For example, one or more capture probes on the substrate

EXAMPLES

Example 1—Methods for Spatial Profiling a Plurality of Biological Analytes Comprising Spatially-Programmed Capture Probes A biological sample is immobilized in a hydrogel matrix. The hydrogel matrix comprises a polymer having phenol moieties, azide moieties, or alkyne moieties. A plurality of spatially-programmed capture probes comprising a programmable migration domain, a first functional domain, a barcode sequence for an optically labeled probe, and a capture domain are provided. The plurality of spatially-programmed capture probes are allowed to migrate in the matrix. The plurality of spatially-programmed capture probes are immobilized in the matrix. Imaging is used to determine the plurality of spatially-programmed capture probes. The plurality of spatially-programmed capture probes are allowed to contact a plurality of biological analytes. The biological analyte of interest from the plurality of biological analytes is associated with a capture probe, thereby determining spatial location of the biological analyte of interest.

Example 2: Three-Dimensional Spatial Analysis of Analytes in a Biological Sample In a non-limiting example, a biological sample is embedded in a hydrogel matrix (e.g. a matrix that comprises a polymer having phenol moieties, azide moieties, or alkyne moieties). Target molecules of interest can be cross-linked with the hydrogel. A plurality of z-dimensional capture probes are introduced to the matrix and migrated through the matrix in one direction to a migration position in the biological sample. The z-dimensional capture probes include a first hybridization domain, a z-dimensional barcode, and a capture domain (e.g. an oligo dT sequence). At a migration position of the z-dimensional probe, a biological analyte is captured by a z-dimensional probe. The migration position and optionally the z-dimensional barcode is determined, thereby associating the z-dimensional barcode with their corresponding position along the z-dimension. Methods for determining the migration position and the z-dimensional barcode include confocal imaging or other suitable imaging methods. Upper and lower markers along the direction of migration can be used to determine the migration limits of the z-dimensional capture probes.

The biological sample is contacted with a solid substrate that includes a plurality of x-y dimensional capture probes. Members of the plurality of x-y dimensional capture probes include an x-y dimensional barcode, and a second hybridization domain. The z-dimensional capture probes, including those associated with a biological analyte, are migrated onto the solid substrate and allowed to interact and hybridize with the x-y dimensional capture probes under suitable conditions. The identities of the x-y dimensional probe and z-dimensional probes associated with the biological analyte are determined, thereby determining the 3-dimensional spatial position of the biological analyte in the biological sample.

Optionally, the biological sample is contacted with the solid substrate that includes a plurality of x-y dimensional probes prior to being embedded in a hydrogel matrix.

Example 3—Methods for Three-Dimensional Spatial Profiling of a Biological Analyte in a Biological Sample The cells of a biological sample are immobilized on a solid substrate. A proximity ligation reaction is performed on the biological sample such that pairs of proximal biological analytes are associated with each other. The biological sample is imaged. The biological sample is contacted with a solid support comprising a plurality of capture probes, wherein the capture probes individually comprise a molecular barcode and a capture domain, such that the proximally-associated biological analytes in the biological sample interact with the capture probes. The capture probes/proximally-associated biological analyte pairs are analyzed, and the proximally-associated biological analyte pairs are correlated with the distinct spatial position of the solid support. The 3-dimensional spatial profile of the biological analytes in the biological sample is reconstructed by analyzing the determined 2-dimensional spatial profile of the captured proximally-associated analyte pairs in conjunction with the determined identities of the biological analytes of the proximally-associated biological analyte pairs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for determining a location of an analyte in three-dimensional space in a tissue sample, the method comprising:
   (a) placing the tissue sample on an array and immobilizing the tissue sample by adding a hydrogel matrix to the tissue sample on the array, wherein the hydrogel matrix comprises a polymer;
   (b) adding a plurality of spatially-programmed capture probes to the hydrogel matrix, wherein a spatially-programmed capture probe in the plurality of spatially-programmed capture probes comprises:
      (i) a programmable migration domain that migrates to a z-axis location in the tissue sample;
      (ii) a detectable moiety; and
      (iii) a spatially-programmed capture domain that binds to the analyte;
   (c) migrating the plurality of spatially-programmed capture probes into the hydrogel matrix from a point distal to a surface of the hydrogel matrix;
   (d) hybridizing the spatially-programmed capture probe of the plurality of the spatially programmed capture probes to the analyte, thereby generating a hybridized spatially-programmed capture probe;
   (e) detecting a z-axis location of the detectable moiety of the spatially programmed capture probe in the tissue sample, thereby determining the z-axis location of the spatially-programmed capture probe and analyte in the tissue sample;
   (f) migrating the hybridized spatially-programmed capture probe to the array, wherein the array comprises a plurality of affixed capture probes, wherein an affixed capture probe of the plurality of affixed capture probes comprises a spatial barcode and a capture domain that hybridizes to the hybridized spatially-programmed capture probe; and
   (g) determining (i) a sequence of the hybridized spatially-programmed capture probe, or a complement thereof, (ii) a sequence of the spatial barcode, or a complement thereof, and (iii) all or part of the sequence of the analyte, or a complement thereof, and using the determined sequences of (i), (ii), and (iii), and the determined z-axis location in (e), to identify the location of the analyte in the three-dimensional space in the tissue sample.

2. The method of claim 1, wherein the polymer comprises a moiety selected from the group consisting of a phenol moiety, an azide moiety, and an alkyne moiety.

3. The method of claim 1, wherein the polymer comprises four monomers of polyethylene glycol and a plurality of phenol moieties, wherein a phenol moiety of the plurality of phenol moieties is affixed to each of the four monomers of polyethylene glycol.

4. The method of claim 3, wherein the polymer further comprises a plurality of azide moieties, wherein an azide moiety of the plurality of azide moieties is affixed to each of the four monomers of polyethylene glycol.

5. The method of claim 3, wherein the polymer further comprises a plurality of alkyne moieties, wherein an alkyne moiety of the plurality of alkyne moieties is affixed to each of the four monomers of polyethylene glycol.

6. The method of claim 1, further comprising extending a 3' end of the spatially-programmed capture probe prior to step (f).

7. The method of claim 1, wherein the spatially-programmed capture probe further comprises a cleavage domain comprising a recognition sequence for a restriction endonuclease, wherein upon cleavage of the cleavage domain, the programmable migration domain is released from the spatially-programmed capture probe.

8. The method of claim 1, wherein the migrating the hybridized spatially-programmed capture probe is performed using active migration, wherein the active migration uses an electric field, a magnetic field, a charged gradient, or any combination thereof.

9. The method of claim 1, wherein step (g) comprises sequencing (i) the hybridized spatially-programmed capture probe, or a complement thereof, (ii) the spatial barcode, or a complement thereof, and (iii) all or part of the analyte, or a complement thereof.

10. A method for determining a location of a nucleic acid in a tissue sample in a three dimensional space, the method comprising:

(a) placing the tissue sample on an array and immobilizing the tissue sample by adding a hydrogel matrix to the tissue sample on the array, wherein the hydrogel matrix comprises a polymer;

(b) adding a plurality of pairs of spatially-programmed capture probes to the hydrogel matrix, wherein a pair of spatially-programmed capture probes in the plurality of pairs of spatially-programmed capture probes comprises a first spatially-programmed capture probe and a second spatially-programmed capture probe, wherein:

the first and the second spatially-programmed capture probe comprises a detectable moiety;

and each of the first spatially-programmed capture probe and the second spatially-programmed capture probe comprise a programmable migration domain that migrates to a z-axis location in the tissue sample, (c) migrating the pair of spatially-programmed capture probes comprising the detectable moiety into the hydrogel matrix from a surface of the hydrogel matrix that is distal to a surface of the hydrogel matrix;

(d) hybridizing the first spatially-programmed capture probe and the second spatially-programmed capture probe to the nucleic acid;

(e) ligating the first spatially-programmed capture probe and the second spatially-programmed capture probe to generate a ligation product;

(f) detecting the z-axis location of the detectable moiety in the tissue sample, thereby determining the z-axis location of the ligation product in the tissue sample;

(g) migrating the ligation product to the array, wherein the array comprises a plurality of affixed capture probes, wherein an affixed capture probe of the plurality of affixed capture probes comprises a spatial barcode and a capture domain that hybridizes to a sequence in the ligation product; and (h) determining (i) a sequence of the ligation product, or a complement thereof, and (ii) the sequence of the spatial barcode, or a complement thereof, and using the determined sequences of (i) and (ii), and the determined z-axis location of the detectable moiety in (f), to identify a three-dimensional location of the nucleic acid in the tissue sample.

11. The method of claim 10, wherein the polymer comprises a moiety from the group consisting of a phenol moiety, an azide moiety, and an alkyne moiety.

12. The method of claim 11, wherein the polymer further comprises a plurality of azide moieties, wherein an azide moiety of the plurality of azide moieties is affixed to each of four monomers of polyethylene glycol.

13. The method of claim 1, wherein the polymer further comprises a plurality of alkyne moieties, wherein an alkyne moiety of the plurality of alkyne moieties is affixed to each of four monomers of polyethylene glycol.

14. The method of claim 10, wherein the polymer comprises four monomers of polyethylene glycol, and a plurality of phenol moieties, wherein a phenol moiety of the plurality of phenol moieties is affixed to each of the four monomers of polyethylene glycol.

15. The method of claim 10, wherein:

the first spatially-programmed capture probe further comprises a cleavage domain, wherein upon cleavage of the cleavage domain, the programmable migration domain is released from the first spatially-programmed capture probe; and/or the second spatially-programmed capture probe further comprises a cleavage domain, wherein upon cleavage of the cleavage domain, the programmable migration domain is released from the second spatially-programmed capture probe.

16. The method of claim 10, wherein the migrating the pair of spatially-programmed capture probes is performed using active migration, wherein the active migration uses an electric field, a magnetic field, a charged gradient, or any combination thereof.

17. The method of claim 10, wherein step (h) comprises sequencing (i) all or a part of the ligation product, or a complement thereof, and (ii) the spatial barcode, or a complement thereof.

18. The method of claim 10, wherein the detecting the z-axis of the detectable moiety in step (f) comprises imaging the tissue sample using confocal microscopy, and wherein the imaging identifies a region of interest in the tissue sample.

19. The method of claim 10, wherein the programmable migration domain comprises a polyethylene glycol, a folded three-dimensional oligonucleotide domain, a charged domain, a protein domain, a size-specific domain, an electromagnetic domain, or any combination thereof.

20. The method of claim 10, wherein the detectable moiety comprises one or more fluorescent labels, or one or more heavy metals.

\* \* \* \* \*

UNITED STATES PATENT AND TRADEMARK OFFICE
CERTIFICATE OF CORRECTION

| | |
|---|---|
| PATENT NO. | : 11,926,822 B1 |
| APPLICATION NO. | : 17/481810 |
| DATED | : March 12, 2024 |
| INVENTOR(S) | : Shalini Gohil and Eswar Prasad Ramachandran Iyer |

It is certified that error appears in the above-identified patent and that said Letters Patent is hereby corrected as shown below:

In the Claims

Column 55, Line 47, in Claim 1, delete "spatially programmed" and insert -- spatially-programmed --.

Column 56, Line 66, in Claim 10, delete "three dimensional" and insert -- three-dimensional --.

Column 58, Line 5, in Claim 13, delete "1" and insert -- 11, --.

Signed and Sealed this
Thirtieth Day of April, 2024

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Synthetic RAD peptide sequence

<400> SEQUENCE: 1

Arg Ala Asp Ala Arg Ala Asp Ala Arg Ala Asp Ala Arg Ala Asp Ala
1               5                   10                  15

```
<210> SEQ ID NO 2
<211> LENGTH: 16
<212> TYPE: PRT
<213> ORGANISM: Artificial Sequence
<220> FEATURE:
<223> OTHER INFORMATION: Synthetic EAK16 peptide sequence

<400> SEQUENCE: 2

Ala Glu Ala Glu Ala Lys Ala Lys Ala Glu Ala Glu Ala Lys Ala Lys
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic KLD12 peptide sequence

<400> SEQUENCE: 3

Lys Leu Asp Leu Lys Leu Asp Leu Lys Leu Asp Leu
1               5                   10
```